(12) United States Patent
Enomoto et al.

(10) Patent No.: US 6,242,634 B1
(45) Date of Patent: Jun. 5, 2001

(54) PYRIMIDIN-4-ONE DERIVATIVES, THEIR USE, INTERMEDIATES FOR THEIR PRODUCTION, AND PROCESSES FOR PRODUCING THESE INTERMEDIATES

(75) Inventors: Masayuki Enomoto, Takarazuka; Hisayuki Hoshi, Toyonaka; Yuzuru Sanemitsu, Kobe, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/584,378

(22) Filed: May 31, 2000

Related U.S. Application Data

(62) Division of application No. 09/011,562, filed as application No. PCT/JP96/02169 on Aug. 1, 1996, now Pat. No. 6,100,257.

(30) Foreign Application Priority Data

Aug. 10, 1995 (JP) .................................... 7-204519
Mar. 14, 1996 (JP) .................................... 8-57365

(51) Int. Cl.[7] ......................... C07C 255/00; C07C 69/66; C07C 211/00; C07C 321/00
(52) U.S. Cl. ............... 558/388; 560/9; 560/47; 560/55; 560/83; 558/389; 558/396; 558/398; 558/399; 558/406; 558/409; 558/410; 564/442; 568/25; 568/663
(58) Field of Search .................. 558/388, 406, 558/409, 410, 389, 396, 398, 399; 560/9, 47, 55, 83; 564/442; 568/663, 25

(56) References Cited

U.S. PATENT DOCUMENTS

| | | | |
|---|---|---|---|
| 3,944,571 | * | 3/1976 | Sutton et al. ................. 260/343.6 |
| 5,726,124 | | 3/1998 | Tice et al. ........................ 504/193 |
| 5,750,549 | * | 5/1998 | Caldwell et al. ................. 514/364 |

FOREIGN PATENT DOCUMENTS

| | | |
|---|---|---|
| 3816994A1 | 11/1989 | (DE) . |
| 0168262A2 | 1/1986 | (EP) . |
| 253310 | * 1/1988 | (EP) . |
| 0544166A2 | 6/1993 | (EP) . |
| 0561319A1 | 9/1993 | (EP) . |
| 0568041A1 | 11/1993 | (EP) . |
| 0617033A1 | 9/1994 | (EP) . |
| 2130214A | 5/1984 | (GB) . |

OTHER PUBLICATIONS

Chemical Abstracts, vol. 51, No. 10, 1957, No. 9629g.
Chemical Abstracts, vol. 88, No. 21, 1978, No. 152546n.

* cited by examiner

*Primary Examiner*—Richard L. Raymond
*Assistant Examiner*—Tamthom N. Truong

(57) ABSTRACT

Novel pyrimidin-4-one derivatives of formula [1] are provided, which are useful as active ingredients of herbicides, wherein $R^1$ is hydrogen or alkyl; $R^2$ is alkyl optionally substituted with halogen; $R^3$ is alkyl optionally substituted with halogen, alkenyl, or alkynyl; and Q is substituted phenyl. Also provided are intermediates for their production and processes for producing these intermediates.

5 Claims, No Drawings

PYRIMIDIN-4-ONE DERIVATIVES, THEIR USE, INTERMEDIATES FOR THEIR PRODUCTION, AND PROCESSES FOR PRODUCING THESE INTERMEDIATES

This application is a divisional of application Ser. No. 09/011,562, filed on Feb. 10, 1998 now U.S. Pat. No. 6,100,257. Application No. 09/011,562 is the national phase of PCT International Application No. PCT/JP96/02169 filed on Aug. 1, 1996 under 35 U.S.C. § 371. The entire contents of each of the above-identified applications are hereby incorporated by reference.

TECHNICAL FIELD

The present invention relates to pyrimidin-4-one derivatives, their use, intermediates for their production, and processes for producing these intermediates.

DISCLOSURE OF INVENTION

The present inventors have intensively studied to find a compound having excellent herbicidal activity. As a result, they have found that pyrimidin-4-one derivatives represented by formula [1] as depicted below have excellent herbicidal activity, thereby completing the present invention.

Thus the present invention provides a compound of the formula:

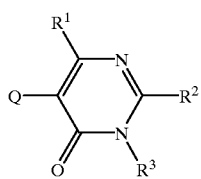

[1]

wherein $R^1$ is hydrogen or $C_1$–$C_3$ alkyl; $R^2$ is $C_1$–$C_3$ alkyl optionally substituted with one or more halogen atoms; $R^3$ is $C_1$–$C_6$ alkyl optionally substituted with one or more halogen atoms, $C_3$–$C_6$ alkenyl, or $C_3$–$C_6$ alkynyl; and Q is substituted phenyl (herein-after referred to as the present compound(s)); and a herbicide containing it as an active ingredient.

The present invention also provides a process for producing compound [1], which comprises reacting a compound of the formula:

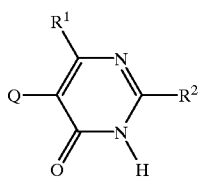

[2]

wherein Q, $R^1$, and $R^2$ are as defined above, with a compound of the formula:

$$R^3\text{-D} \quad [3]$$

wherein D is chlorine, bromine, iodine, methanesulfonyloxy, trifluoromethanesulfonyloxy, or p-toluenesulfonyloxy; and $R^3$ is as defined above.

The present invention further provides a compound of the formula:

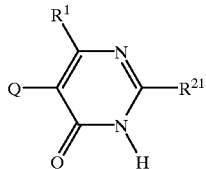

[4]

wherein Q and $R^1$ are as defined above; $R^{21}$ is $C_1$–$C_3$ alkyl substituted with one or more halogen atoms, which is useful as an intermediate for the production of some of the present compounds; and a process for producing a compound of the formula:

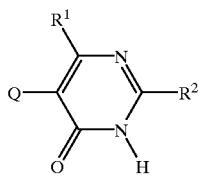

[2]

wherein Q, $R^1$, and $R^2$ are as defined above, which comprises reacting a compound of the formula:

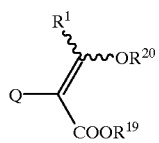

[5]

wherein $R^{19}$ and $R^{20}$ are independently $C_1$–$C_3$ alkyl, and Q and $R^1$ are as defined above, with a compound of the formula:

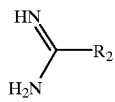

[6]

wherein $R^2$ is as defined above.

The compound [2] may be present as a compound of the formula:

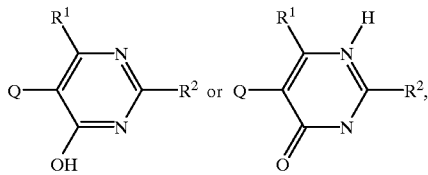

which is a tautomer thereof.

Examples of Q in the present invention include [Q-1], [Q-2], [Q-3], [Q-4], or [Q-5] of the formula:

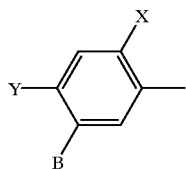
[Q-1]

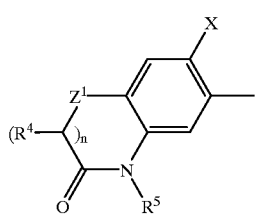
[Q-2]

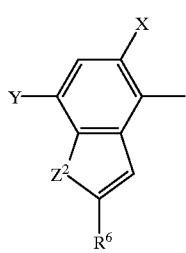
[Q-3]

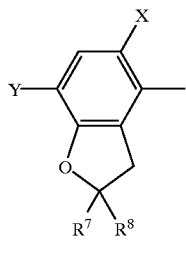
[Q-4]

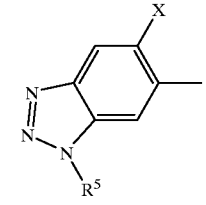
[Q-5]

wherein X is hydrogen or halogen;
Y is halogen, nitro, cyano, or trifluoromethyl;
$Z^1$ is oxygen, sulfur, NH, or methylene;
$Z^2$ is oxygen or sulfur;
n is 0 or 1;
B is hydrogen, halogen, nitro, cyano, chlorosulfonyl, —$OR^{10}$, —$SR^{10}$, —$SO_2$—$OR^{10}$, —$N(R^{10})R^{11}$, —$SO_2N(R^{11})R^{12}$, —$NR^{11}(COR^{13})$, —$NR^{11}(SO_2R^{14})$, —$N(SO_2R^{14})$—$(SO_2R^{15})$, —$N(SO_2R^{14})(COR^{13})$, —$NHCOOR^{13}$, —$COOR^{13}$, —$CON(R^{11})R^{12}$, —$CSN$—$(R^{11})R^{12}$, —$COR^{16}$, —$CR^{17}$=$CR^{18}CHO$, —$CR^{17}$=$CR^{18}COOR^{13}$, $CR^{17}$=$CR^{18}CON$—$(R^{11})R^{12}$, —$CH_2CHCOOR^{13}$, or —$CH_2CHWCON(R^{11})R^{12}$, wherein W is hydrogen, chlorine, or bromine; $R^{10}$ is hydrogen, $C_1$–$C_6$ alkyl, $C_1$–$C_6$ haloalkyl, $C_3$–$C_8$ cycloalkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_2$–$C_8$ alkoxyalkyl, $C_2$–$C_8$ alkylthioalkyl, carboxy $C_1$–$C_6$ alkyl, ($C_1$–$C_6$ alkoxy)carbonyl $C_1$–$C_6$ alkyl, ($C_1$–$C_6$ haloalkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, —$CH_2CON$—$(R^{11})R^{12}$, —$CH_2COON(R^{11})R^{12}$, —$CH(C_1$–$C_4$ alkyl)$CON(R^{11})R^{12}$, or —$CH(C_1$–$C_4$ alkyl)$COON(R^{11})R^{12}$; $R^{11}$ and $R^{12}$ are independently hydrogen, $C_1$–$C_6$ alkyl, $C_1$–$C_6$ haloalkyl, $C_3$–$C_6$ alkenyl, $C_3$–$C_6$ alkynyl, cyano $C_1$–$C_6$ alkyl, $C_2$–$C_8$ alkoxyalkyl, $C_2$–$C_8$ alkylthioalkyl, carboxy $C_1$–$C_6$ alkyl, ($C_1$–$C_6$ alkoxy)carbonyl $C_1$–$C_6$ alkyl, or {($C_1$–$C_4$ alkoxy) $C_1$–$C_4$ alkoxy}carbonyl $C_1$–$C_6$ alkyl, or $R^{11}$ and $R^{12}$ are taken together to form tetramethylene, pentamethylene, or ethyleneoxyethylene; $R^{13}$ is hydrogen, $C_1$–$C_6$ alkyl, $C_1$–$C_6$ haloalkyl, or $C_3$–$C_8$ cycloalkyl; $R^{14}$ and $R^{15}$ are independently $C_1$–$C_6$ alkyl, $C_1$–$C_6$ haloalkyl, or phenyl optionally substituted with methyl or nitro; $R^{16}$ is hydrogen, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_8$ alkoxyalkyl, or hydroxy $C_1$–$C_6$ alkyl; and $R^{17}$ and $R^{18}$ are independently hydrogen or $C_1$–$C_6$ alkyl;

$R^4$ is hydrogen or $C_1$–$C_3$ alkyl, $R^5$ is hydrogen, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_2$–$C_8$ alkoxyalkyl, $C_3$–$C_8$ alkoxyalkoxyalkyl, carboxy $C_1$–$C_6$ alkyl, ($C_1$–$C_6$ alkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl$C_1$–$C_6$ alkyl, —$CH_2CON(R^{11})R^{12}$, —$CH_2COON(R^{11})R^{12}$, —$CH(C_1$–$C_4$ alkyl)$CON(R^{11})R^{12}$, —$CH(C_1$–$C_4$ alkyl)$COON(R^{11})R^{12}$, $C_1$–$C_8$ alkylthioalkyl, $C_1$–$C_6$ alkylsulfonyl, $C_1$–$C_6$ haloalkylsulfonyl, ($C_1$–$C_8$ alkyl)carbonyl, ($C_1$–$C_8$ alkoxy)carbonyl, or hydroxy $C_1$–$C_6$ alkyl;

$R^6$ is $C_1$–$C_6$ alkyl, $C_1$–$C_6$ haloalkyl, formyl, cyano, carboxyl, hydroxy $C_1$–$C_6$ alkyl, $C_1$–$C_6$ alkoxy $C_1$–$C_6$ alkyl, $C_1$–$C_6$ alkoxy $C_1$–$C_6$ alkoxy $C_1$–$C_6$ alkyl, ($C_1$–$C_6$ alkyl)carbonyloxy $C_1$–$C_6$ alkyl, ($C_1$–$C_6$ haloalkyl)carbonyloxy $C_1$–$C_6$ alkyl, ($C_1$–$C_6$ alkoxy)carbonyl, or ($C_1$–$C_6$ alkyl)carbonyl;

$R^7$ is hydrogen or $C_1$–$C_6$ alkyl; and $R^8$ is $C_1$–$C_6$ alkyl, $C_1$–$C_6$ haloalkyl, $C_1$–$C_6$ hydroxyalkyl, $C_2$–$C_8$ alkoxyalkyl, $C_3$–$C_{10}$ alkoxyalkoxyalkyl, ($C_1$–$C_5$ alkyl)carbonyloxy $C_1$–$C_6$ alkyl, ($C_1$–$C_6$ haloalkyl)carbonyloxy $C_1$–$C_6$ alkyl, carboxyl, carboxy $C_1$–$C_6$ alkyl, ($C_1$–$C_8$ alkoxy)carbonyl, ($C_1$–$C_6$ haloalkoxy)carbonyl, ($C_3$–$C_{10}$ cycloalkoxy)carbonyl, ($C_3$–$C_8$ alkenyloxy)carbonyl, ($C_3$–$C_8$ alkynyloxy)carbonyl, aminocarbonyl, ($C_1$–$C_6$ alkyl)aminocarbonyl, di($C_1$–$C_6$ alkyl)aminocarbonyl, ($C_1$–$C_6$ alkyl)aminocarbonyloxy $C_1$–$C_6$ alkyl, or di($C_1$–$C_6$ alkyl)aminocarbonyloxy $C_1$–$C_6$ alkyl.

In the above definition of the present compounds, the respective substituents are exemplified as follows:

Examples of the $C_1$–$C_3$ alkyl represented by $R^1$ include methyl, ethyl, and isopropyl.

Examples of the $C_1$–$C_3$ alkyl optionally substituted with one or more halogen atoms, which is represented by $R^2$, include methyl, ethyl, isopropyl, trichloromethyl, trifluoromethyl, difluoromethyl, chlorodifluoromethyl, and pentafluoroethyl.

Examples of the $C_1$–$C_6$ alkyl optionally substituted with one or more halogen atoms, which is represented by $R^3$, include methyl, ethyl, isopropyl, difluoromethyl, and bromodifluoromethyl.

Examples of the $C_3$–$C_6$ alkenyl represented by $R^3$ include allyl and 1-methyl-2-propenyl.

Examples of the $C_3$–$C_6$ alkynyl represented by $R^3$ include propargyl and 1-methyl-2-propynyl.

In the formulas [Q-1], [Q-2], [Q-3], [Q-4], and [Q-5], the respective substituents are exemplified as follows:

Examples of the halogen represented by X, Y, and B include chlorine, fluorine, bromine, and iodine.

Examples of the $C_1$–$C_6$ alkyl represented by $R^{10}$ include methyl, ethyl, isopropyl, propyl, isobutyl, butyl, t-butyl, amyl, isoamyl, and t-amyl.

Examples of the $C_1$–$C_6$ haloalkyl represented by $R^{10}$ include difluoromethyl, tetrafluoroethyl, and 2,2,2-trifluoroethyl.

Examples of the $C_3$–$C_8$ cycloalkyl represented by $R^{10}$ include cyclopropyl, cyclobutyl, cyclopentyl, and cyclohexyl.

Examples of the $C_3$–$C_6$ alkenyl represented by $R^{10}$ include allyl, 1-methyl-2-propenyl, 3-butenyl, 2-butenyl, 3-methyl-2-butenyl, and 2-methyl-3-butenyl.

Examples of the $C_3$–$C_6$ haloalkenyl represented by $R^{10}$ include 2-chloro-2-propenyl and 3,3-dichloro-2-propenyl.

Examples of the $C_3$–$C_6$ alkynyl represented by $R^{10}$ include propargyl, 1-methyl-2-propynyl, 2-butynyl, and 1,1-dimethyl-2-propynyl.

Examples of the $C_3$–$C_6$ haloalkynyl represented by $R^{10}$ include 3-bromo-2-propynyl.

Examples of the cyano $C_1$–$C_6$ alkyl represented by $R^{10}$ include cyanomethyl.

Examples of the $C_2$–$C_8$ alkoxyalkyl represented by $R^{10}$ include methoxymethyl, methoxyethyl, ethoxymethyl, and ethoxyethyl.

Examples of the $C_2$–$C_8$ alkylthioalkyl represented by $R^{10}$ include methylthiomethyl.

Examples of the carboxy $C_1$–$C_6$ alkyl represented by $R^{10}$ include carboxymethyl, 1-carboxyethyl, and 2-carboxyethyl.

Examples of the ($C_1$–$C_6$ alkoxy)carbonyl $C_1$–$C_6$ alkyl represented by $R^{10}$ include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

Examples of the ($C_1$–$C_6$ haloalkoxy)carbonyl $C_1$–$C_6$ alkyl represented by $R^{10}$ include 2,2,2-trifluoroethoxycarbonylmethyl.

Examples of the {($C_1$–$C_4$ alkoxy) $C_1$–$C_4$ alkoxy}carbonyl $C_1$–$C_6$ alkyl represented by $R^{10}$ include methoxymethoxycarbonylmethyl and 1-methoxymethoxycarbonylethyl.

Examples of the ($C_3$–$C_8$ cycloalkoxy)carbonyl $C_1$–$C_6$ alkyl represented by $R^{10}$ include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, and 1-cyclohexyloxycarbonylethyl.

Examples of the $C_1$–$C_6$ alkyl represented by $R^{11}$ and $R^{12}$ include methyl, ethyl, propyl, butyl, isopropyl, and isobutyl.

Examples of the $C_1$–$C_6$ haloalkyl represented by $R^{11}$ and $R^{12}$ include chloroethyl and bromoethyl.

Examples of the $C_3$–$C_6$ alkenyl represented by $R^{11}$ and $R^{12}$ include allyl, 1-methyl-2-propenyl, and 3-butenyl.

Examples of the $C_3$–$C_6$ alkynyl represented by $R^{11}$ and $R^{12}$ include propargyl and 1-methyl-2-propynyl.

Examples of the cyano $C_1$–$C_6$ alkyl represented by $R^{11}$ and $R^{12}$ include cyanomethyl.

Examples of the $C_2$–$C_8$ alkoxyalkyl represented by $R^{11}$ and $R^{12}$ include methoxymethyl and ethoxyethyl.

Examples of the $C_2$–$C_8$ alkylthioalkyl represented by $R^{11}$ and $R^{12}$ include methylthiomethyl and methylthioethyl.

Examples of the carboxy $C_1$–$C_6$ alkyl represented by $R^{11}$ and $R^{12}$ include carboxymethyl and 1-carboxyethyl.

Examples of the ($C_1$–$C_6$ alkoxy)carbonyl $C_1$–$C_6$ alkyl represented by $R^{11}$ and $R^{12}$ include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

Examples of the {($C_1$–$C_4$ alkoxy) $C_1$–$C_4$ alkoxy}carbonyl $C_1$–$C_6$ alkyl represented by $R^{11}$ and $R^{12}$ include methoxymethoxycarbonylmethyl and 1-methoxymethoxycarbonylethyl.

Examples of the $C_1$–$C_6$ alkyl represented by $R^{13}$ include methyl, ethyl, propyl, butyl, amyl, isopropyl, isobutyl, and isoamyl.

Examples of the $C_1$–$C_6$ haloalkyl represented by $R^{13}$ include 2,2,2-trifluoroethyl, chloromethyl, trichloromethyl, and bromomethyl.

Examples of the $C_3$–$C_7$ cycloalkyl represented by $R^{13}$ include cyclopropyl, cyclobutyl, cyclopentyl, and cyclohexyl.

Examples of the $C_1$–$C_6$ alkyl represented by $R^{14}$ and $R^{15}$ include methyl, ethyl, propyl, butyl, and isopropyl.

Examples of the $C_1$–$C_6$ haloalkyl represented by $R^{14}$ and $R^{15}$ include trifluoromethyl, 2,2,2-trifluoroethyl, 2-chloroethyl, chloromethyl, and trichloromethyl.

Examples of the phenyl optionally substituted by methyl or nitro, which is represented by $R^{14}$ and $R^{15}$, include phenyl, p-methylphenyl, 2-nitrophenyl, 3-nitrophenyl, and 4-nitrophenyl.

Examples of the $C_1$–$C_6$ alkyl represented by $R^{16}$ include methyl, ethyl, propyl, butyl, amyl, isopropyl, isobutyl, t-butyl, isoamyl, and t-amyl.

Examples of the $C_1$–$C_6$ haloalkyl represented by $R^{16}$ include chloromethyl, dichloromethyl, bromomethyl, dibromomethyl, 1-chloroethyl, 1,1-dichloroethyl, 1-bromoethyl, and 1,1-dibromoethyl.

Examples of the $C_2$–$C_6$ alkenyl represented by $R^{16}$ include vinyl, allyl, 1-propenyl, and 1-methyl-2-propenyl.

Examples of the $C_2$–$C_6$ haloalkenyl represented by $R^{16}$ include 3,3-dichloro-2-propenyl and 3,3-dibromo-2-propenyl.

Examples of the $C_2$–$C_6$ alkynyl represented by $R^{16}$ include 2-butynyl.

Examples of the $C_2$–$C_6$ haloalkynyl represented by $R^{16}$ include 3-bromo-2-propynyl.

Examples of the $C_2$–$C_8$ alkoxyalkyl represented by $R^{16}$ include methoxymethyl, ethoxymethyl, and isopropoxymethyl.

Examples of the hydroxy $C_1$–$C_6$ alkyl represented by $R^{16}$ include hydroxymethyl.

Examples of the $C_1$–$C_6$ alkyl represented by $R^{17}$ and $R^{18}$ include methyl.

Examples of the $C_1$–$C_3$ alkyl represented by $R^4$ include methyl.

Examples of the $C_1$–$C_6$ alkyl represented by $R^5$ include methyl, ethyl, propyl, butyl, amyl, isopropyl, isobutyl, and isoamyl.

Examples of the $C_1$–$C_6$ haloalkyl represented by $R^5$ include 2-chloroethyl, 2-bromoethyl, 3-chlorobutyl, 3-bromobutyl, difluoromethyl, and bromodifluoromethyl.

Examples of the $C_3$–$C_6$ alkenyl represented by $R^5$ include allyl, 1-methyl-2-propenyl, 3-butenyl, 2-butenyl, 3-methyl-2-butenyl, and 2-methyl-3-butenyl.

Examples of the $C_3$–$C_6$ haloalkenyl represented by $R^5$ include 2-chloro-2-propenyl and 3,3-dichloro-2-propenyl.

Examples of the $C_3$–$C_6$ alkynyl represented by $R^5$ include propargyl, 1-methyl-2-propynyl, 2-butynyl, and 1,1-dimethyl-2-propynyl.

Examples of the $C_3$–$C_6$ haloalkynyl represented by $R^5$ include 3-iodo-2-propynyl and 3-bromo-2-propynyl.

Examples of the cyano $C_1$–$C_6$ alkyl represented by $R^5$ include cyanomethyl.

Examples of the $C_2$–$C_8$ alkoxyalkyl represented by $R^5$ include methoxymethyl, ethoxymethyl, and 1-methoxyethyl.

Examples of the $C_3$–$C_8$ alkoxyalkoxyalkyl represented by $R^5$ include methoxyethoxymethyl.

Examples of the carboxy $C_1$–$C_6$ alkyl represented by $R^5$ include carboxymethyl, 1-carboxyethyl, and 2-carboxyethyl.

Examples of the ($C_1$–$C_6$ alkoxy)carbonyl $C_1$–$C_6$ alkyl represented by $R^5$ include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

Examples of the {($C_1$–$C_4$ alkoxy) $C_1$–$C_4$ alkoxy}carbonyl $C_1$–$C_6$ alkyl represented by $R^5$ include methoxymethoxycarbonylmethyl and 1-methoxymethoxycarbonylethyl.

Examples of the ($C_3$–$C_8$ cycloalkoxy)carbonyl $C_1$–$C_6$ alkyl represented by $R^5$ include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, and 1-cyclohexyloxycarbonylethyl.

Examples of the $C_2$–$C_8$ alkylthioalkyl represented by $R^5$ include methylthiomethyl.

Examples of the $C_1$–$C_6$ alkylsulfonyl represented by $R^5$ include methanesulfonyl, ethanesulfonyl, and isopropylsulfonyl.

Examples of the $C_1$–$C_6$ haloalkylsulfonyl represented by $R^5$ include trifluoromethanesulfonyl, chloromethanesulfonyl, trichloromethanesulfonyl, 2-chloroethanesulfonyl, and 2,2,2-trifluoroethanesulfonyl.

Examples of the ($C_1$–$C_8$ alkyl)carbonyl represented by $R^5$ include acetyl, ethylcarbonyl, propylcarbonyl, and isopropylcarbonyl.

Examples of the ($C_1$–$C_8$ alkoxy)carbonyl represented by $R^5$ include methoxycarbonyl, ethoxycarbonyl, propoxycarbonyl, butoxycarbonyl, amyloxycarbonyl, isopropoxycarbonyl, isobutoxycarbonyl, t-butoxycarbonyl, isoamyloxycarbonyl, and t-amyloxycarbonyl.

Examples of the hydroxy $C_1$–$C_6$ alkyl represented by $R^5$ include hydroxymethyl, hydroxyethyl, and hydroxypropyl.

Examples of the $C_1$–$C_6$ alkyl represented by $R^6$ include methyl and ethyl.

Examples of the $C_1$–$C_6$ haloalkyl represented by $R^6$ include bromomethyl, dibromomethyl, tribromomethyl, 1-bromoethyl, chloromethyl, dichloromethyl, and trichloromethyl.

Examples of the hydroxy $C_1$–$C_6$ alkyl represented by $R^6$ include hydroxymethyl.

Examples of the $C_1$–$C_6$ alkoxy $C_1$–$C_6$ alkyl represented by $R^6$ include methoxymethyl, ethoxymethyl, propoxymethyl, and isopropoxymethyl.

Examples of the $C_1$–$C_6$ alkoxy $C_1$–$C_6$ alkoxy $C_1$–$C_6$ alkyl represented by $R^6$ include methoxymethoxymethyl, methoxyethoxymethyl, and ethoxymethoxymethyl.

Examples of the ($C_1$–$C_6$ alkyl)carbonyloxy $C_1$–$C_6$ alkyl represented by $R^6$ include acetyloxymethyl, ethylcarbonyloxymethyl, and isopropylcarbonyloxymethyl.

Examples of the ($C_1$–$C_6$ haloalkyl)carbonyloxy $C_1$–$C_6$ alkyl represented by $R^6$ include trifluoroacetyloxymethyl, chloroacetyloxymethyl, and trichloroacetyloxymethyl.

Examples of the ($C_1$–$C_6$ alkoxy)carbonyl represented by $R^6$ include methoxycarbonyl, ethoxycarbonyl, propoxycarbonyl, butoxycarbonyl, amyloxycarbonyl, isopropoxycarbonyl, isobutoxycarbonyl, and isoamyloxycarbonyl.

Examples of the ($C_1$–$C_6$ alkyl)carbonyl represented by $R^6$ include methylcarbonyl, ethylcarbonyl, and isopropylcarbonyl.

Examples of the $C_1$–$C_6$ alkyl represented by $R^7$ include methyl.

Examples of the $C_1$–$C_6$ alkyl represented by $R^8$ include methyl and ethyl.

Examples of the $C_1$–$C_6$ haloalkyl represented by $R^8$ include chloromethyl, bromomethyl, and fluoromethyl.

Examples of the $C_1$–$C_6$ hydroxyalkyl represented by $R^8$ include hydroxymethyl.

Examples of the $C_2$–$C_8$ alkoxyalkyl represented by $R^8$ include methoxymethyl, ethoxymethyl, isopropoxymethyl, butoxymethyl, and isobutoxymethyl.

Examples of the $C_3$–$C_{10}$ alkoxyalkoxyalkyl represented by $R^8$ include methoxymethoxymethyl, methoxyethoxymethyl, and ethoxymethoxymethyl.

Examples of the ($C_1$–$C_5$ alkyl)carbonyloxy $C_1$–$C_6$ alkyl represented by $R^8$ include acetyloxymethyl, ethylcarbonyloxymethyl, and isopropylcarbonyloxymethyl.

Examples of the ($C_1$–$C_6$ haloalkyl)carbonyloxy $C_1$–$C_6$ alkyl represented by $R^8$ include chloromethylcarbonyloxymethyl.

Examples of the carboxy $C_1$–$C_6$ alkyl represented by $R^8$ include carboxymethyl.

Examples of the ($C_1$–$C_8$)alkoxycarbonyl represented by $R^8$ include methoxycarbonyl, ethoxycarbonyl, propoxycarbonyl, butoxycarbonyl, amyloxycarbonyl, isopropoxycarbonyl, isobutoxycarbonyl, and isoamyloxycarbonyl.

Examples of the ($C_1$–$C_6$ haloalkoxy)carbonyl represented by $R^8$ include 2-chloroethoxycarbonyl, 2-bromoethoxycarbonyl, 3-chlorobutoxycarbonyl, 1-chloro-2-propoxycarbonyl, 1,3-dichloro-2-propoxycarbonyl, 2,2-dichloroethoxycarbonyl, 2,2,2-trifluoroethoxycarbonyl, 2,2,2-trichloroethoxycarbonyl, and 2,2,2-tribromoethoxycarbonyl.

Examples of the ($C_3$–$C_{10}$ cycloalkoxy)carbonyl represented by $R^8$ include cyclobutyloxycarbonyl, cyclopentyloxycarbonyl, and cyclohexyloxycarbonyl.

Examples of the ($C_3$–$C_8$ alkenyloxy)carbonyl represented by $R^8$ include allyloxycarbonyl and 3-butenyloxycarbonyl.

Examples of the ($C_3$–$C_8$ alkynyloxy)carbonyl represented by $R^8$ include propargyloxycarbonyl, 3-butynyloxycarbonyl, and 1-methyl-2-propynyloxycarbonyl.

Examples of the ($C_1$–$C_6$ alkyl)aminocarbonyl represented by $R^8$ include methylaminocarbonyl, ethylaminocarbonyl, and propylaminocarbonyl.

Examples of the di($C_1$–$C_6$ alkyl)aminocarbonyl represented by $R^8$ include dimethylaminocarbonyl, diethylaminocarbonyl, and diisopropylaminocarbonyl.

Examples of the ($C_1$–$C_6$ alkyl)aminocarbonyloxy $C_1$–$C_6$ alkyl represented by $R^8$ include methylaminocarbonyloxymethyl, ethylaminocarbonyloxymethyl, and propylaminocarbonyloxymethyl.

Examples of the di($C_1$–$C_6$ alkyl)aminocarbonyloxy $C_1$–$C_6$ alkyl represented by $R^8$ include dimethylaminocarbonyloxyalkyl and diethylaminocarbonyloxyalkyl.

In the present compounds, preferred substituents from the viewpoint of their herbicidal activity are as follows:

$R^1$ is preferably hydrogen;

$R^2$ is preferably $C_1$–$C_3$ alkyl substituted with one or more halogen atoms, more preferably methyl substituted with one or more fluorine atoms, or ethyl substituted with one or more fluorine atoms, and most preferably trifluoromethyl;

$R^3$ is preferably methyl or ethyl, more preferably methyl;

Q is preferably [Q-1], [Q-2], [Q-3], or [Q-4];

Y is preferably halogen;

$Z^1$ is preferably oxygen or sulfur;

$Z^2$ is preferably oxygen;

B is preferably hydrogen, nitro, —$OR^{10}$, —$SR^{10}$, —$NHR^{10}$, —$NHSO_2R^{14}$, —$COOR^{13}$, or —$CH_2CHWCOOR^{13}$, wherein W is preferably hydrogen or chlorine; $R^{10}$ is preferably $C_1$–$C_6$ alkyl, $C_3$–$C_8$ cycloalkyl, $C_3$–$C_6$ alkenyl, $C_3$–$C_6$ haloalkenyl, $C_3$–$C_6$ alkynyl, cyano $C_1$–$C_6$ alkyl, or ($C_1$–$C_6$ alkoxy)carbonyl $C_1$–$C_6$ alkyl; $R^{13}$ is preferably $C_1$–$C_6$ alkyl; and $R^{14}$ is preferably $C_1$–$C_6$ alkyl;

$R^5$ is preferably $C_1$–$C_6$ alkyl, $C_3$–$C_6$ alkenyl, or $C_3$–$C_6$ alkynyl;

$R^6$ is preferably $C_1$–$C_6$ alkyl, $C_1$–$C_6$ haloalkyl, formyl, hydroxymethyl, $C_1$–$C_6$ alkoxymethyl, $C_1$–$C_6$ alkylcarbonyloxymethyl, or $C_1$–$C_6$ alkoxycarbonyl;

$R^7$ is preferably hydrogen or methyl; and $R^8$ is preferably methyl, hydroxymethyl, $C_1$–$C_6$ alkoxymethyl, ($C_1$–$C_5$ alkyl)carbonyloxymethyl, carboxyl, or ($C_1$–$C_6$ alkoxy)carbonyl.

Preferred examples of the present compounds from the viewpoint of their herbicidal activity are those which contain the above preferred substituents in combination. Among these compounds are more preferred ones wherein $R^2$ is methyl substituted with one or more fluorine atoms, or ethyl substituted with one or more fluorine atoms.

Among these compounds are more preferred ones wherein $R^2$ is trifluoromethyl.

Among these compounds are more preferred ones wherein Q is [Q-1] or [Q-2].

When Q is [Q-1], more preferred compounds are those wherein B is —$OR^{10}$ or —$NHR^{10}$. Among these compounds are more preferred ones wherein when B is —$OR^{10}$, then $R^{10}$ is $C_3$–$C_6$ alkynyl or ($C_1$–$C_6$ alkoxy)carbonyl $C_1$–$C_6$ alkyl; or when B is —$NHR^{10}$, then $R^{10}$ is ($C_1$–$C_6$ alkoxy)carbonyl $C_1$–$C_6$ alkyl. Among these compounds are more preferred ones wherein $R^{10}$ is $C_3$–$C_4$ alkynyl, ($C_1$–$C_6$ alkoxy)carbonylmethyl, or 1-($C_1$–$C_6$ alkoxy)carbonylethyl. Among these compounds are more preferred ones wherein $R^1$ is hydrogen; $R^3$ is methyl; X is fluorine; and Y is chlorine.

When Q is [Q-2], more preferred compounds are those wherein $Z^1$ is oxygen; n is 1; $R^4$ is hydrogen; and $R^5$ is $C_3$–$C_6$ alkynyl. Among these compounds are more preferred ones wherein $R^5$ is $C_3$–$C_4$ alkynyl. Among these compounds are those more preferred ones wherein $R^1$ is hydrogen; $R^3$ is methyl; and X is fluorine.

Particularly preferred compounds are those wherein $R^1$ is hydrogen; $R^2$ is trifluoromethyl; $R^3$ is methyl; Q is [Q-1]; X is fluorine; Y is chlorine; and B is propargyloxy; those wherein $R^1$ is hydrogen; $R^2$ is trifluoromethyl; $R^3$ is methyl; Q is [Q-1]; X is fluorine; Y is chlorine; and B is 1-(ethoxycarbonyl)ethoxy; those wherein $R^1$ is hydrogen; $R^2$ is trifluoromethyl; $R^3$ is methyl; Q is [Q-1]; X is fluorine; Y is chlorine; and B is 1-(methoxycarbonyl)ethoxy; and those wherein $R^1$ is hydrogen; $R^2$ is trifluoromethyl; $R^3$ is methyl; Q is [Q-2]; X is fluorine; $Z^1$ is oxygen; n is 1; $R^4$ is hydrogen; and $R^5$ is propargyl.

Some of the present compounds have optical isomers based on the presence of at least one asymmetric carbon atom, and all of the optical isomers are, of course, included within the scope of the present invention.

The present compounds can be produced by various production processes as described below.

(Production Process 1)

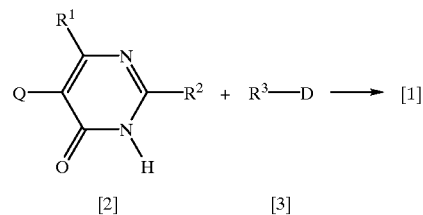

wherein $R^1$, $R^2$, $R^3$, Q, and D are as defined above.

The reaction is usually effected in the presence of a base in a solvent. The reaction temperature is usually in the range of −20° to 150° C., preferably 0° to 100° C. The reaction time is usually in the range of a moment to 96 hours. The amounts of the reagents to be used in the reaction are usually 1 to 5 moles of compound [3] and usually 1 mole to an excess of the base, per mole of compound [2].

Examples of the solvent which can be used include aliphatic hydrocarbons such as hexane, heptane, ligroin, cyclohexane, and petroleum ether; aromatic hydrocarbons such as benzene, toluene, and xylene; ethers such as diethyl ether, diisopropyl ether, dioxane, tetrahydrofuran, and ethylene glycol dimethyl ether; nitro compounds such as nitromethane and nitrobenzene; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; ketones such as acetone and methyl isobutyl ketone; and mixtures thereof.

Examples of the base used in the reaction include inorganic bases such as sodium hydride, potassium hydride, sodium hydroxide, potassium hydroxide, potassium carbonate, and sodium carbonate; and organic bases such as triethylamine, diisopropylethylamine, pyridine, 4-dimethylaminopyridine, N,N-dimethylaniline, and N,N-diethylaniline.

After completion of the reaction, the reaction mixture is poured into water and the precipitated crystals are collected by filtration, or the reaction mixture is subjected to ordinary post-treatments such as extraction with an organic solvent and concentration, followed by, if necessary, subsequent purification by a technique such as chromatography or recrystallization. Thus the desired compound of the present invention can be isolated.

In the present production process, depending upon the reaction conditions, a compound of the formula:

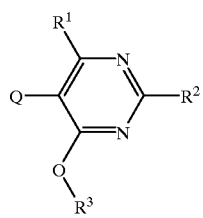

[7]

wherein Q, $R^1$, $R^2$, and $R^3$ are as defined above, may be formed as a by-product and can be isolated in the same manner as in the isolation of the above present compound. Some of the compounds [7] have herbicidal activity.

Production Process 2

This is the production process according to the following scheme:

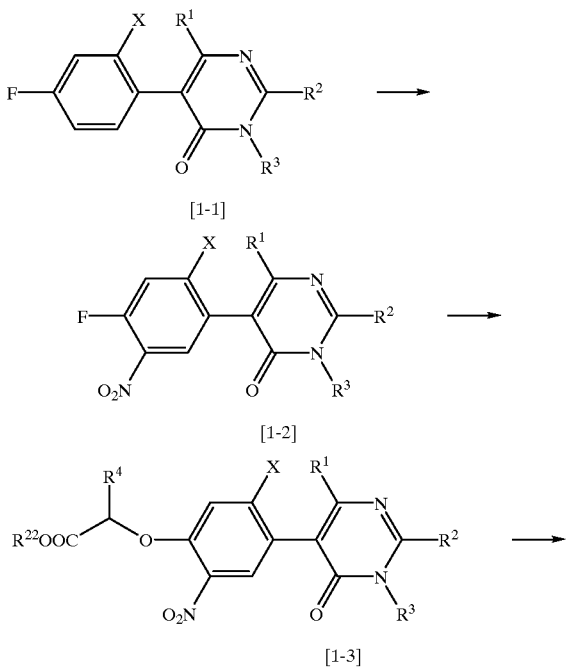

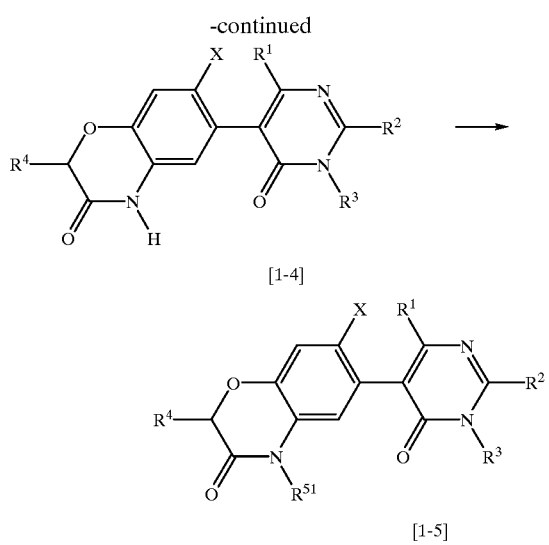

wherein $R^{22}$ is $C_1$–$C_6$ alkyl; $R^{51}$ is a substituent other than hydrogen, which is included in the definition of $R^5$; and $R^1$, $R^2$, $R^3$, $R^4$, and X are as defined above.

Process for Producing Compound [1-2] from Compound [1-1]

Compound [1-2] can be produced by reacting compound [1-1] with a nitrating agent in a solvent.

Nitrating agent: nitric acid or the like
Amount of nitrating agent: 1 to 10 moles per mole of compound [1-1]
Solvent: sulfuric acid or the like
Temperature: −10° C. to room temperature
Time: a moment to 24 hours Process for Producing Compound [1-3] from Compound [1-2]

Compound [1-3] can be produced by reacting compound [1-2] with a compound of the formula:

[8]

wherein $R^4$ and $R^{22}$ are as defined above, in the presence of potassium fluoride in a solvent.

Amount of compound [8]: 1 to 50 moles per mole of compound [1-2]
Amount of potassium fluoride: 1 to 50 moles per mole of compound [1-2]
Solvent: 1,4-dioxane or the like
Temperature: room temperature to refluxing temperature under heating
Time: a moment to 96 hours Process for Producing Compound [1-4] from Compound [1-3]

Compound [1-4] can be produced by reducing compound [1-3] with iron powder in the presence of an acid in a solvent.

Amount of iron powder: 3 moles to an excess per mole of compound [1-3]
Acid: acetic acid or the like
Amount of acid: 1 to 10 moles Solvent: water, ethyl acetate, or the like
Temperature: room temperature to refluxing temperature under heating
Time: a moment to 24 hours or recrystallization. Thus the present compound [1-5] can be obtained.

The above compound [1-3] can also be produced according to the following scheme:

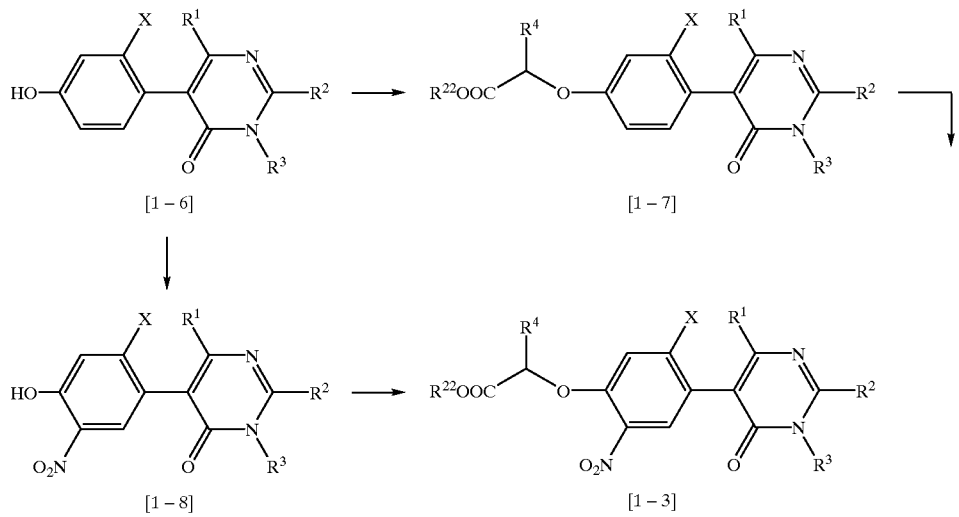

Process for Producing Compound [1-5] from Compound [1-4]

Compound [1-5] can be produced by reacting compound [1-4] with a compound of the formula:

$$R^{51}\text{-D} \qquad [9]$$

wherein $R^{51}$ and D are as defined above.

The reaction is usually effected in the presence of a base in a solvent. The reaction temperature is usually in the range of −20° to 150° C., preferably 0° to 50° C. The reaction time is usually in the range of a moment to 48 hours.

The amounts of the reagents to be used in the reaction are usually 1 to 3 moles of compound [9] and usually 1 to 5 moles of the base, per mole of compound [1-4].

Examples of the base which can be used include inorganic bases such as sodium hydride, potassium hydride, sodium hydroxide, potassium hydroxide, potassium carbonate, and sodium carbonate; and organic bases such as triethylamine, diisopropylethylamine, pyridine, 4-dimethylaminopyridine, N,N-dimethylaniline, and N,N-diethylaniline.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, tetrahydrofuran, and ethylene glycol dimethyl ether; nitro compounds such as nitrobenzene; acid amides such as formamide, N,N-dimethylformamide, and acetamide; tertiary amines such as pyridine, triethylamine, diisopropylethylamine, N,N-dimethylamine, N,N-diethylaniline, and N-methylmorpholine; ketones such as acetone and methyl isobutyl ketone; and mixtures thereof.

After completion of the reaction, the reaction mixture is poured into water, if necessary, and subjected to ordinary post-treatments such as extraction with an organic solvent and concentration, followed by, if necessary, subsequent purification by a technique such as column chromatography wherein $R^1$, $R^2$, $R^3$, $R^4$, $R^{22}$, and X are as defined above.

Process for Producing Compound [1-7] from Compound [1-6]

Compound [1-7] can be produced by reacting compound [1-6] with a compound of the formula:

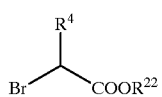

[10]

wherein $R^4$ and $R^{22}$ are as defined above, in the presence of a base in a solvent.

Amount of compound [10]: 1 to 2 moles per mole of compound [1-6]

Base: sodium hydride, potassium carbonate, or the like

Amount of base: 1 to 5 moles per mole of compound [1-6]

Solvent: 1,4-dioxane, N,N-dimethylformamide, or the like

Temperature: 0° to 100° C.

Time: a moment to 24 hours

Process for Producing Compound [1-3] from Compound [1-7]

Compound [1-3] can be produced by reacting compound [1-7] with a nitrating agent in a solvent.

Nitrating agent: nitric acid or the like

Amount of nitrating agent: 1 to 10 moles per mole of compound [1-7]

Solvent: sulfuric acid, acetic acid, or the like

Temperature: −10° C. to room temperature

Time: a moment to 24 hours

Process for Producing Compound [1-8] from Compound [1-6]

Compound [1-8] can be produced by reacting compound [1-6] with a nitrating agent in a solvent.

Nitrating agent: nitric acid or the like

Amount of nitrating agent: 1 to 10 moles per mole of compound [1-6]

Solvent: sulfuric acid, acetic acid, or the like

Temperature: −10° C. to room temperature

Time: a moment to 24 hours

Process for Producing Compound [1-3] from Compound [1-8]

Compound [1-3] can be produced by reacting compound [1-8) with compound [10] in the presence of a base in a solvent.

Amount of compound [10]: 1 to 2 moles per mole of compound [1-8]

Base: sodium hydride, potassium carbonate, or the like

Amount of base: 1 to 5 moles per mole of compound [1-8]

Solvent: 1,4-dioxane, N,N-dimethylformamide, or the like

Temperature: 0° to 100° C.

Time: a moment to 24 hours

Production Process 3

This is the production process according to the following scheme:

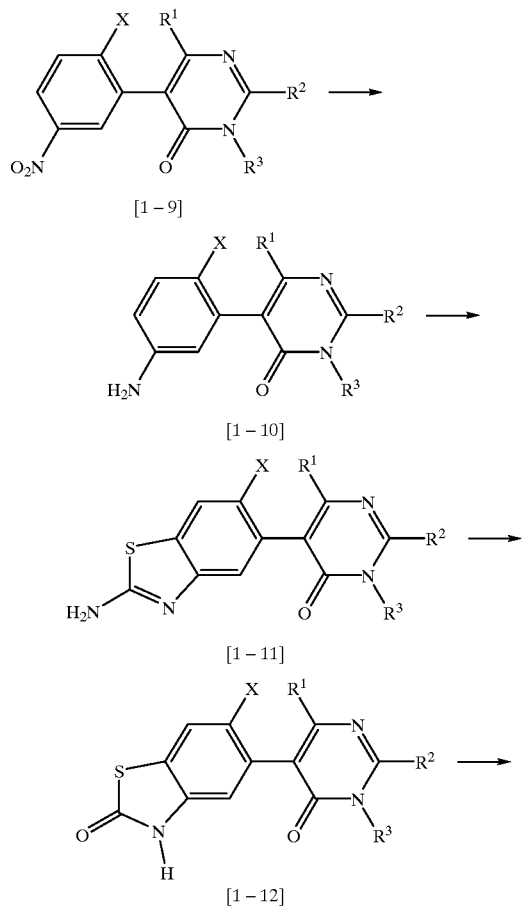

wherein X, $R^1$, $R^2$, $R^3$, $R^{51}$, and D are as defined above.

Process for Producing Compound [1-10] from Compound [1-9]

Compound [1-10] can be produced by reducing compound [1-9] with iron powder in the presence of an acid in a solvent.

Amount of iron powder: 3 moles to an excess per mole of compound [1-9]

Acid: acetic acid or the like

Amount of acid: 1 to 10 moles per mole of compound [1-9]

Solvent: water, ethyl acetate, or the like

Temperature: room temperature to refluxing temperature under heating

Time: a moment to 24 hours

Process for Producing Compound [1-11] from Compound [1-10]

Compound [1-11] can be produced by reacting compound [1-10] with sodium thiocyanate, potassium thiocyanate, or the like in a solvent, and then reacting it with bromine or chlorine in a solvent.

Amount of sodium thiocyanate, potassium thiocyanate, or the like: 1 to 10 moles per mole of compound [1-10]

Amount of bromine or chlorine: 1 to 10 moles per mole of compound [1-10]

Solvent: aqueous hydrochloric acid, aqueous acetic acid, aqueous sulfuric acid, or the like Temperature: 0° to 50° C.

Time: a moment to 150 hours

Process for Producing Compound [1-12] from Compound [1-11]

Compound [1-12] can be produced by 1) reacting compound [1-11] with sodium nitrite, potassium nitrite, or the like in a solvent, and then 2) heating it in an acidic solution.

<Reaction 1)>

Amount of sodium nitrite, potassium nitrite, or the like: 1 to 2 moles per mole of compound [1-11]

Solvent: aqueous hydrochloric acid or aqueous sulfuric acid

Temperature: −10° to 10° C.

Time: a moment to 5 hours

<Reaction 2)>

Acidic solution: aqueous hydrochloric acid, aqueous sulfuric acid, or the like

Temperature: 70° C. to refluxing temperature under heating

Time: a moment to 24 hours

Process for Producing Compound [1-13] from Compound [1-12]

Compound [1-13] can be produced by reacting compound [1-12] with compound [9] in the presence of a base in a solvent.

Amount of compound [9]: 1 to 3 moles per mole of compound [1-12]
Base: sodium hydride, potassium carbonate, or the like
Amount of base: 1 to 10 moles per mole of compound [1-12]
Solvent: 1,4-dioxane, N,N-dimethylformamide, or the like
Temperature: 0° to 100° C.
Time: a moment to 48 hours Production Process 4

This is the production process according to the following scheme:

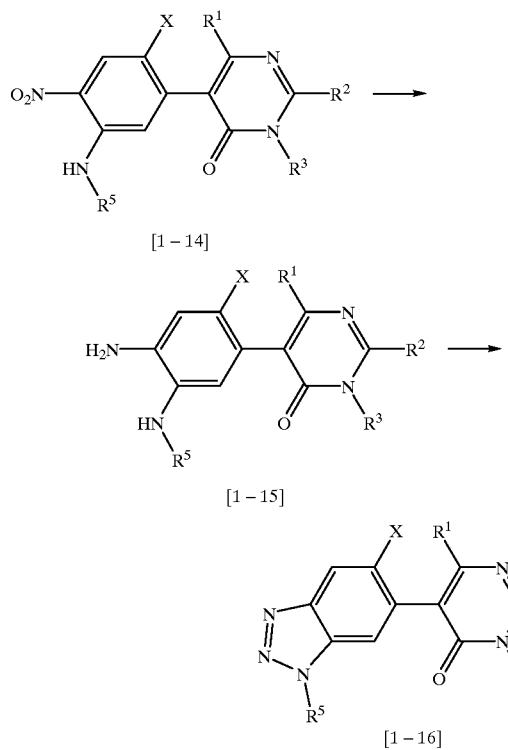

wherein X, $R^1$, $R^2$, $R^3$, and $R^5$ are as defined above.

Process for Producing Compound [1-15] from Compound [1-14]

Compound [1-15] can be produced by reducing compound [1-14] with iron powder in the presence of an acid in a solvent.

Amount of iron powder: 3 moles to an excess per mole of compound [1-14]
Acid: acetic acid or the like
Amount of acid: 1 to 10 moles per mole of compound [1-14]
Solvent: water, ethyl acetate, or the like
Temperature: room temperature to refluxing temperature under heating
Time: a moment to 24 hours Process for Producing Compound [1-16] from Compound [1-15]

Compound [1-16] can be produced by 1) reacting compound [1-15] with a nitrite salt in a solvent to form a diazonium salt, and then 2) raising the temperature to cause the cyclization of the diazonium salt in a solvent.

<Reaction 1)>
Nitrite salt: sodium nitrite, potassium nitrite, or the like
Amount of nitrite salt: 1 to 2 moles per mole of compound [1-15]
Solvent: aqueous hydrochloric acid, aqueous sulfuric acid, or the like
Temperature: −10° to 10° C.
Time: a moment to 5 hours <Reaction 2)>
Solvent: aqueous hydrochloric acid, aqueous sulfuric acid, or the like
Temperature: room temperature to 80° C.
Time: a moment to 24 hours Production Process 5

This is the production process according to the following scheme:

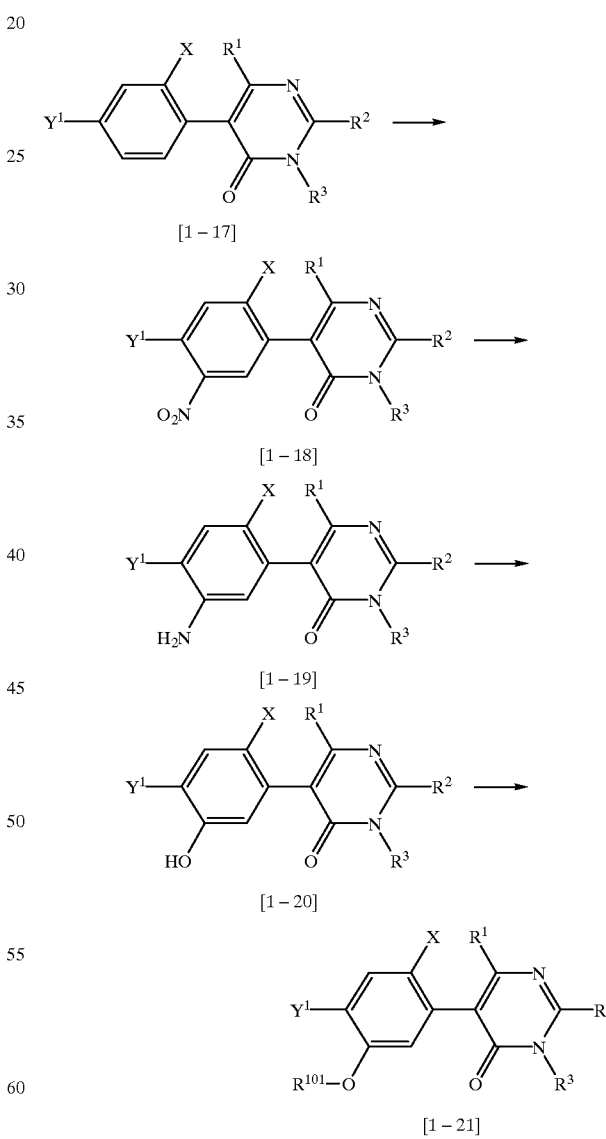

wherein $Y^1$ is a substituent other than nitro, which is included in the definition of Y; $R^{101}$ is a substituent other than hydrogen, which is included in the definition of $R^{10}$; and X, $R^1$, $R^2$, and $R^3$ are as defined above.

Process for Producing Compound [1-18] from compound [1-17]

Compound [1-18] can be produced by reacting compound [1-17] with a nitrating agent in a solvent.

Nitrating agent: nitric acid or the like
Amount of nitrating agent: 1 to 10 moles per mole of compound [1-17]
Solvent: sulfuric acid or the like
Temperature: −10° C. to room temperature
Time: a moment to 24 hours Process for Producing Compound [1-19] from Compound [1-18]

Compound [1-19] can be produced by reducing compound [1-18] with iron powder in the presence of an acid in a solvent.

Amount of iron powder: 3 moles to an excess per mole of compound [1-18]
Acid: acetic acid or the like
Amount of acid: 1 to 10 moles per mole of compound [1-18]
Solvent: water, ethyl acetate, or the like
Temperature: room temperature to refluxing temperature under heating
Time: a moment to 24 hours Process for Producing Compound [1-20] from Compound [1-19]

Compound [1-20] can be produced by 1) reacting compound [1-19] with a nitrite salt in a solvent, and then 2) heating it in an acid solution.

<Reaction 1>
Nitrite salt: sodium nitrite, potassium nitrite, or the like
Amount of nitrite salt: 1 to 2 moles per mole of compound [1-19]
Solvent: aqueous hydrochloric acid, aqueous sulfuric acid, or the like
Temperature: −10° to 10° C.
Time: a moment to 5 hours <Reaction 2>
Acidic solution: aqueous hydrochloric acid, aqueous sulfuric acid, or the like
Temperature: 70° C. to refluxing temperature under heating
Time: a moment to 24 hours Process for Producing Compound [1-21] from Compound [1-20]

Compound [1-21] can be produced by reacting compound [1-20] with a compound of the formula:

$$R^{101}\text{-D} \quad [11]$$

or $$(R^{101})_2 O \quad [12]$$

wherein $R^{101}$ and D are as defined above.

The reaction is usually effected in the presence of a base in a solvent. The reaction temperature is usually in the range of −20° to 150° C., preferably 0° to 50° C. The reaction time is usually in the range of a moment to 48 hours.

The amounts of the reagents to be used in the reaction are usually 1 to 3 moles of compound [11] or [12] and usually 1 to 5 moles of the base, per mole of compound [1-20].

Examples of the base which can be used include inorganic bases such as sodium hydride, potassium hydride, sodium hydroxide, potassium hydroxide, potassium carbonate, and sodium carbonate; and organic bases such as triethylamine, diisopropylethylamine, pyridine, 4-dimethylaminopyridine, N,N-dimethylaniline, and N,N-diethylaniline.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, tetrahydrofuran, and ethylene glycol dimethyl ether; nitro compounds such as nitrobenzene; acid amides such as formamide, N,N-dimethylformamide, and acetamide; tertiary amines such as pyridine, triethylamine, diisopropylethylamine, N,N-dimethylamine, N,N-diethylaniline, and N-methylmorpholine; ketones such as acetone and methyl isobutyl ketone; and mixtures thereof.

After completion of the reaction, the reaction mixture is poured into water, if necessary, and subjected to ordinary post-treatments such as extraction with an organic solvent and concentration, followed by, if necessary, subsequent purification by a technique such as column chromatography or recrystallization. Thus the present compound [1-21] can be obtained.

The above compound [1-20] can also be produced by the following process:

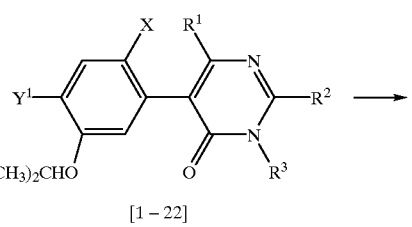

[1 − 22]

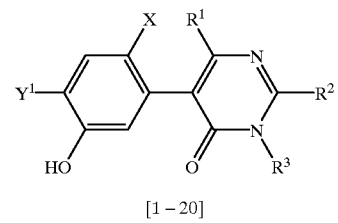

[1 − 20]

wherein X, $Y^1$, $R^1$, $R^2$ and $R^3$ are as defined above.

Process for Producing Compound [1-20] from Compound [1-22]

Compound [1-20] can be produced by deprotecting compound [1-22] in the presence of hydrogen bromide-acetic acid or sulfuric acid without any solvent or in a solvent Amount of hydrogen bromide-acetic acid or sulfuric acid: 1 mole to an excess per mole of compound [1-22]
Solvent: sulfuric acid, acetic acid, or the like
Temperature: 10° to 100° C.
Time: a moment to 24 hours

Production Process 6

This is the production process according to the following scheme:

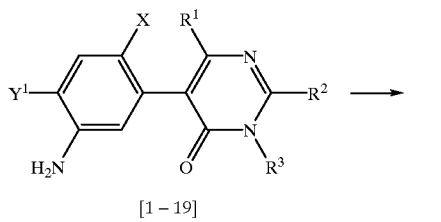

[1 – 19]

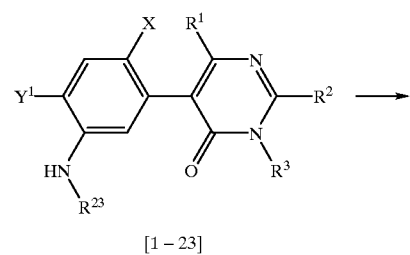

[1 – 23]

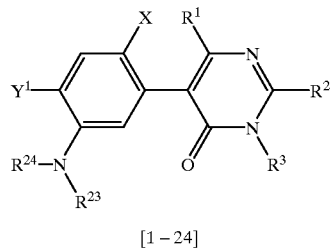

[1 – 24]

wherein $R^{23}$ and $R^{24}$ are independently a substituent included in the definition of $R^{11}$ or $R^{12}$; or —$COR^{13}$, —$SO_2R^{14}$, —$SO_2R^{15}$, or —$COOR^{13}$, wherein $R^{13}$, $R^{14}$, and $R^{15}$ are as defined above; X, $Y^1$, $R^1$, $R^2$, and $R^3$ are as defined above.

Process for Producing compound [1-23] from Compound [1-19]

Compound [1-23] can be produced by reacting compound [1-19] with a compound of the formula:

$$R^{23}\text{-D} \qquad [13]$$

or $$(R^{23})_2\text{O} \qquad [14]$$

wherein $R^{23}$ and D are as defined above, in the presence or absence of a base without any solvent or in a solvent.

- Amount of compound [13] or [14]: 1 mole to an excess per mole of compound [1-19]
- Base: organic bases such as pyridine and triethylamine; and inorganic bases such as potassium carbonate
- Amount of base: 1 to 3 moles per mole of compound [1-19]
- Solvent: N,N-dimethylformamide, 1,4-dioxane, or the like
- Temperature: 0° to 100° C.
- Time: a moment to 24 hours Process for Producing compound [1-24] from Compound 11-23]

Compound [1-24] can be produced by reacting compound [1-23] with a compound of the formula:

$$R^{24}\text{-D} \qquad [15]$$

or $$(R^{24})_2\text{O} \qquad [16]$$

wherein $R^{24}$ and D are as defined above, in the presence or absence of a base without any solvent or in a solvent.

- Amount of compound [15] or [16]: 1 mole to an excess per mole of compound [1-23]
- Base: organic bases such as pyridine and triethylamine; and inorganic bases such as potassium carbonate
- Amount of base: 1 to 3 moles per mole of compound [1-23]
- Solvent: N,N-dimethylformamide, 1,4-dioxane, or the like
- Temperature: 0° to 100° C.
- Time: a moment to 24 hours

Production Process 7

This is the production process according to the following scheme:

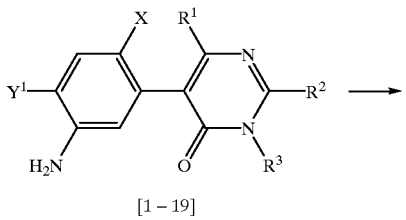

[1 – 19]

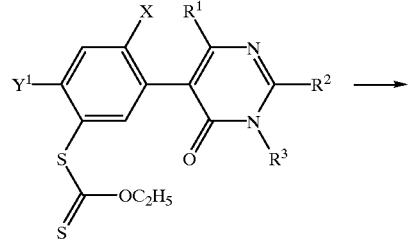

[1 – 25]

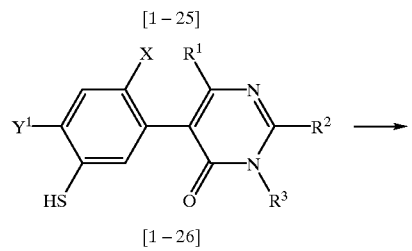

[1 – 26]

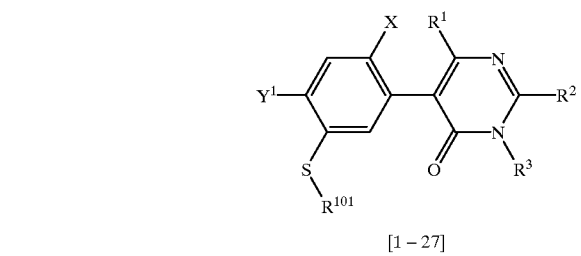

[1 – 27]

wherein X, $Y^1$, $R^1$, $R^2$, $R^3$, and $R^{101}$ are as defined above.

Process for Producing compound [1-25] from compound [1-19]

Compound [1-25] can be produced by 1) reacting compound [1-19] with a nitrite salt in a solvent, and then 2) reacting it with potassium xanthate in a solvent.

<Reaction 1)>

Nitrite salt: sodium nitrite, potassium nitrite, or the like

Amount of nitrite salt: 1 to 2 moles per mole of compound [1-19]

Solvent: aqueous hydrochloric acid, aqueous sulfuric acid, or the like

Temperature: −10° to 10° C.

Time: a moment to 5 hours

<Reaction 2)>

Amount of potassium xanthate: 1 to 2 moles per mole of compound [1-19]

Solvent: aqueous hydrochloric acid, aqueous sulfuric acid, or the like

Temperature: 0° to 110° C.

Time: a moment to 24 hours (see Org. Syn. Coll., Vol. 3, 809 (1955))

Process for Producing Compound [1-26] from Compound [1-25]

Compound [1-26] can be produced by hydrolyzing compound [1-25] in the presence of a base in a solvent.

Base: inorganic bases such as potassium carbonate

Amount of base: 1 to 5 moles per mole of compound [1-25]

Solvent: alcohols such as methanol and ethanol, or the like

Temperature: 0° C. to refluxing temperature under heating

Time: a moment to 24 hours (see Org. Syn. Coll., Vol. 3, 809 (1955))

Process for Producing Compound [1-27] from Compound [1-26]

Compound [1-27] can be produced by reacting compound [1-26] with compound [11] or [12] in the presence of a base in a solvent.

Amount of compound [11] or [12]: 1 mole to an excess per mole of compound [1-26]

Base: inorganic bases such as potassium carbonate; and organic bases such as triethylamine and pyridine Amount of base: 1 to 3 moles per mole of compound [1-26]

Solvent: 1,4-dioxane, N,N-dimethylformamide, or the like

Temperature: 0° to 100° C.

Time: a moment to 24 hours

Compound [1-26] can also be produced by the method according to the following scheme:

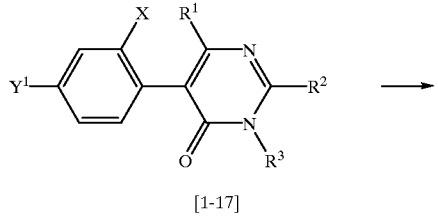

[1-17]

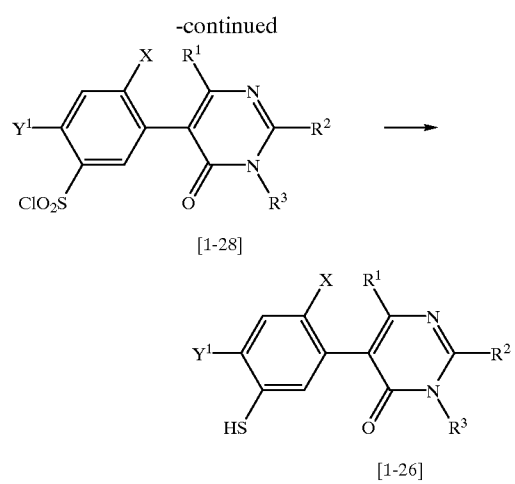

[1-28]

[1-26]

wherein X, $Y^1$, $R^1$, $R^2$, and $R^3$ are as defined above.

Process for Producing Compound [1-28] from Compound [1-17]

Compound [1-28] can be produced by reacting compound [1-17] with chlorosulfonic acid without any solvent or in a solvent.

Amount of chlorosulfonic acid: 1 mole to an excess per mole of compound [1-17]

Solvent: sulfuric acid

Temperature: 0° to 70° C.

Time: a moment to 24 hours (see Org. Syn. Coll., Vol. 1, 8 (1941))

Process for Producing Compound [1-26] from Compound [1-28]

Compound [1-26] can be produced by reducing compound [1-28] in a solvent.

Reducing agent: zinc, tin chloride, or the like

Amount of reducing agent: 3 moles to an excess per mole of compound [1-28]

Solvent: aqueous acetic acid, aqueous hydrochloric acid, aqueous sulfuric acid, or the like Temperature: room temperature to 100° C.

Time: a moment to 24 hours (see U.S. Pat. No. 4,709,049, column 9)

Production Process 8

This is the production process according to the following scheme:

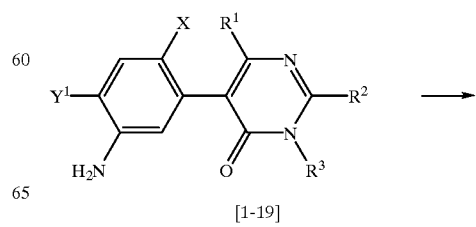

[1-19]

-continued

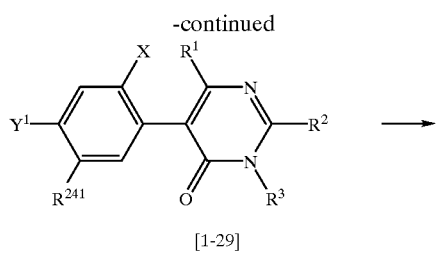

[1-29]

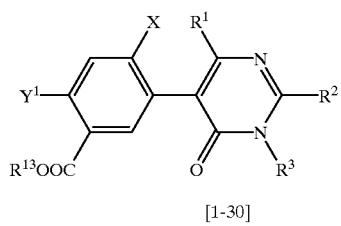

[1-30]

wherein $R^{241}$ is bromine or iodine; and X, $Y^1$, $R^1$, $R^2$, $R^3$, and $R^{13}$ are as defined above.

Process for Producing Compound [1-29] from Compound [1-19]

Compound [1-29] can be produced by 1) making a diazonium salt from compound [1-19] in a solvent, and then 2) reacting it with potassium iodide or copper (I) bromide in a solvent.

<Reaction 1)>

Diazotizing agent: sodium nitrite, potassium nitrite, or the like

Amount of diazotizing agent: 1 to 2 moles per mole of compound [1-19]

Solvent: aqueous hydrogen bromide, aqueous hydrogen chloride, aqueous sulfuric acid, or the like Temperature; −10° to 10° C.

Time: a moment to 5 hours

<Reaction 2)>

Amount of potassium iodide or copper (I) bromide: 1 mole to an excess per mole of compound [1-19]

Solvent: aqueous hydrogen bromide, water, or the like

Temperature: 0° to 80° C.

Time: a moment to 24 hours (see Org. Syn. Coll., Vol. 2, 604 (1943), and ibid., Vol. 1, 136 (1941))

Process for Producing Compound [1-30] from Compound [1-29]

Compound [1-30] can be produced by reacting compound [1-29] with a compound of the formula:

$R^{13}$-OH  [17]

wherein $R^{13}$ is as defined above, in the presence of a transition metal catalyst and a base in a solvent under an atmosphere of carbon monoxide.

Catalyst: $PdCl_2(PPh_3)_2$ or the like

Amount of catalyst: catalytic amount to 0.5 mole per mole of compound [1-29]

Amount of compound [17]: 1 mole to an excess per mole of compound [1-29]

Base: organic bases such as diethylamine

Amount of base: 1 to 10 moles per mole of compound [1-29]

Solvent: N,N-dimethylformamide or the like

Atmospheric pressure of carbon monoxide: 1 to 150 atm

Temperature: 0° to 100° C.

Time: a moment to 72 hours (see Bull. Chem. Soc. Jpn., 48 (7), 2075 (1975))

Production Process 9

The production process according to the following scheme:

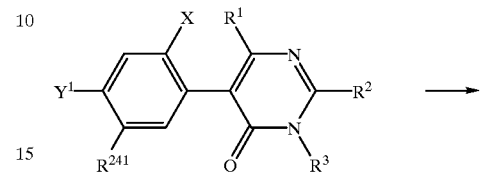

[1-29]

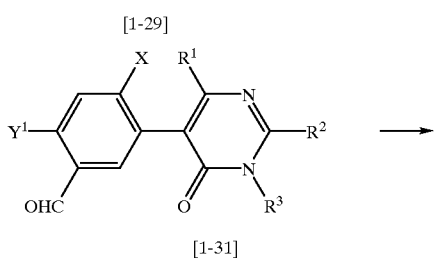

[1-31]

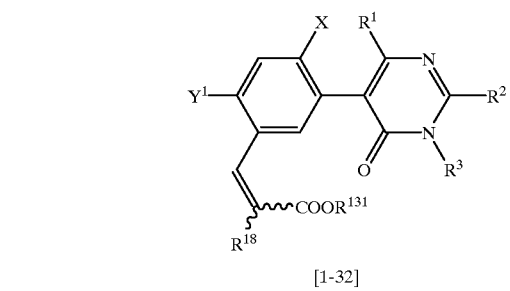

[1-32]

wherein $R^{131}$ is an substituent other than hydrogen, which is included in the definition of $R^{13}$; and X, $Y^1$, $R^1$, $R^2$, $R^3$, and $R^{18}$ are as defined above.

Process for Producing Compound [1-31] from Compound [1-29]

Compound [1-31] can be produced by reacting compound [1-29] with sodium formate or potassium formate in the presence of a transition metal catalyst in a solvent under an atmosphere of carbon monoxide.

Amount of sodium formate or potassium formate: 1 mole to an excess per mole of compound [1-29]

Solvent: N,N-dimethylformamide or the like

Catalyst: $PdCl_2(PPh_3)_2$ or the like

Amount of catalyst: catalytic amount to 0.5 mole per mole of compound [1-29]

Atmospheric pressure of carbon monoxide: 1 atm

Temperature: 0° to 100° C.

Time: a moment to 72 hours (see Bull. Chem. Soc. Jpn., 67, 2329 (1994))

Process for producing compound [1-32] from compound [1-31]

Compound [1-32] can be produced by reacting compound [1-31] with a compound of the formula:

$(C_6H_5)_3P=CR^{18}COOR^{131}$  [18]

or $(C_2H_5O)_2P(O)CHR^{18}COOR^{131}$  [19]

wherein $R^{18}$ and $R^{131}$ are as defined above, in a solvent, and if compound [19] is used, in the presence of a base.

Amount of compound [18] or [19]: 1 to 5 moles per mole of compound [1-31]

Solvent: tetrahydrofuran, toluene, or the like

Base: sodium hydride or the like

Amount of base: 1 to 5 moles per mole of compound [1-31]

Temperature: 0° to 50° C.

Time: a moment to 24 hours

Production Process 10

This is the production process according to the following scheme:

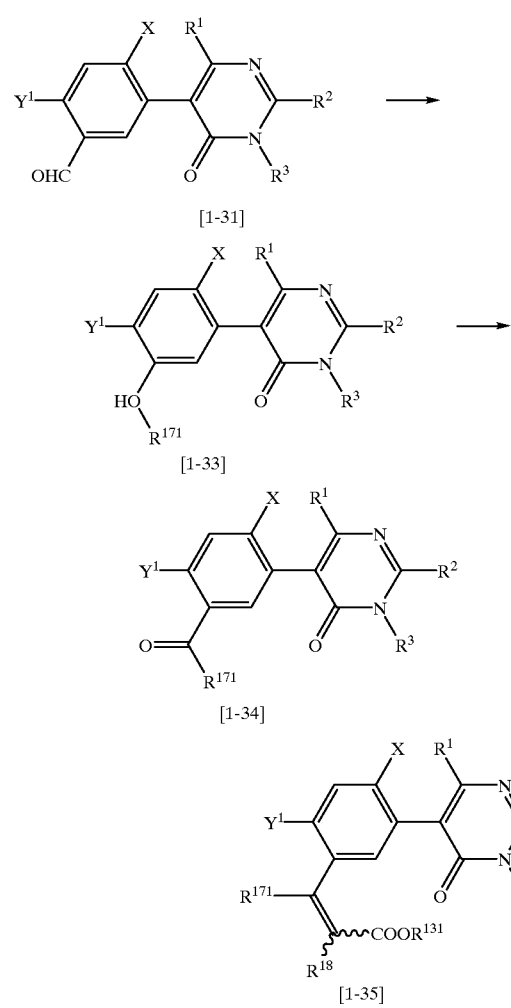

wherein $R^{171}$ is $C_1$–$C_6$ alkyl; and X, $Y^1$, $R^1$, $R^2$, $R^3$, $R^{18}$, and $R^{131}$ are as defined above.

Process for Producing Compound [1-33] from compound [1-31]

Compound [1-33] can be produced by reacting compound [1-31] with a compound of the formula:

$$R^{171}\text{-MgBr} \quad [20]$$

or $$R^{171}\text{-Li} \quad [21]$$

wherein $R^{171}$ is as defined above, in a solvent.

Amount of compound [20] or [21]: 1 to 2 moles per mole of compound [1-31]

Solvent: ether solvents such as tetrahydrofuran

Temperature: −78° C. to room temperature

Time: a moment to 24 hours

Process for Producing Compound [1-34] from Compound [1-33]

Compound [1-34] can be produced by subjecting compound [1-33] to oxidative treatment using chromium (VI) oxide-sulfuric acid, pyridinium chlorochromate, or the like; oxidation using dimethylsulfoxide-acetic anhydride; or Swern oxidation.

Process for producing compound [1-35] from compound [1-34]

Compound [1-35] can be produced by reacting compound [1-34] with a compound of the formula:

$$(C_6H_5)_3P{=}CR^{18}COOR^{131} \quad [18]$$

or $$(C_2H_5O)_2P(O)CHR^{18}COOR^{131} \quad [19]$$

wherein $R^{18}$ and $R^{131}$ are as defined above, in a solvent, and if compound [19] is used, in the presence of a base.

Amount of compound [18] or [19]: 1 to 5 moles per mole of compound [1-34]

Solvent: tetrahydrofuran, toluene, or the like

Base: sodium hydride or the like

Amount of base: 1 to 5 moles per mole of compound [1-34]

Temperature: 0° to 50° C.

Time: a moment to 24 hours

Production Process 11

This is the production process according to the following scheme:

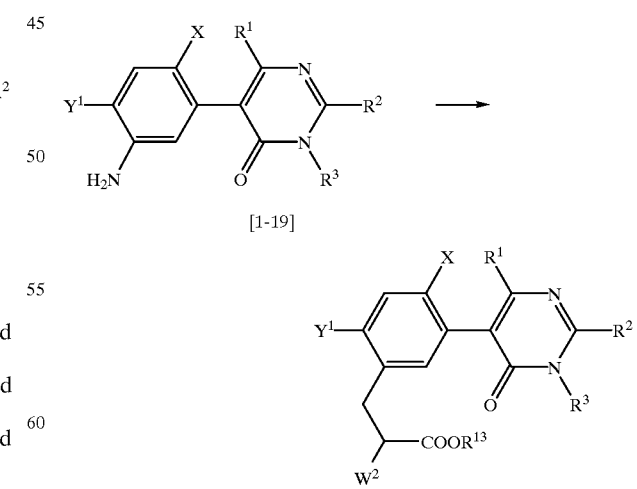

wherein $W^2$ is chlorine or bromine; and X, $Y^1$, $R^1$, $R^2$, $R^3$, and $R^{13}$ are as defined above.

Compound [1-36] can be produced by reacting compound [1-19] with t-butyl nitrite or t-amyl nitrite; a compound of the formula:

$$CuW^2{}_2 \quad [22]$$

wherein $W^2$ is as defined above; and a compound of the formula:

$$CH_2=CHCOOR^{13} \quad [23]$$

wherein $R^{13}$ is as defined above, in a solvent.

Amount of t-butyl nitrite or t-amyl nitrite: 1 to 2 moles per mole of compound [1-19]
Amount of compound [22]: 1 to 2 moles per mole of compound [1-19]
Amount of compound [23]: 10 moles to an excess per mole of compound [1-19]
Solvent: acetonitrile or the like
Temperature: 0° to 50° C.
Time: a moment to 24 hours
(see EP 0 649 596, page 11)

Production Process 12

This is the production process according to the following scheme:

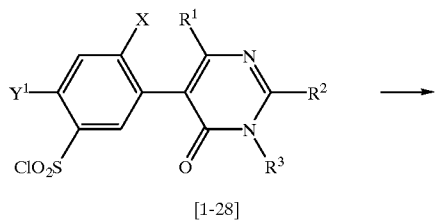

wherein $X$, $Y^1$, $R^1$, $R^2$, $R^3$, and $R^{10}$ are as defined above.

Compound [1-37] can be produced by reacting compound [1-28] with a compound of the formula:

$$R^{10}\text{-OH} \quad [24]$$

wherein $R^{10}$ is as defined above, in the presence of a base without any solvent or in a solvent.

Amount of compound [24]: 1 mole to an excess per mole of compound [1-28]
Base: organic bases such as triethylamine; and inorganic bases such as potassium carbonate
Amount of base: 1 to 3 moles per mole of compound [1-28]
Solvent: N,N-dimethylformamide, 1,4-dioxane, or the like
Temperature: 0° to 100° C.
Time: a moment to 24 hours Production Process 13

This is the production process according to the following scheme:

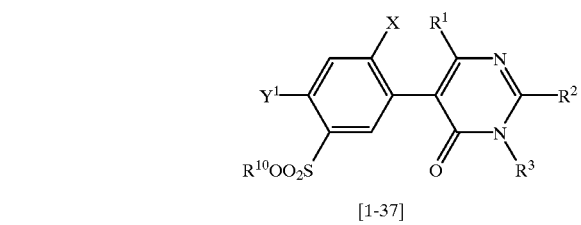

wherein $X$, $Y^1$, $R^1$, $R^2$, $R^3$, $R^{11}$, and $R^{12}$ are as defined above.

Compound [1-38] can be produced by reacting compound [1-28] with a compound of the formula:

$$R^{11}(R^{12})NH \quad [25]$$

wherein $R^{11}$ and $R^{12}$ are as defined above, in the presence or absence of a base without any solvent or in a solvent.

Amount of compound [25]: 1 mole to an excess per mole of compound [1-28]
Base: organic bases such as triethylamine; and inorganic bases such as potassium carbonate
Amount of base: 1 to 3 moles per mole of compound [1-28]
Solvent: N,N-dimethylformamide, 1,4-dioxane, or the like
Temperature: 0° to 100° C.
Time: a moment to 24 hours Production Process 14

This is the production process according to the following scheme:

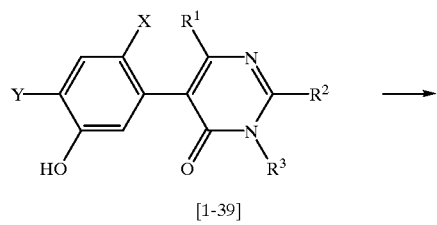

-continued

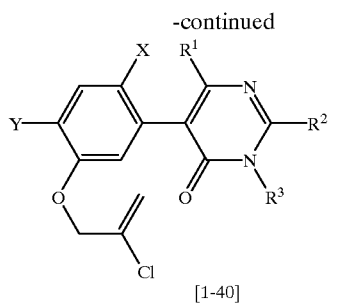

[1-40]

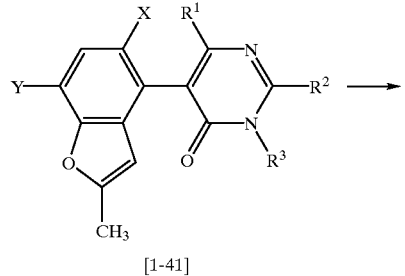

[1-41]

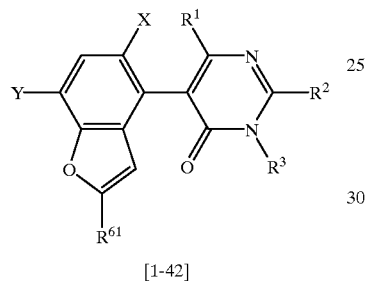

[1-42]

wherein $R^{61}$ is a substituent other than methyl, which is included in the definition of $R^6$; and X, Y, $R^1$, $R^2$, and $R^3$ are as defined above.

Process for Producing Compound [1-40] from compound [1-39]

Compound [1-40] can be produced by reacting compound [1-39] with 2,3-dichloropropene in the presence of a base in a solvent.

Amount of 2,3-dichloropropene: 1 to 3 moles per mole of compound [1-39]

Base: inorganic bases such as potassium carbonate

Amount of base: 1 to 5 moles per mole of compound [1-39]

Solvent: N,N-dimethylformamide or the like

Temperature: 0° to 100° C.

Time: a moment to 24 hours

Process for Producing Compound [1-41] from Compound [1-40]

Compound [1-41] can be produced by heating compound [1-40] in a solvent.

Solvent: N,N-dimethylformamide, N,N-dimethylaniline, N,N-diethylaniline, m-diisopropylbenzene, or the like Temperature: 70° to 200° C.

Time: a moment to 24 hours

Process for Producing Compound [1-42] from Compound [1-41]

Compound [1-42] can be produced from compound [1-41] according to the method in which the methyl group in position 2 on the benzofuran ring is replaced with another substituent, as described in U.S. Pat. No. 5,308,829, columns 2–11.

Production Process 15

This is the production process according to the following scheme:

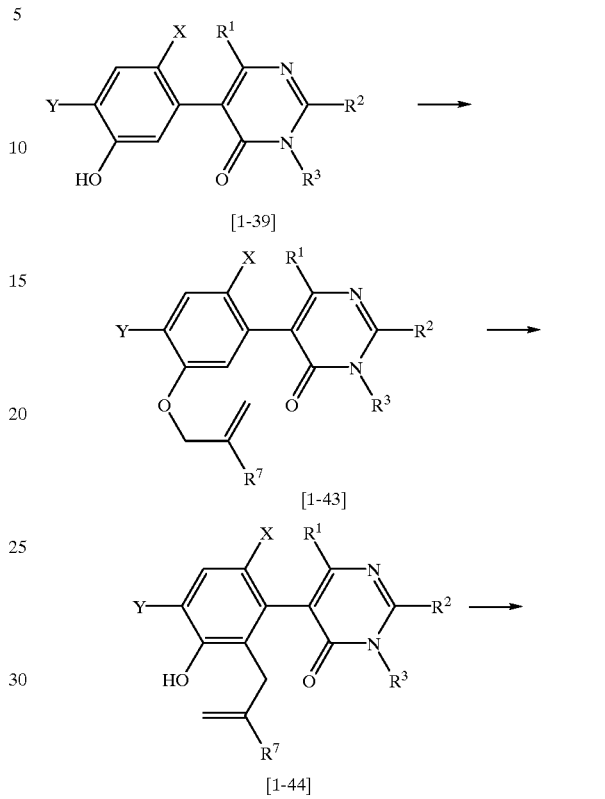

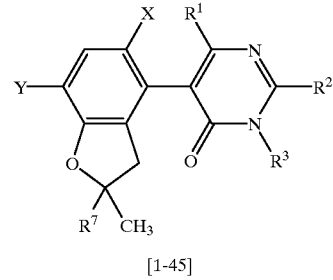

wherein X, Y, $R^1$, $R^2$, $R^3$, and $R^7$ are as defined above.

Process for Producing Compound [1-43] from compound [1-39]

Compound [1-43] can be produced by reacting compound [1-39] with a compound of the formula:

$$CH_2=CR^7CH_2W^2 \qquad [26]$$

wherein $W^2$ and $R^7$ are as defined above, in the presence of a base in a solvent.

Amount of compound [26]: 1 to 5 moles per mole of compound [1-39]

Base: inorganic bases such as potassium carbonate

Amount of base: 1 to 5 moles per mole of compound [1-39]

Solvent: N,N-dimethylformamide, 1,4-dioxane, or the like

Temperature: 0° to 100° C.

Time: a moment to 24 hours

Process for Producing Compound [1-44] from Compound [1-43]

Compound [1-44] can be produced by heating compound [1-43] in a solvent.

Solvent: N,N-dimethylaniline, N,N-diethylaniline, m-diisopropylbenzene, or the like
Temperature: 100° to 200° C.
Time: a moment to 24 hours Process for Producing Compound [1-45] from Compound [1-44]

Compound [1-45] can be produced by heating compound [1-44] in the presence of an acid in a solvent.

Acid: organic acids such as p-toluenesulfonic acid; and inorganic acids such as sulfuric acid
Amount of acid: catalytic amount to 1 mole per mole of compound [1-44]
Solvent: toluene, xylene, or the like
Temperature: 100° to 250° C.
Time: a moment to 24 hours Production Process 16

This is the production process according to the following scheme:

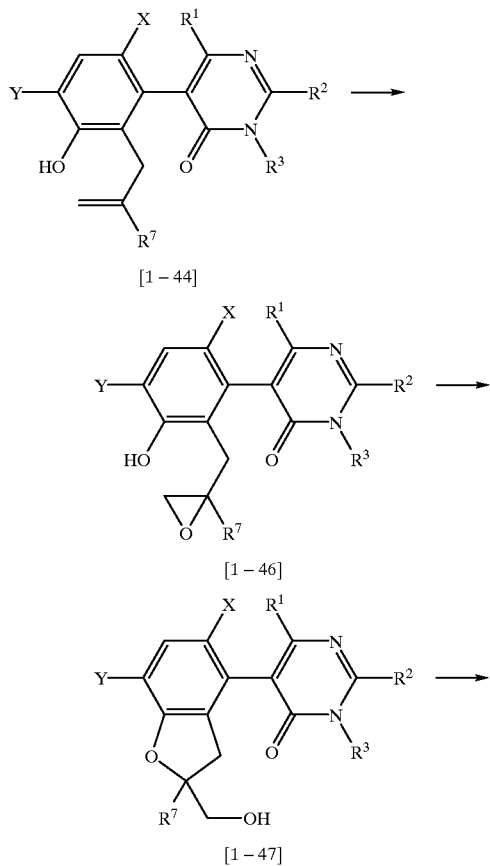

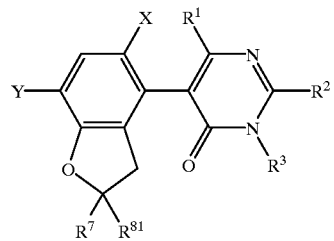

wherein $R^{81}$ is a substituent other than methyl and hydroxymethyl, which is included in the definition of $R^8$; and X, Y, $R^1$, $R^2$, $R^3$, and $R^7$ are as defined above.

Process for Producing Compound [1-46] from Compound [1-44]

Compound [1-46] can be produced by reacting compound [1-44] with a peracid in a solvent.

Peracid: m-chloroperbenzoic acid, peracetic acid, or the like
Amount of peracid: 1 mole to an excess per mole of compound [1-44]
Solvent: halogenated hydrocarbons such as dichloromethane; or organic acids such as acetic acid
Temperature: −20° C. to room temperature
Time: a moment to 24 hours Process for Producing Compound [1-47] from Compound [1-46]

Compound [1-47] can be produced by reacting compound [1-46] in the presence of a base in a solvent.

Base: potassium carbonate or the like
Amount of base: 1 to 2 moles per mole of compound [1-46]
Solvent: methanol, ethanol, or the like
Temperature: 0° to 50° C.
Time: a moment to 5 hours Process for Producing Compound [1-48] from Compound [1-47]

Compound [1-48] can be produced from compound [1-47] according to the method in which the hydroxyalkyl group in position 2 on the dihydrobenzofuran ring is replaced with another substituent, as described in U.S. Pat. No. 5,411,935, columns 5–10.

Compound [2], which is an intermediate compound for the production of the present compounds, can be produced with high efficiency by reacting compound [5] with compound [6] (hereinafter referred to as intermediate production process 1).

The reaction is effected without any solvent or in a solvent. The reaction temperature is usually in the range of −20° to 150° C., preferably 0° to 50° C. The reaction time is usually in the range of a moment to 240 hours.

The amounts of the reagents to be used in the reaction, although the proportion of 1 mole of compound [6] to 1 mole of compound [5] is ideal, can be freely changed depending upon the reaction conditions.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chloroform, carbon tetrachloride, dichloromethane, dichloroethane, chlorobenzene, and dichlorobenzene; ethers such as diethyl ether, diisopropyl ether, dioxane, tetrahydrofuran, and ethylene glycol dimethyl ether; nitro compounds such as nitromethane and nitrobenzene; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; and mixtures thereof.

After completion of the reaction, the reaction mixture is poured into water, if necessary, and subjected to ordinary post-treatments such as extraction with an organic solvent and concentration, or purified by a technique such as column chromatography or recrystallization. Thus the desired compound can be isolated.

In the intermediate production process 1, compound [6] can be replaced with a salt of compound [6] with an organic or inorganic acid (e.g., acetamidine hydrochloride). The reaction is usually effected in the presence of a base in a solvent. The reaction temperature is usually in the range of −20° to 150° C., preferably 0° to 50° C. The reaction time is usually in the range of a moment to 240 hours.

The amounts of the compounds to be used in the reaction, although the proportion of 1 mole of compound [6] to 1 mole of compound [5] is ideal, can be freely changed depending upon the reaction conditions. The amount of the base is usually 1 mole to a large excess per mole of the salt of compound [6].

Examples of the base which can be used include inorganic bases such as sodium hydride, potassium hydride, sodium hydroxide, potassium hydroxide, potassium carbonate, and sodium carbonate; and organic bases such as triethylamine, diisopropylethylamine, pyridine, 4-dimethylaminopyridine, N,N-dimethylaniline, and N,N-diethylaniline.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chloroform, carbon tetrachloride, dichloromethane, dichloroethane, chlorobenzene, and dichlorobenzene; ethers such as diethyl ether, diisopropyl ether, dioxane, tetrahydrofuran, and ethylene glycol dimethyl ether; nitro compounds such as nitromethane and nitrobenzene; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; and mixtures thereof.

After completion of the reaction, the reaction mixture is poured into water and the precipitated crystals are collected by filtration, or the reaction mixture is subjected to ordinary post-treatments such as extraction with an organic solvent and concentration, followed by, if necessary, subsequent purification by a technique such as chromatography or recrystallization. Thus the desired compound can be isolated.

Compound [2] can also be produced by reacting a compound of the formula:

$$\underset{\text{COOR}^{19}}{\overset{R^1}{\underset{Q}{\diagdown}}}\!\!=\!\!O \qquad [27]$$

wherein Q, $R^1$, and $R^{19}$ are as defined above, with compound [6] (hereinafter referred to as intermediate production process 2).

The reaction is effected without any solvent or in a solvent. The reaction temperature is usually in the range of −20° to 150° C., preferably 0° to 50° C. The reaction time is usually in the range of a moment to 48 hours.

The amounts of the reagents to be used in the reaction, although the proportion of 1 mole of compound [6] to 1 mole of compound [27] is ideal, can be freely changed depending upon the reaction conditions.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chloroform, carbon tetrachloride, dichloromethane, dichloroethane, chlorobenzene, and dichlorobenzene; ethers such as diethyl ether, diisopropyl ether, dioxane, tetrahydrofuran, and ethylene glycol dimethyl ether; nitro compounds such as nitromethane and nitrobenzene; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; and mixtures thereof.

After completion of the reaction, the reaction mixture is poured into water, if necessary, and subjected to ordinary post-treatments such as extraction with an organic solvent and concentration, or under certain circumstances, the reaction mixture is purified by a technique such as chromatography or recrystallization. Thus the desired compound can be isolated.

In the intermediate production process 2, compound [6] can be replaced with a salt of compound [6] with an organic or inorganic acid (e.g., acetamidine hydrochloride). The reaction is usually effected in the presence of a base in a solvent. The reaction temperature is usually in the range of −20° to 150° C., preferably 0° to 50° C. The reaction time is usually in the range of a moment to 72 hours.

The amounts of the compounds to be used in the reaction, although the proportion of 1 mole of compound [6] to 1 mole of compound [27] is ideal, can be freely changed depending upon the reaction conditions. The amount of the base is usually 1 mole to a large excess per mole of the salt of compound [6].

Examples of the base which can be used include inorganic bases such as sodium hydroxide, potassium hydroxide, potassium carbonate, and sodium carbonate; and organic bases such as triethylamine, diisopropylethylamine, pyridine, 4-dimethylaminopyridine, N,N-dimethylaniline, and N,N-diethylaniline.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chloroform, carbon tetrachloride, dichloromethane, dichloroethane, chlorobenzene, and dichlorobenzene; ethers such as diethyl ether, diisopropyl ether, dioxane, tetrahydrofuran, and ethylene glycol dimethyl ether; nitro compounds such as nitromethane and nitrobenzene; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; and mixtures thereof.

After completion of the reaction, the reaction mixture is poured into water and the precipitated crystals are collected by filtration, or the reaction mixture is subjected to ordinary post-treatments such as extraction with an organic solvent and concentration, followed by, if necessary, subsequent purification by a technique such as chromatography or recrystallization. Thus the desired compound can be isolated.

Compound [6] can be obtained from commercial sources or can be produced by the method as described in J. Am. Chem. Soc., 78, 6032 (1956).

Compound [5] can be produced, for example, by any of the following methods 1 to 4.

(Method 1) (For compounds wherein $R^1$ is hydrogen)

In this method, compound [27] wherein $R^1$ is hydrogen is reacted with a compound of the formula:

$$R^{20}\text{-D} \quad [28]$$

wherein $R^{20}$ and D are as defined above.

The reaction can be effected in the presence of a base in a solvent. The reaction temperature is usually in the range of 0° to 100° C. The reaction time is usually in the range of a moment to 48 hours.

Examples of the base which can be used include inorganic bases such as potassium carbonate, sodium carbonate, potassium hydroxide, sodium hydroxide, and sodium hydride.

Compound [28] includes methyl iodide, methyl bromide, ethyl iodide, ethyl bromide, and isopropyl iodide.

The amounts of the reagents to be used in the reaction are usually 1 mole to a large excess of the base and usually 1 to 5 moles of compound [28], per mole of compound [27].

Examples of the solvent which can be used include aliphatic hydrocarbons such as hexane, heptane, ligroin, cyclohexane, and petroleum ether; aromatic hydrocarbons such as benzene, toluene, and xylene; ethers such as diethyl ether, diisopropyl ether, dioxane, tetrahydrofuran, and ethylene glycol dimethyl ether; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; and mixtures thereof.

After completion of the reaction, the reaction mixture is poured into water and the precipitated crystals are collected by filtration, or the reaction mixture is subjected to ordinary post-treatments such as extraction with an organic solvent and concentration, followed by, if necessary, subsequent purification by a technique such as chromatography or recrystallization. Thus the desired compound can be isolated.

(Method 2) (For compounds wherein $R^1$ is any other than hydrogen)

In this method, compound [27] wherein $R^1$ is $C_1$–$C_3$ alkyl is reacted with a compound of the formula:

$$HC(OR^{20})_3 \quad [29]$$

wherein $R^{20}$ is as defined above, in the presence of an acid catalyst (e.g., p-toluenesulfonic acid).

(Method 3)

This is the production process according to the following scheme:

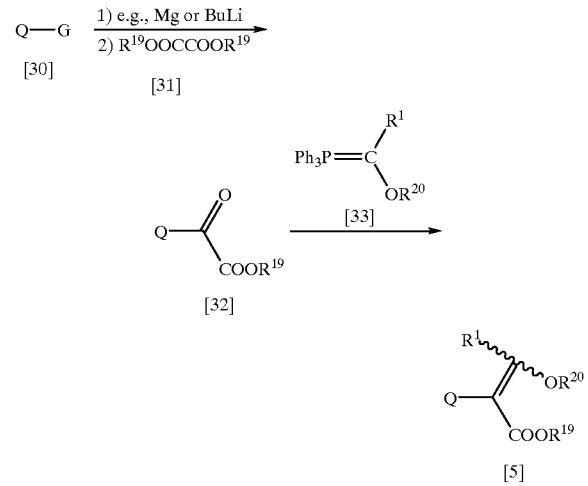

wherein Q, $R^1$, $R^{19}$, and $R^{20}$ are as defined above; and G is chlorine, bromine, or iodine.

The reaction conditions in the respective steps are described, for example, in JP-A 61-106538/1986.

(Method 4)

This is the production process according to the following scheme:

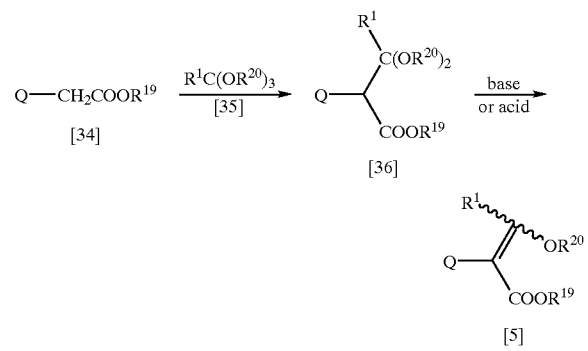

wherein Q, $R^1$, $R^{19}$, and $R^{20}$ are as defined above.

The reaction conditions in the respective steps are described, for example, in JP-A 61-106538/1986.

Compound [27] can be obtained by reacting a compound of the formula:

$$QCH_2COOR^{19} \quad [34]$$

wherein Q and $R^{19}$ are as defined above, with a compound of the formula:

$$R^1COOR^{22} \quad [37]$$

wherein $R^1$ and $R^{22}$ are as defined above, in the presence of an appropriate base.

The reaction is usually effected in a solvent. The reaction temperature is usually in the range of −20° to 150° C. The reaction time is usually in the range of a moment to 72 hours.

The amounts of the compounds to be used in the reaction are usually 1 to 10 moles of compound [37] and usually 1 to 20 moles of the base, per mole of compound [34].

Examples of the base which can be used include inorganic bases such as sodium hydride and potassium hydride.

Examples of the solvent which can be used include aliphatic hydrocarbons such as hexane, heptane, ligroin, cyclohexane, and petroleum ether; aromatic hydrocarbons such as benzene, toluene, and xylene; ethers such as diethyl ether, diisopropyl ether, dioxane, tetrahydrofuran, and ethylene glycol dimethyl ether; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; and mixtures thereof.

After completion of the reaction, the reaction mixture is poured into water and made acidic by the addition of a mineral acid such as hydrochloric acid or sulfuric acid, followed by ordinary post-treatments such as extraction with an organic solvent and concentration, and if necessary, subsequent purification by a technique such as chromatography or recrystallization. Thus the desired product can be isolated.

Compound [34] is commercially available, or when the corresponding phenylacetic acid (i.e., $QCH_2COOH$) is commercially available, compound [34] can be produced by esterifying this phenylacetic acid according to the ordinary method. However, when neither compound [34] nor the corresponding phenylacetic acid is commercially available, they can be produced, for example, by the following scheme:

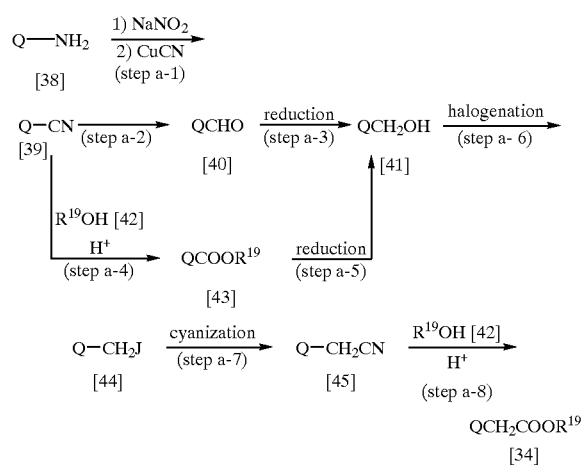

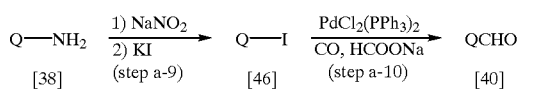

wherein Q and $R^{19}$ are as defined above, and J is chlorine or bromine.

Compound [40] can also be produced by the following scheme:

wherein Ph is a phenyl group and Q is as defined above.

(Step a-1) can be conducted according to the method as described in Organic Synthesis Collective Volume, 1, 514 (1941);

(Step a-2), Jikken Kagaku Koza (4th ed.) 21, edited by the Chemical Society of Japan, Maruzen K.K., pp. 89–97;

(Step a-3), Jikken Kagaku Koza (4th ed.) 20, edited by the Chemical Society of Japan, Maruzen K.K., pp. 1–10;

(Step a-4) and (Step a-8), Organic Synthesis Collective Volume, 1, 131 (1941);

(Step a-5), Jikken Kagaku Koza (4th ed.) 20, edited by the Chemical Society of Japan, Maruzen K.K., pp. 10–14;

(Step a-6), Organic Synthesis Collective Volume, 3, 370 (1955) or Organic Synthesis Collective Volume, 6, 634 (1988);

(Step a-7), Organic Synthesis Collective Volume, 1, 107 (1941);

(Step a-9), Organic Synthesis Collective Volume, 2, 351 (1943); and (Step a-10), Bull. Chem. Soc. Jpn., 67, 2329 (1994).

Compound [38] is known in, or can be produced according to the method as described in, EP-61741-A; U.S. Pat. No. 4,670,046, U.S. Pat. No. 4,770,695, U.S. Pat. No. 4,709,049, U.S. Pat. No. 4,640,707, U.S. Pat. No. 4,720,927, U.S. Pat. No. 5,169,431; and JP-A 63-156787/1988.

Some examples of compound [38] can also be produced according to the following scheme:

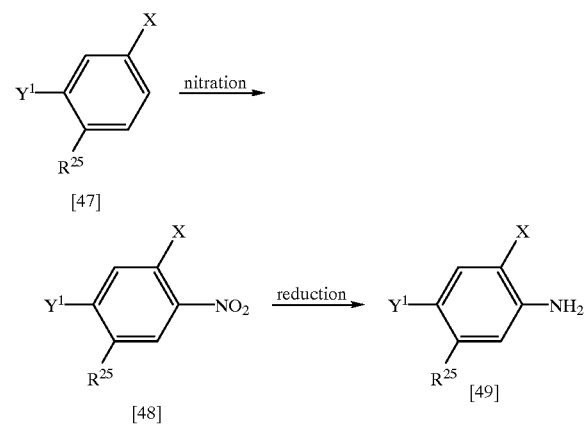

wherein $R^{25}$ is $-COR^{26}$ or $-COOR^{13}$, $R^{26}$ is hydrogen or $C_1$–$C_6$ alkyl, and X and $Y^1$ are as defined above.

The present compounds have excellent herbicidal activity, and some of them exhibit excellent selectivity between crop plants and unfavorable weeds. In particular, the present compounds have herbicidal activity against various unfavorable weeds as recited below, which may cause trouble in the foliar treatment and soil treatment on upland fields.

Polygonaceae:
  wild buckwheat (*Polygonum convolvulus*), pale smartweed (*Polygonum lapathifolium*), Pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)

Portulacaceae:
  common purslane (*Portulaca oleracea*)

Caryophyllaceae:
  common chickweed (*Stellaria media*)

Chenopodiaceae:
  common lambsquarters (*Chenopodium album*), kochia (*Kochia scoparia*)

Amaranthaceae:
  redroot pigweed (*Amaranthus retroflexus*), smooth pigweed (*Amaranthus hybridus*)

Cruciferae:
  wild radish (*Raphanus raphanistrum*), wild mustard (*Sinapis arvensis*), shepherdspurse (*Capsella bursa-pastoris*)

Leguminosae:
  hemp sesbania (*Sesbania exaltata*), sicklepod (*Cassia obtusifolia*), Florida beggarweed (*Desmodium tortuosum*), white clover (*Trifolium repens*)
Malvaceae:
  velvetleaf (*Abutilon theophrasti*), prickly sida (*Sida spinosa*)
Violaceae:
  field pansy (*Viola arvensis*), wild pansy (*Viola tricolor*)
Rubiaceae:
  catchweed bedstraw (cleavers) (*Galium aparine*)
Convolvulaceae:
  ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)
Labiatae:
  red deadnettle (*Lamium purpureum*), henbit (*Lamium amplexicaule*)
Solanaceae:
  jimsonweed (*Datura stramonium*), black nightshade (*Solanum nigrum*)
Scrophulariaceae:
  birdseye speedwell (*Veronica persica*), ivyleaf speedwell (*Veronica hederaefolia*)
Compositae:
  common cocklebur (*Xanthium pensylvanicum*), common sunflower (*Helianthus annuius*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)
Boraginaceae:
  field forget-me-not (*Myosotis arvensis*)
Asclepiadaceae:
  common milkweed (*Asclepias syriaca*)
Euphorbiaceae:
  sun spurge (*Euphorbia helioscopia*), spotted spurge (*Euphorbia maculata*)
Gramineae:
  barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oat (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)
Commelinaceae:
  common dayflower (*Commelina communis*)
Equisetaceae:
  field horsetail (*Equisetum arvense*)
Cyperaceae:
  rice flatsedge (*Cyperus iria*), purple nutsedge (*Cyperus rotundus*), yellow nutsedge (*Cyperus esculentus*)

Furthermore, some of the present compounds have no problematic phytotoxicity on main crops such as corn (*Zea mays*), wheat (*Triticum aestivum*), barley (*Hordeum vulgare*), rice (*Oryza sativa*), sorghum (*Sorghum bicolor*), soybean (*Glycine max*), cotton (Gossypium spp.), sugar beet (*Beta vulgaris*), peanut (*Arachis hypogaea*), sunflower (*Helianthus annuus*) and canola (*Brassica napus*); garden crops such as flowers and ornamental plants; and vegetable crops.

The present compounds can attain effective control of unfavorable weeds in the no-tillage cultivation of soybean (*Glycine max*), corn (*Zea mays*), and wheat (*Triticum aestivum*). Furthermore, some of them exhibit no problematic phytotoxicity on crop plants.

The present compounds have herbicidal activity against various unfavorable weeds as recited below under the flooding treatment on paddy fields.
Gramineae:
  barnyardgrass (*Echinochloa oryzicola*)
Scrophulariaceae:
  common falsepimpemel (*Lindernia procumbens*)
Lythraceae:
  *Rotala indica, Ammannia multiflora*
Elatinaceae:
  *Elatine triandra*
Cyperaceae:
  smallflower umbrellaplant (*Cyperus difformis*), hardstem bulrush (*Scirpus juncoides*), needle spikerush (*Eleocharis acicularis*), *Cyperus serotinus, Eleocharis kuroguwai*
Pontederiaceae:
  *Monochoria vaginalis*
Aismataceae:
  *Sagittaria pygmaea, Sagittaria trifolia, Alisma canaliculatum*
Potamogetonaceae:
  roundleaf pondweed (*Potamogeton distinctus*)
Umbelliferae:
  *Oenanthe javanica*

Furthermore, some of the present compounds have no problematic phytotoxicity on transplanted paddy rice.

The present compounds can attain effective control of various unfavorable weeds in orchards, grasslands, lawns, forests, waterways, canals, or other non-cultivated lands.

The present compounds also have herbicidal activity against various aquatic plants such as water hyacinth (*Eichhornia crassipes*), which will grow in waterways, canals, or the like.

The present compounds have substantially the same characteristics as those of the herbicidal compounds described in the publication of International Patent Application WO95/34659. In the case where crop plants with tolerance imparted by introducing a herbicide tolerance gene described in the publication are cultivated, the present compounds can be used at greater doses than those used when ordinary crop plants without tolerance are cultivated, and it is, therefore, possible to attain effective control of other unfavorable plants.

When the present compounds are used as active ingredients of herbicides, they are usually mixed with solid or liquid carriers or diluents, surfactants, and other auxiliary agents to give formulations such as emulsifiable concentrates, wettable powders, flowables, granules, concentrated emulsions, and water-dispersible granules.

These formulations may contain any of the present compounds as an active ingredient at an amount of 0.001% to 80% by weight, preferably 0.005% to 70% by weight, based on the total weight of the formulation.

Examples of the solid carrier or diluent may include fine powders or granules of the following materials: mineral matters such as kaolin clay, attapulgite clay, bentonite, terra alba, pyrophyllite, talc, diatomaceous earth, and calcite; organic substances such as walnut shell powder; water-soluble organic substances such as urea; inorganic salts such as ammonium sulfate; and synthetic hydrated silicon oxide. Examples of the liquid carrier or diluent may include aromatic hydrocarbons such as methylnaphthalene, phenylxylylethane, and alkylbenzenes (e.g., xylene); alcohols such as isopropanol, ethylene glycol, and 2-ethoxyethanol; esters such as phthalic acid dialkyl esters; ketones such as acetone, cyclohexanone, and isophorone; mineral oils such as machine oil; vegetable oils such as soybean oil and cotton seed oil; dimethylsulfoxide, N,N-dimethylformamide, acetonitrile, N-methylpyrrolidone, water, and the like.

Examples of the surfactant used for emulsification, dispersing, or spreading may include surfactants of the anionic type, such as alkylsulfates, alkylsulfonates, alkylarylsulfonates, dialkylsulfosuccinates, and phosphates of polyoxyethylene alkyl aryl ethers; and surfactants of the nonionic type, such as polyoxyethylene alkyl ethers, polyoxyethylene alkyl aryl ethers, polyoxyethylene polyoxypropylene block copolymers, sorbitan fatty acid esters, and polyoxyethylene sorbitan fatty acid esters.

Examples of the auxiliary agent used for formulation may include ligninsulfonates, alginates, polyvinyl alcohol, gum arabic, carboxymethyl cellulose (CMC), and isopropyl acid phosphate (PAP).

The present compounds are usually formulated as described above and then used for the pre- or post-emergence soil, foliar, or flooding treatment of unfavorable weeds. The soil treatment may include soil surface treatment and soil incorporation. The foliar treatment may include application over the plants and directed application in which a chemical is applied only to the unfavorable weeds so as to keep off the crop plants.

The present compounds can be used, if necessary, in combination with other compounds having herbicidal activity. Examples of the compounds which can be used in combination with the present compounds may include various compounds described in Catalog 1995 Edition of Farm Chemicals Handbook (Meister Publishing Company); AG CHEM NEW COMPOUND REVIEW, VOL. 13, 1995 (AG CHEM INFORMATION SERVICE); JOSOUZAI KENKYU SOURAN (Hakuyu-sha); or HERBICIDE HANDBOOK Seven Edition (Weed Science Society of America). Typical examples of such compounds are as follows: atrazin, cyanazine, dimethametryn, metribuzin, prometryn, simazine, simetryn, chlorotoluron, diuron, dymuron, fluometuron, isoproturon, linuron, methabenzthiazuron, bromoxynil, ioxynil, ethalfluralin, pendimethalin, trifluralin, acifluorfen, acifluorfen-sodium, bifenox, chlomethoxynil, fomesafen, lactofen, oxadiazon, oxyfluorfen, carfentrazone, flumiclorac-pentyl, flumioxazine, fluthiacetmethyl, sulfentrazone, thidiazimin, difenzoquat, diquat, paraquat, 2,4-D, 2,4-DB, DCPA, MCPA, MCPB, clomeprop, clopyralid, dicamba, dithiopyr, fluroxypyr, mecoprop, naploanilide, phenothiol, quinclorac, triclopyr, acetochlor, alachlor, butachlor, diethatylethyl, metolachlor, pretilachlor, propachlor, bensulfuron-methyl, chlorsulfuron, chlorimuron- ethyl, halosulfuron-methyl, metsulfuron-methyl, nicosulfuron, primisulfuron, pyrazosulfuron-ethyl, sulfometuron-methyl, thifensulfuronmethyl, triasulfuron, tribenuron-methyl, azimsulfuron, cloransulam-methyl, cyclosulfamuron, flumeturam, flupyrsulfuron, flazasulfuron, imazosulfuron, metosulam, prosulfuron, rimsulfuron, triflusulfuron-methyl, imazamethabenz-methyl, imazapyr, imazaquin, imazethapyr, imazameth, imazamox, bispyribac-sodium, pyriminobac-methyl, pyrithiobac-sodium, alloxydim-sodium, clethodim, sethoxydim, tralkoxydim, diclofop-methyl, fenoxaprop-ethyl, fenoxaprop-p-ethyl, fluazifop-butyl, fluazifop-p-butyl, haloxyfop-methyl, quizalofop-p-ethyl, cyhalofop-butyl, clodinafop-propargyl, benzofenap, clomazone, diflufenican, norflurazon, pyrazolate, pyrazoxyfen, isoxaflutole, sulcotrione, glufosinate-ammonium, glyphosate, bentazon, benthiocarb, bromobutide, butamifos, butylate, dimepiperate, dimethenarid, DSMA, EPTC, esprocarb, isoxaben, mefenacet, molinate, MSMA, piperophos, pributycarb, propanil, pyridate, triallate, cafenstrol, flupoxam, and thiafluamide.

In some cases, the present compounds may be used in combination with other herbicides to enhance their herbicidal activity. Furthermore, the present compounds can also be used in combination with insecticides, acaricides, nematocides, fungicides, plant growth regulators, fertilizers, soil improver, or the like.

When the present compounds are used as active ingredients of herbicides, the application amount is usually in the range of 0.01 to 10,000 g, preferably 1 to 8000 g, per hectare, although it may vary depending upon the weather conditions, formulation type, application timing, application method, soil conditions, crop plants, unfavorable weeds, and the like. In the case of emulsifiable concentrates, wettable powders, flowables, concentrated emulsions, water-dispersible granules, or the like, the formulation is usually applied at a prescribed amount after diluted with water having a volume of about 10 to 1000 liters per hectare, if necessary, with the addition of an adjuvant such as a spreading agent. In the case of granules or some types of flowables, the formulation is usually applied as such without any dilution.

Examples of the adjuvant used, if necessary, may include, in addition to the surfactants recited above, polyoxyethylene resin acids (esters), ligninsulfonates, abietates, dinaphthylmethanedisulfonates, crop oil concentrates, and vegetable oils such as soybean oil, corn oil, cotton seed oil, and sunflower oil.

The present compounds can also be used as active ingredients of harvesting aids such as defoliants and desiccating agents for cotton, and desiccating agents for potato. In these cases, the present compounds are usually formulated in the same manner as the case where they are used as active ingredients of herbicides, and used alone or in combination with other harvesting aids for foliar treatment before the harvesting of crops.

The present invention will be further illustrated by the following production examples, formulation examples, and test examples; however, the present invention is not limited to these examples.

The following will describe production examples for the present compounds, where the present compounds are designated by their compound numbers shown in Tables 1 to 5 and the intermediate compounds are designated by their compound numbers shown in Tables 6 to 8. For the measurement of $^1$H-NMR, tetramethylsilane was used as an internal standard.

PRODUCTION EXAMPLE 1

(1) First, 0.5 g of compound 1-1010 was dissolved in 5 ml of N,N-dimethylformamide, to which 0.5 g of potassium carbonate and 0.5 ml of methyl iodide were added, and the mixture was stirred at room temperature for 15 hours. After completion of the reaction, the reaction mixture was poured into water and extracted with ethyl acetate. The organic layer was dried and concentrated. The residue was subjected to preparative thin layer chromatography (using hexane-ethyl acetate 9 : 1 as an eluent), which afforded 0.1 g of compound 1-340.

$^1$H-NMR (60 MHz, CDCl$_3$): δ (ppm) 3.70 (3H, s), 6.70–7.05 (2H, m), 7.25–7.65 (1H, m), 8.00 (1H, s)

(2) Then, 0.45 g of compound 1-340 was poured into 10 ml of concentrated sulfuric acid at 0° C., to which 0.3 ml of nitric acid (d=1.42) was added, and the mixture was stirred at 0° to 5° C. for 1 hour. After completion of the reaction, the reaction mixture was added to ice water, and the precipitated crystals were collected by filtration. The crystals were dissolved in ethyl acetate, and the solution was washed with water. The organic layer was dried and concentrated. The residue was subjected to silica gel chromatography, which afforded 0.45 g of compound 1-346.

$^1$H-NMR (250 MHz, CDCl$_3$): δ (ppm) 3.76 (3H, s), 7.17 (1H, dd, J=10.0, 10.0 Hz), 8.16 (1H, d, J=1.6 Hz), 8.45 (1H, dd, J=7.3, 7.3 Hz)

(3) Then, 1.2 g of compound 1-346 was dissolved in 10 ml of 1,4-dioxane, to which 1.0 g of potassium fluoride and 1.0 ml of butyl glycolate were added, and the mixture was heated under reflux for 24 hours. After completion of the reaction, the reaction mixture was allowed to stand for cooling to room temperature. The reaction mixture was poured into water and extracted with ethyl acetate. The organic layer was dried and concentrated. The residue was subjected to silica gel chromatography, which afforded 1.2 g of the present compound represented by the following formula:

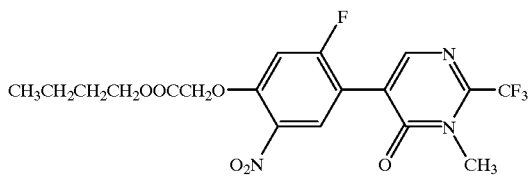

(4) Then, 2.0 g of iron powder was added to a mixed solution of 3 ml of acetic acid and 30 ml of water, followed by heating to 50° C., to which a solution of 1.2 g of the present compound obtained in the previous step (3) dissolved in 15 ml of ethyl acetate and 15 ml of acetic acid was slowly added dropwise. The mixture was stirred at an internal temperature of 60° to 70° C. for 40 minutes. After completion of the reaction, the reaction mixture was filtered through celite, and the filtrate was subjected to phase separation with ethyl acetate-aqueous sodium hydrogencarbonate solution. The organic layer was washed with water, dried, and concentrated, which afforded 1.0 g of compound 2-239, m.p. 194.0° C.

(5) Then, 1.0 g of compound 2-239 was dissolved in 15 ml of N,N-dimethylformamide, to which 1.6 g of potassium carbonate and 1.0 ml of propargyl bromide were added, and the mixture was stirred at room temperature for 1⅙ hours. After completion of the reaction, the reaction mixture was poured into water and extracted with ethyl acetate. The organic layer was dried and concentrated. The residue was subjected to silica gel chromatography, followed by recrystallization, which afforded 0.7 g of compound 2-251.

$^1$H-NMR (250 MHz, CDCl$_3$): δ (ppm) 2.27 (1H, t, J=2.5 Hz), 3.73 (3H, s), 4.68 (2H, s), 4.70 (2H, d, J=2.5 Hz), 6.86 (1H, d, J=10.2 Hz), 7.40 (1H, d, J=6.7 Hz), 8.11 (1H, d, J=1.7 Hz)

PRODUCTION EXAMPLE 2

First, 2.0 g of compound 1-1002 was dissolved in 30 ml of N,N-dimethylformamide, to which 2.17 g of potassium carbonate and 2.0 ml of methyl iodide were added, and the mixture was stirred at room temperature for 4 hours. After completion of the reaction, the reaction mixture was poured into water and extracted with ethyl acetate. The organic layer was dried and concentrated. The residue was subjected to silica gel chromatography, which afforded 0.65 g of compound 1-5.

$^1$H-NMR (60 MHz, CDCl$_3$): δ (ppm) 2.40 (3H, s), 3.60 (3H, s), 7.35 (2H, d, J=9 Hz), 7.60 (2H, d, J=9 Hz), 7.90 (1H, s)

PRODUCTION EXAMPLE 3

First, 0.5 g of compound 1-1004 was dissolved in 10 ml of N,N-dimethylformamide, to which 0.5 g of potassium carbonate and 0.5 ml of methyl iodide were added, and the mixture was stirred at room temperature for 2 hours. After completion of the reaction, the reaction mixture was poured into water and extracted with ethyl acetate. The organic layer was dried and concentrated. The residue was subjected to silica gel chromatography, which afforded 0.1 g of compound 1-10.

$^1$H-NMR (60 MHz, CDCl$_3$): δ (ppm) 2.55 (3H, s), 3.55 (3H, s), 6.60–7.00 (2H, m), 7.20–7.50 (1H, m), 7.85 (1H, s)

PRODUCTION EXAMPLE 4

First, 2.0 g of compound 1-1013 was dissolved in 30 ml of N,N-dimethylformamide, to which 2.17 g of potassium carbonate and 2.0 ml of methyl iodide were added, and the mixture was stirred at room temperature for 90 minutes. After completion of the reaction, the reaction mixture was poured into water and extracted with ethyl acetate. The organic layer was dried and concentrated. The residue was recrystallized, which afforded 1.16 g of compound 1-662.

$^1$H-NMR (60 MHz, CDCl$_3$): δ (ppm) 2.60 (3H, s), 3.60 (3H, s), 7.30 (2H, m), 7.45 (1H, m), 7.85 (1H, s)

PRODUCTION EXAMPLE 5

First, 0.3 g of compound 1-1008 was dissolved in 5 ml of N,N-dimethylformamide, to which 0.3 g of potassium carbonate and 0.3 ml of methyl iodide were added, and the mixture was stirred at room temperature for 75 minutes. After completion of the reaction, the reaction mixture was poured into water and extracted with ethyl acetate. The organic layer was dried and concentrated. The residue was subjected to silica gel chromatography, which afforded 0.1 g of compound 1-335.

$^1$H-NMR (60 MHz, CDCl$_3$): δ (ppm) 3.75 (3H, s), 7.35 (2H, d, J=9 Hz), 7.60 (2H, d, J=9 Hz), 8.00 (1H, s)

The structure of compound 1-335 was also confirmed by X-ray crystallography.

PRODUCTION EXAMPLE 6

First, 2.0 g of compound 1-1014 was dissolved in 20 ml of N,N-dimethylformamide, to which 2.5 g of potassium carbonate and 2.0 ml of methyl iodide were added, and the mixture was stirred at 100° C. for 15 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 0.9 g of compound 1-476.

¹H-NMR (250 MHz, CDCl₃): δ (ppm) 1.38 (6H, d, J=6.1 Hz), 3.73 (3H, s), 4.50 (1H, hp, J=6.1 Hz), 7.20 (1H, d, J=6.6 Hz), 7.23 (1H, d, J=9.6 Hz), 8.12 (1H, d, J=1.8 Hz)

PRODUCTION EXAMPLE 7

First, 0.7 g of compound 1-476 was poured into 10 ml of concentrated sulfuric acid, and the mixture was stirred at room temperature for 20 minutes. After completion of the reaction, the reaction mixture was poured into water and extracted with ethyl acetate. The organic layer was washed with saturated sodium chloride solution, dried, and concentrated. The residue was subjected to silica gel column chromatography, which afforded 0.5 g of compound 1-391.

¹H-NMR (300 MHz, CDCl₃): δ (ppm) 3.73 (3H, s), 5.45 (1H, s), 7.19 (1H, d, J=9.1 Hz), 7.20 (1H, d, J=6.5 Hz), 8.07 (1H, d, J=2 Hz)

PRODUCTION EXAMPLE 8

First, 0.3 g of compound 1-391 was dissolved in 5 ml of N,N-dimethylformamide, to which 0.5 g of potassium carbonate and 0.5 ml of allyl chloride were added, and the mixture was stirred at room temperature for 24 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 0.11 g of compound 1-482.

¹H-NMR (300 MHz, CDCl₃): δ (ppm) 3.73 (3H, s), 4.60 (2H, d, J=5.2 Hz), 5.33 (1H, dd, J=9.5, 1 Hz), 5.45 (1H, dd, J=16, 1 Hz), 6.06 (1H, tdd, J=5.2, 16, 9.5 Hz), 7.18 (1H, d, J=6.4 Hz), 7.24 (1H, d, J=9.6 Hz), 8.11 (1H, d, J=1.6 Hz)

PRODUCTION EXAMPLE 9

First, 0.25 g of compound 1-391 was dissolved in 8 ml of N,N-dimethylformamide, to which 0.3 g of potassium carbonate and 0.3 ml of propargyl bromide were added, and the mixture was stirred at room temperature for 1.5 hours. After completion of the reaction, the reaction mixture was poured into water and extracted with ethyl acetate. The organic layer was washed with saturated sodium chloride solution, dried, and concentrated. The residue was subjected to silica gel preparative thin layer chromatography, which afforded 0.25 g of compound 1-486.

¹H-NMR (250 MHz, CDCl₃): δ (ppm) 2.57 (1H, t, J=2.5 Hz), 3.74 (3H, s), 4.78 (2H, d, J=2.5 Hz), 7.26 (1H, d, J=9.4 Hz), 7.32 (1H, d, J=6.4 Hz), 8.12 (1H, d, J=1.7 Hz)

PRODUCTION EXAMPLE 10

First, 0.3 g of compound 1-391 was dissolved in 5 ml of N,N-dimethylformamide, to which 0.5 g of potassium carbonate and 0.5 ml of 3-bromo-1-butyne were added, and the mixture was stirred at room temperature for 45 minutes. After completion of the reaction, the reaction mixture was poured into water and extracted with ethyl acetate. The organic layer was washed with saturated sodium chloride solution, dried, and concentrated. The residue was subjected to silica gel column chromatography, which afforded 0.2 g of compound 1-487.

¹H-NMR (300 MHz, CDCl₃): δ (ppm) 1.72 (3H, d, J=6.6 Hz), 2.53 (1H, d, J=1.9 Hz), 3.73 (3H, s), 4.86 (1H, dt, J=1.9, 6.7 Hz), 7.24 (1H, d, J=9.4 Hz), 7.39 (1H, d, J 6.5 Hz), 8.11 (1H, s)

PRODUCTION EXAMPLE 11

First, 0.3 g of compound 1-391 was dissolved in 5 ml of N,N-dimethylformamide, to which 0.5 g of potassium carbonate and 0.5 ml of methyl bromoacetate were added, and the mixture was stirred at room temperature for 21 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 0.32 g of compound 1-495.

¹H-NMR (300 MHz, CDCl₃): δ (ppm) 3.72 (3H, s), 3.81 (3H, s), 4.71 (2H, s), 7.18 (1H, d, J=6.3 Hz), 7.26 (1H, d, J=9.4 Hz), 8.11 (1H, d, J=1.8 Hz)

PRODUCTION EXAMPLE 12

First, 0.27 g of compound 1-391 was dissolved in 8 ml of N,N-dimethylformamide, to which 0.3 g of potassium carbonate and 0.3 ml of ethyl bromoacetate were added, and the mixture was stirred at room temperature for 30 minutes. After completion of the reaction, the reaction mixture was poured into water and extracted with ethyl acetate. The organic layer was washed with saturated sodium chloride solution, dried, and concentrated. The residue was subjected to silica gel preparative thin layer chromatography, which afforded 0.34 g of compound 1-496.

¹H-NMR (300 MHz, CDCl₃): δ (ppm) 1.30 (3H, t, J=7.1 Hz), 3.72 (3H, s), 4.27 (2H, q, J=7.1 Hz), 4.69 (2H, s), 7.19 (1H, d, J=6.4 Hz), 7.26 (1H, d, J=9.5 Hz), 8.11 (1H, d, J=1.7 Hz)

PRODUCTION EXAMPLE 13

First, 0.3 g of compound 1-391 was dissolved in 5 ml of N,N-dimethylformamide, to which 0.5 g of potassium carbonate and 0.5 ml of n-amyl chloroacetate were added, and the mixture was stirred at room temperature for 24 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 0.18 g of compound 1-499.

¹H-NMR (300 MHz, CDCl₃): δ (ppm) 0.88 (3H, t, J=6.8 Hz), 1.25–1.45 (4H, m), 1.55–1.70 (2H, m), 3.72 (3H, s), 4.19 (2H, t, J=6.7 Hz), 4.70 (2H, s), 7.18 (1H, d, J=6.4 Hz), 7.26 (1H, d, J=9.4 Hz), 8.11 (1H, s)

PRODUCTION EXAMPLE 14

First, 0.3 g of compound 1-391 was dissolved in 5 ml of N,N-dimethylformamide, to which 0.5 g of potassium carbonate and 0.5 ml of methyl 2-bromopropionate were added, and the mixture was stirred at room temperature for 23.5 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 0.25 g of compound 1-503.

¹H-NMR (300 MHz, CDCl₃): δ (ppm) 1.67 (3H, d, J=6.7 Hz), 3.71 (3H, s), 3.78 (3H, s), 4.74 (1H, q, J=6.7 Hz), 7.17 (1H, d, J=6.4 Hz), 7.24 (1H, d, J=9.8 Hz), 8.09 (1H, d, J=1.7 Hz)

PRODUCTION EXAMPLE 15

First, 0.3 g of compound 1-391 was dissolved in 5 ml of N,N-dimethylformamide, to which 0.5 g of potassium carbonate and 0.5 ml of ethyl 2-bromopropionate were added, and the mixture was stirred at room temperature for 20 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 0.36 g of compound 1-504.

$^1$H-NMR (300 MHz, CDCl$_3$): δ (ppm) 1.26 (3H, t, J=7.1 Hz), 1.67 (3H, d, J=6.7 Hz), 3.71 (3H, s), 4.23 (2H, q, J=7.1 Hz), 4.73 (1H, q, J=6.7 Hz) 7.18 (1H, d, J=6.4 Hz), 7.24 (1H, d, J=9.9 Hz), 8.09 (1H, d, J=2 Hz)

PRODUCTION EXAMPLE 16

First, 0.4 g of compound 2-239 was dissolved in 10 ml of N,N-dimethylformamide, to which 0.4 g of potassium carbonate and 0.4 ml of 3-bromo-1-butyne were added, and the reaction was allowed to proceed at room temperature for 18.5 hours. After completion of the reaction, the reaction mixture was poured into water and extracted with ethyl acetate. The organic layer was washed with saturated sodium chloride solution, dried, and concentrated. The residue was subjected to preparative thin layer chromatography, which afforded 0.11 g of compound 2-252.

$^1$H-NMR (250 MHz, CDCl$_3$): δ (ppm) 1.66 (3H, d, J=7.3 Hz), 2.45 (1H, d, J=2.6 Hz), 3.74 (3H, br), 4.60 (1H, d, J=15.2 Hz), 4.67 (1H, d, J=15.2 Hz), 6.09 (1H, dq, J=2.6, 7.3 Hz), 6.87 (1H, d, J=10.2 Hz), 7.89 (1H, d, J=7.0 Hz), 8.12 (1H, d, J=1.8 Hz)

PRODUCTION EXAMPLE 17

(1) First, 5.5 g of compound 1-1007 was dissolved in 50 ml of N,N-dimethylformamide, to which 4.0 g of potassium carbonate and 2.5 ml of methyl iodide were added, and the mixture was stirred at room temperature for 4⅓ hours. After completion of the reaction, the reaction mixture was poured into water and extracted with ethyl acetate. The organic layer was successively washed with water and saturated sodium chloride solution, dried with magnesium sulfate, and concentrated. The residue was subjected to silica gel column chromatography, which afforded 0.16 g of compound 1-334.

$^1$H-NMR (250 MHz, CDCl$_3$): δ (ppm) 3.73 (3H, s), 7.15 (2H, dd, J=8.5, 8.5 Hz), 7.68 (2H, dd, J=5.4, 8.5 Hz), 8.70 (1H, s)

(2) Then, 1.0 g of compound 1-334 was suspended in 15 ml of sulfuric acid at 0° C., to which 0.5 ml of nitric acid (d=1.42) was slowly added dropwise with stirring, and the mixture was stirred at 5° C. for 1.25 hours. After completion of the reaction, the reaction mixture was poured into ice water and extracted with ethyl acetate. The organic layer was successively washed with water and saturated sodium chloride solution, dried, and concentrated. The residue was subjected to silica gel column chromatography, which afforded 1.0 g of compound 1-343.

$^1$H-NMR (250 MHz, CDCl$_3$): δ (ppm) 3.76 (3H, s), 7.40 (1H, dd, J=8.7, 10.4 Hz), 8.00 (1H, ddd, J=2.4, 6.5, 8.7 Hz), 8.17 (1H, s), 8.46 (1H, dd, J=7.1, 2.4 Hz)

(3) Then, 1.0 g of compound 1-343 was dissolved in 10 ml of 1,4-dioxane, to which 1.0 g of potassium fluoride and 0.7 ml of n-butyl glycolate were added, and the mixture was heated under reflux for 60 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 1.0 g of the present compound represented by the following formula:

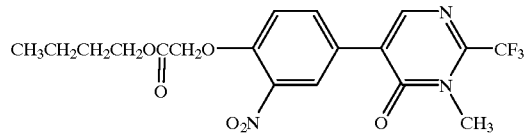

(4) Then, 1.5 g of iron powder was added to a mixed solution of 2.0 ml of acetic acid and 20 ml of water, followed by heating to 50° C., to which a solution of 1.0 g of the present compound obtained in the previous step (3) dissolved in 15 ml of ethyl acetate and 15 ml of acetic acid was slowly added dropwise, and the mixture was stirred at an internal temperature of 50° C. for 25 minutes. After completion of the reaction, the reaction mixture was filtered through celite, and the filtrate was subjected to phase separation with ethyl acetate-saturated aqueous sodium hydrogencarbonate solution. The organic layer was successively washed with water and saturated sodium chloride solution, dried, and concentrated. The residue was recrystallized from hexane-ethyl acetate, which afforded 0.6 g of compound 2-191.

$^1$H-NMR (250 MHz, CDCl$_3$): δ (ppm) 3.73 (3H, s), 4.66 (2H, s), 7.05 (1H, d, J=8.4 Hz), 7.22–7.32 (2H, m), 8.08 (1H, s)

(5) Then, 0.6 g of compound 2-191 was dissolved in 15 ml of N,N-dimethylformamide, to which 0.8 g of potassium carbonate and 0.8 ml of propargyl bromide were added, and the mixture was stirred at room temperature for 3 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 0.6 g of compound 2-203.

$^1$H-NMR (250 MHz, CDCl$_3$): δ (ppm) 2.29 (1H, t, J=2.5 Hz), 3.74 (3H, s), 4.69 (2H, s), 4.75 (2H, d, J=2.5 Hz), 7.09 (1H, d, J=8.4 Hz), 7.36 (1H, dd, J=2.0, 8.4 Hz), 7.61 (1H, d, J=2.0 Hz), 8.11 (1H, s)

PRODUCTION EXAMPLE 18

First, 0.3 g of compound 1-391 was dissolved in 5 ml of N,N-dimethylforrnamide, to which 0.3 g of potassium carbonate and 0.5 ml of chloroacetonitrile were added, and the mixture was stirred at room temperature for 1 hour. After completion of the reaction, the reaction mixture was poured into water and extracted with ethyl acetate. The organic layer was washed with saturated sodium chloride solution, dried, and concentrated. The residue was subjected to preparative thin layer chromatography, which afforded 0.3 g of compound 1-491.

$^1$H-NMR (250 MHz, CDCl$_3$): δ (ppm) 3.74 (3H, s), 4.84 (2H, s), 7.31 (1H, d, J=9.4 Hz), 7.42 (1H, d, J=6.3 Hz), 8.16 (1H, d, J=1.8 Hz)

PRODUCTION EXAMPLE 19

First, 2.0 g of iron powder was added to a mixed solution of 5.0 ml of acetic acid and 50 ml of water, followed by heating to 50° C., to which a solution of 3.0 g of compound 1-346 in 30 ml of ethyl acetate and 10 ml of acetic acid was slowly added dropwise, and the mixture was stirred at an internal temperature of 50° to 60° C. for 30 minutes. After completion of the reaction, the reaction mixture was filtered through celite, and the filtrate was subjected to phase separation with ethyl acetate-saturated aqueous sodium hydrogencarbonate solution. The organic layer was successively washed with water and saturated sodium chloride solution, dried, and concentrated. The precipitated crystals were recrystallized from hexane-ethyl acetate, which afforded 2.4 g of compound 1-352.

$^1$H-NMR (250 MHz, CDCl$_3$): δ (ppm) 3.67 (2H, br), 3.72 (3H, s), 6.89 (1H, dd, J=9.8, 10.6 Hz), 6.96 (1H, dd, J=7.1, 9.6 Hz), 8.06 (1H, d, J=1.6 Hz)

PRODUCTION EXAMPLE 20

First, 0.8 g of compound 1-352 was dissolved in 8 ml of ethyl 2-bromopropionate, and the mixture was stirred at 80° C. for 10 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 0.36 g of compound 1-663.

$^1$H-NMR (250 MHz, CDCl$_3$): δ (ppm) 1.26 (3H, t, J=7.0 Hz), 1.50 (3H, d, J=6.9 Hz), 3.72 (3H, s), 4.04–4.14 (1H, m), 4.20 (2H, q, J=7.0 Hz), 4.28–4.33 (1H, m), 6.77 (1H, dd, J=6.9, 9.4 Hz), 6.90 (1H, dd, J=9.7, 11.0 Hz), 8.04 (1H, d, J=1.5Hz)

PRODUCTION EXAMPLE 21

First, 9.4 g of compound 1-1015 was dissolved in 100 ml of N,N-dimethylformamide, to which 10 g of potassium carbonate and 5.0 ml of methyl iodide were added, and the mixture was stirred at 100° C. for 10 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 1.7 g of compound 1-664.

$^1$H-NMR (250 MHz, CDCl$_3$): δ (ppm) 3.73 (3H, s), 7.29 (1H, d, J=8.2 Hz), 7.34 (1H, dd, J=1.8, 8.2 Hz), 7.52 (1H, d, J=1.8 Hz), 8.00 (1H, s)

PRODUCTION EXAMPLE 22

First, 1.4 g of compound 1-664 was pulverized with a mortar and poured into 20 ml of sulfuric acid cooled to 5° C., followed by stirring for 10 minutes, to which 1.0 ml of nitric acid (d=1.42) was slowly added dropwise, and the mixture was further stirred at 5° C. for 1 hour. After completion of the reaction, the reaction mixture was poured into ice water, and the precipitated crystals were collected by filtration. The crystals were dissolved in ethyl acetate, and the solution was washed with water. The organic layer was washed with saturated sodium chloride solution, dried, and concentrated, which afforded 1.4 g of compound 1-665.

$^1$H-NMR (250 MHz, CDCl$_3$): δ (ppm) 3.75 (3H, s), 7.73 (1H, s), 8.00 (1H, s), 8.08 (1H, s)

PRODUCTION EXAMPLE 23

First, 3.0 g of iron powder was added to a mixed solution of 3.0 ml of acetic acid and 30 ml of water, followed by heating to 50° C., to which a solution of 1.2 g of compound 1-665 in 10 ml of ethyl acetate and 10 ml of acetic acid was slowly added dropwise, and the mixture was stirred at an internal temperature of 70° C. for 25 minutes. After completion of the reaction, the reaction mixture was filtered through celite, and the filtrate was subjected to phase separation with ethyl acetate-saturated aqueous sodium hydrogencarbonate solution. The organic layer was successively washed with water and saturated sodium chloride solution, dried, and concentrated. The residue was recrystallized from hexane-ethyl acetate, which afforded 1.0 g of compound 1-666.

$^1$H-NMR (250 MHz, CDCl$_3$): δ (ppm) 3.72 (3H, br), 4.12 (2H, br), 6.74 (1H, s), 7.39 (1H, s), 7.98 (1H, s)

PRODUCTION EXAMPLE 24

First, 1.0 g of compound 1-666 was dissolved in 10 ml of ethyl 2-bromopropionate, and the mixture was stirred at 80° C. for 33 hours. After completion of the reaction, the reaction mixture was poured into water and extracted with ethyl acetate. The organic layer was washed with saturated sodium chloride solution, dried, and concentrated. The residue was successively subjected to silica gel column chromatography and preparative thin layer chromatography, which afforded 0.25 g of compound 1-667.

$^1$H-NMR (250 MHz, CDCl$_3$): δ (ppm) 1.26 (3H, t, J=7.0 Hz), 1.51 (3H, d, J=6.9 Hz), 3.73 (3H, s), 4.10 (1H, dq, J=7.6, 6.9 Hz), 4.21 (2H, d, J=7.0 Hz), 4.90 (1H, d, J=7.6 Hz), 6.52 (1H, s), 7.41 (1H, s), 7.97 (1H, s)

PRODUCTION EXAMPLE 25

First, 0.5 g of compound 1-666 was dissolved in 5 ml of pyridine, to which 0.3 ml of methanesulfonyl chloride was added, and the reaction was allowed to proceed at room temperature for 23 hours. After completion of the reaction, the reaction mixture was poured into water and extracted with ethyl acetate. The organic layer was washed with saturated sodium chloride solution, dried, and concentrated, after which the pyridine was removed by azeotropic distillation with toluene. The residue was subjected to silica gel column chromatography, which afforded 0.4 g of compound 1-668.

$^1$H-NMR (250 MHz, CDCl$_3$): δ (ppm) 3.08 (3H, s), 3.74 (3H, s), 6.89 (1H, br), 7.59 (1H, s), 7.67 (1H, s), 8.04 (1H, s)

PRODUCTION EXAMPLE 26

First, 25.6 g of compound 1-1011 was dissolved in 200 ml of N,N-dimethylformamide, to which 40 g of potassium carbonate and 40 ml of methyl iodide were added, and the mixture was stirred at 100° C. for 6⅔ hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 7.0 g of compound 1-341.

$^1$H-NMR (300 MHz, CDCl$_3$): δ (ppm) 3.73 (3H, s), 7.19–7.26 (2H, m), 7.49 (1H, dd, J=7.8, 7.8 Hz), 8.08 (1H, d, J=1.4 Hz)

PRODUCTION EXAMPLE 27

First, 7.0 g of compound 1-341 was poured into 100 ml of sulfuric acid at 0° C., to which 3.0 ml of nitric acid (d=1.42) was slowly added dropwise, and the mixture was stirred at 0° C. for 1⅓ hours. After completion of the reaction, the reaction mixture was poured into water, and the precipitated crystals were collected by filtration. The crystals were dissolved in ethyl acetate, and the solution was washed with water. The organic layer was washed with saturated sodium chloride solution, dried, and concentrated. The crystals were recrystallized from hexane-ethyl acetate, which afforded 7.6 g of compound 1-347, m.p. 135.2° C.

PRODUCTION EXAMPLE 28

First, 7.7 g of iron powder was added to a mixed solution of 5.0 ml of acetic acid and 50 ml of water, followed by heating to 50° C., to which a solution of 7.7 g of compound 1-347 in 50 ml of ethyl acetate and 50 ml of acetic acid was slowly added dropwise, and the mixture was stirred at an internal temperature of 50° to 70° C. for 50 minutes. After completion of the reaction, the reaction mixture was filtered through celite, and the filtrate was subjected to phase separation with ethyl acetate-saturated aqueous sodium hydrogencarbonate solution. The organic layer was successively washed with water and saturated sodium chloride solution, dried, and concentrated. The precipitated crystals were recrystallized from hexane-ethyl acetate, which afforded 6.4 g of compound 1-353, m.p. 152.7° C.

PRODUCTION EXAMPLE 29

First, 0.7 g of compound 1-353 was dissolved in 10 ml of ethyl 2-bromopropionate, and the mixture was stirred at 100° C. for 6 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 0.2 g of compound 1-420.

$^1$H-NMR (250 MHz, CDCl$_3$): δ (ppm) 1.26 (3H, t, J=7.2 Hz), 1.52 (3H, d, J=6.9 Hz), 3.71 (3H, s), 4.12 (1H, br), 4.21 (2H, q, J=7.2 Hz), 4.71 (1H. br), 6.75 (1H, d, J=6.5 Hz), 7.17 (1H, d, J=9.5 Hz), 8.06 (1H, d, J=1.6 Hz)

PRODUCTION EXAMPLE 30

First, 0.3 g of compound 1-353 was dissolved in 5 ml of pyridine, to which 0.5 ml of methanesulfonyl chloride was added, and the mixture was stirred at room temperature for 30 minutes. After completion of the reaction, the reaction mixture was poured into water and extracted with ethyl acetate. The organic layer was washed with saturated sodium chloride solution, dried, and concentrated, after which the pyridine was removed by azeotropic distillation with toluene. The residue was subjected to preparative thin layer chromatography, which afforded 0.3 g of compound 1-367.

$^1$H-NMR (250 MHz, CDCl$_3$): δ (ppm) 3.06 (3H, s), 3.74 (3H, s), 6.85 (1H, br), 7.30 (1H, d, J=9.1 Hz), 7.84 (1H, d, J=6.9 Hz), 8.11 (1H, d, J=1.4 Hz)

PRODUCTION EXAMPLE 31

First, 0.3 g of compound 1-353 was dissolved in 5 ml of pyridine, to which 5 ml of acetic anhydride was added, and the mixture was stirred at room temperature for 5 hours. After completion of the reaction, toluene was added to the reaction mixture, which was concentrated. The precipitated crystals were recrystallized from hexane-ethyl acetate, which afforded 0.27 g of compound 1-669.

$^1$H-NMR (250 MHz, CDCl$_3$): δ (ppm) 2.24 (3H, s), 3.73 (3H, s), 7.25 (1H, d, J=8.4 Hz), 7.51 (1H, br), 8.08 (1H, s), 8.51 (1H, d, J=7.1 Hz)

PRODUCTION EXAMPLE 32

First, 0.18 g of sodium hydride (60% in oil) was suspended in 10 ml of N,N-dimethylformamide, to which 10 ml of a solution containing 1.0 g of compound 1-1014 in N,N-dimethylformamide was added dropwise at 5° C. The reaction mnixture was warmed to room temperature and stirred for 1.5 hours, to which 0.5 ml of methyl iodide was added dropwise. The stirring was further continued at room temperature for 4.5 hours. After completion of the reaction, the reaction mixture was poured into water and extracted with ethyl acetate. The organic layer was washed with saturated sodium chloride solution, dried, and concentrated. The residue was subjected to silica gel chromatography, which afforded 0.37 g of 5-(4-chloro-2-fluoro-5-isopropoxyphenyl)-4-methoxy-2-trifluoromethylpyrimidine, m.p. 77.8° C., and 0.23 g of compound 1-476.

PRODUCTION EXAMPLE 33

First, 0.5 ml of t-butyl nitrite, 3.3 ml of ethyl acrylate, and 0.5 g of copper (II) chloride were poured into 25 ml of acetonitrile, followed by cooling to 0° C., to which 10 ml of a solution containing 1.0 g of compound 1-353 in acetonitrile was slowly added dropwise, and the mixture was stirred at 0° C. for 3 hours. After completion of the reaction, the reaction mixture was poured into water and extracted with ethyl acetate. The organic layer was washed with saturated sodium chloride solution, dried, and concentrated. The residue was subjected to silica gel column chromatooraphy, which afforded 0.5 g of compound 1-713.

$^1$H-NMR (250 MHz, CDCl$_3$): δ (ppm) 1.27 (3H, t, J=7.2 Hz), 3.28 (1H, dd, J=8.3, 14.2 Hz), 3.52 (1H, dd, J=6.5, 14.2 Hz), 3.73 (3H, s), 4.22 (½×2H, q, J=7.2 Hz), 4.23 (½×2H, q, J=7.2 Hz), 4.56 (1H, dd, J=6.5, 8.3 Hz), 7.26 (1H, d, J=9.7 Hz), 7.51 (1H, d, J=7.6 Hz), 8.07 (1H, d,J=1.4 Hz)

PRODUCTION EXAMPLE 34

First, 0.5 g of compound 1-353 was dissolved in 5 ml of ethyl bromoacetate, and the solution was stirred at 100° C. for 9 hours. After completion of the reaction, the reaction mixture was allowed to stand for cooling to room temperature. The reaction mixture was poured into water and extracted with ethyl acetate. The organic layer was washed with saturated sodium chloride solution, dried, and concentrated. The residue was subjected to silica gel column chromatography, which afforded 0.25 g of compound 1-380.

$^1$H-NMR (300 MHz, CDCl$_3$): δ (ppm) 1.30 (3H, t, J=7.1 Hz), 3.72 (3H, s), 3.94 (2H, s), 4.26 (2H, q, J=7.1 Hz), 4.85 (1H, br), 6.70 (1H, d, J=6.5 Hz), 7.18 (1H, d, J=9.4 Hz), 8.08 (1H, d, J=1.5 Hz)

PRODUCTION EXAMPLE 35

First, 7.5 ml of water and 7.5 ml of concentrated hydrochloric acid were added to 2.15 g of compound 1-353, and the mixture was stirred at 50° C. for 1⅔ hours and then cooled to 5° C., to which a solution of 0.5 g of sodium nitrite in 10 ml of water was slowly added dropwise, and the mixture was further stirred at 5° C. for 50 minutes. The solution of a diazonium salt thus formed was added dropwise to a solution of 25 g of potassium iodide in 50 ml of water at room temperature, and the mixture was further stirred at room temperature for 30 minutes. After completion of the reaction, the reaction mixture was poured into water and extracted with ethyl acetate. The organic layer was washed with saturated sodium chloride solution, dried, and concentrated. The residue was recrystallized from hexane-ethyl acetate, which afforded 1.93 g of compound 1-714, m.p. 156.8° C.

PRODUCTION EXAMPLE 36

First, 0.5 g of compound 1-714 was dissolved in 5 ml of N,N-dimethylformamide, to which 5 ml of ethanol, 1.0 ml of diethylamine, and 0.1 g of dichlorobis(triphenylphosphine) palladium were added, and carbon monoxide was bubbled into the mixture at room temperature for 13 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 0.19 g of compound 1-642.

$^1$H-NMR (250 MHz, CDCl$_3$): δ (ppm) 1.40 (3H, t, J=7.1 Hz), 3.74 (3H, s), 4.40 (2H, q, J=7.1 Hz), 7.32 (1H, d, J=9.6 Hz), 8.10 (1H, d, J=7.7 Hz), 8.10 (1H, d, J=1.2 Hz)

PRODUCTION EXAMPLE 37

First, 0.9 g of compound 1-714 was dissolved in 10 ml of N,N-dimethylformamide, to which 2.5 g of sodium formate and a catalytic amount of dichlorobis(triphenylphosphine) palladium were added, and carbon monoxide was bubbled into the mixture at room temperature for 25.5 hours. After completion of the reaction, the reaction mixture was poured into diluted hydrochloric acid and extracted with ethyl acetate. The organic layer was washed with water and saturated sodium chloride solution, dried, and concentrated. The residue was subjected to silica gel column chromatography, which afforded 0.22 g of compound 1-656, m.p. 158.6° C.

$^1$H-NMR (250 MHz, CDCl$_3$): δ (ppm) 3.74 (3H, s), 7.33 (1H, d, J 9.3 Hz), 8.09 (1H, s), 8.12 (1H, d, J=7.8 Hz), 10.42 (1H, s)

PRODUCTION EXAMPLE 38

First, 0.15 g of compound 1-391 was dissolved in 5 ml of N,N-dimethylfornamide, to which 0.2 g of potassium carbonate and 0.2 ml of cyclopentyl bromide were added, and the reaction was allowed to proceed at room temperature for 21 hours. After completion of the reaction, the reaction mixture was poured into water and extracted with ethyl acetate. The organic layer was washed with saturated sodium chloride solution, dried, and concentrated. The residue was subjected to preparative thin layer chromatography, which afforded 0.14 g of compound 1-480, m.p. 101.6° C.

PRODUCTION EXAMPLE 39

First, 1.5 g of compound 1-391 was dissolved in 15 ml of N,N-dimethylformamide, to which 1.5 g of potassium carbonate and 0.7 ml of methallyl chloride were added, and the reaction was allowed to proceed at room temperature for 19 hours. After completion of the reaction, the reaction mixture was poured into water and extracted with ethyl acetate. The organic layer was washed with saturated sodium chloride solution, dried, and concentrated. The resiude was subjected to silica gel column chromatography, which afforded 0.8 g of compound 1-715.

$^1$H-NMR (250 MHz, CDCl$_3$): δ (ppm) 1.85 (3H, s), 3.73 (3H, s), 4.49 (2H, s), 5.02 (1H, d, J=1.3 Hz), 5.14 (1H, d, J=1.3 Hz), 7.15 (1H, d, J=6.4 Hz), 7.24 (1H, d, J=9.3 Hz), 8.11 (1H, d, J=1.8 Hz)

PRODUCTION EXAMPLE 40

First, 0.33 g of compound 1-391 was dissolved in 5 ml of N,N-dimethylformamide, to which 0.23 g of potassium carbonate and 0.3 ml of 2,3-dichloropropene were added, and the reaction was allowed to proceed at room temperature for 1 hour. After completion of the reaction, the reaciton mixture was poured into water and extracted with ethyl acetate. The organic layer was washed with saturated sodium chloride solution, dried, and concentrated. The residue was subjected to thin layer chromatography, which afforded 0.05 g of comound 1-483.

$^1$H-NMR (250 MHz, CDCl$_3$): δ (ppm) 3.74 (3H, s), 4.64 (2H, s), 5.49 (1H, d, J=1.1 Hz), 5.66 (1H, d, J=1.1 Hz), 7.20 (1H, d, J=6.4 Hz), 7.27 (H, d, J=9.4 Hz), 8.12 (1H, d, J=1.7 Hz)

PRODUCTION EXAMPLE 41

First, 0.33 g of compound 1-391 was dissolved in 5 ml of N,N-dimethylformamide, to which 0.3 g of potassium carbonate and 0.3 g of chloromethyl ethyl ether were added, and the reaction was allowed to proceed at room temperature for 30 minutes. After completion of the reaction, the reaciton mixture was poured into water and extracted with ethyl acetate. The organic layer was washed with saturated sodium chloride solution, dried, and concentrated. The residue was subjected to thin layer chromatography, which afforded 0.3 g of comound 1-493.

$^1$H-NMR (250 MHz, CDCl$_3$): δ (ppm) 1.24 (3H, t, J=7.1 Hz), 3.73 (3H, s), 3.79 (2H, q, J=7.1 Hz), 5.28 (2H, s), 7.24 (1H, d, J=9.36 Hz), 7.40 (1H, d, J=6.6 Hz), 8.09 (1H, d, J=1.4 Hz)

PRODUCTION EXAMPLE 42

First, 0.3 g of compound 1-391 was dissolved in 2 ml of dimethylsulfoxide, to which 1 ml of acetic anhydride was added, and the reaction was allowed to proceed at room temperature for 18 hours. After completion of the reaction, the reaciton mixture was poured into water and extracted with ethyl acetate. The organic layer was washed with saturated sodium chloride solution, dried, and concentrated. The residue was subjected to silica gel column chromatography, which afforded 0.13 g of comound 1-494, m.p. 126.8° C.

Some of the present compounds are shown with their compound numbers in Tables 1 to 5, where the symbol "n" refers to normal-; "i", iso-; and "c", cyclo-.

TABLE 1

Compounds of the formula:

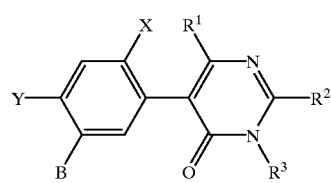

| Compound No. | X | Y | R$^1$ | R$^2$ | R$^3$ | B |
|---|---|---|---|---|---|---|
| 1-1 | H | F | H | CH$_3$ | C$_2$H$_5$ | H |
| 1-2 | H | Cl | H | CH$_3$ | C$_2$H$_5$ | H |
| 1-3 | H | Br | H | CH$_3$ | C$_2$H$_5$ | H |
| 1-4 | H | F | H | CH$_3$ | CH$_3$ | H |
| 1-5 | H | Cl | H | CH$_3$ | CH$_3$ | H |
| 1-6 | H | Br | H | CH$_3$ | CH$_3$ | H |
| 1-7 | F | F | H | CH$_3$ | C$_2$H$_5$ | H |
| 1-8 | F | Cl | H | CH$_3$ | C$_2$H$_5$ | H |
| 1-9 | F | Br | H | CH$_3$ | C$_2$H$_5$ | H |
| 1-10 | F | F | H | CH$_3$ | CH$_3$ | H |
| 1-11 | F | Cl | H | CH$_3$ | CH$_3$ | H |
| 1-12 | F | Br | H | CH$_3$ | CH$_3$ | H |
| 1-13 | H | F | H | CH$_3$ | CH$_3$ | NO$_2$ |
| 1-14 | H | Cl | H | CH$_3$ | CH$_3$ | NO$_2$ |
| 1-15 | H | Br | H | CH$_3$ | CH$_3$ | NO$_2$ |
| 1-16 | F | F | H | CH$_3$ | CH$_3$ | NO$_2$ |
| 1-17 | F | Cl | H | CH$_3$ | CH$_3$ | NO$_2$ |

TABLE 1-continued

Compounds of the formula:

[Structure: phenyl ring with X, Y, B substituents connected to pyrimidinone ring with $R^1$, $R^2$, $R^3$ substituents]

| Compound No. | X | Y | $R^1$ | $R^2$ | $R^3$ | B |
|---|---|---|---|---|---|---|
| 1-18 | F | Br | H | $CH_3$ | $CH_3$ | $NO_2$ |
| 1-19 | H | F | H | $CH_3$ | $CH_3$ | $NH_2$ |
| 1-20 | H | Cl | H | $CH_3$ | $CH_3$ | $NH_2$ |
| 1-21 | H | Br | H | $CH_3$ | $CH_3$ | $NH_2$ |
| 1-22 | F | F | H | $CH_3$ | $CH_3$ | $NH_2$ |
| 1-23 | F | Cl | H | $CH_3$ | $CH_3$ | $NH_2$ |
| 1-24 | F | Br | H | $CH_3$ | $CH_3$ | $NH_2$ |
| 1-25 | H | F | H | $CH_3$ | $CH_3$ | OH |
| 1-26 | H | Cl | H | $CH_3$ | $CH_3$ | OH |
| 1-27 | H | Br | H | $CH_3$ | $CH_3$ | OH |
| 1-28 | F | F | H | $CH_3$ | $CH_3$ | OH |
| 1-29 | F | Cl | H | $CH_3$ | $CH_3$ | OH |
| 1-30 | F | Br | H | $CH_3$ | $CH_3$ | OH |
| 1-31 | H | Cl | H | $CH_3$ | $CH_3$ | $NHCH_3$ |
| 1-32 | H | Cl | H | $CH_3$ | $CH_3$ | $NHC_2H_5$ |
| 1-33 | H | Cl | H | $CH_3$ | $CH_3$ | $NHCH_2CH{=}CH_2$ |
| 1-34 | H | Cl | H | $CH_3$ | $CH_3$ | $NHCH_2C{\equiv}CH$ |
| 1-35 | H | Cl | H | $CH_3$ | $CH_3$ | $NHCH(CH_3)C{\equiv}CH$ |
| 1-36 | H | Cl | H | $CH_3$ | $CH_3$ | $NHSO_2CH_3$ |
| 1-37 | H | Cl | H | $CH_3$ | $CH_3$ | $NHSO_2C_2H_5$ |
| 1-38 | H | Cl | H | $CH_3$ | $CH_3$ | $NHSO_2CH_2Cl$ |
| 1-39 | H | Cl | H | $CH_3$ | $CH_3$ | $NHSO_2CF_3$ |
| 1-40 | H | Cl | H | $CH_3$ | $CH_3$ | $N(CH_3)SO_2CH_3$ |
| 1-41 | H | Cl | H | $CH_3$ | $CH_3$ | $N(CH_2C{\equiv}CH)SO_2CH_3$ |
| 1-42 | H | Cl | H | $CH_3$ | $CH_3$ | $NHCOOCH_3$ |
| 1-43 | H | Cl | H | $CH_3$ | $CH_3$ | $NHCOOC_2H_5$ |
| 1-44 | H | Cl | H | $CH_3$ | $CH_3$ | $NHCOO^nC_3H_7$ |
| 1-45 | H | Cl | H | $CH_3$ | $CH_3$ | $NHCOO^iC_3H_7$ |
| 1-46 | H | Cl | H | $CH_3$ | $CH_3$ | $NHCOO^nC_4H_9$ |
| 1-47 | H | Cl | H | $CH_3$ | $CH_3$ | $NHCOO^nC_5H_{11}$ |
| 1-48 | H | Cl | H | $CH_3$ | $CH_3$ | $NHCH_2COOCH_3$ |
| 1-49 | H | Cl | H | $CH_3$ | $CH_3$ | $NHCH_2COOC_2H_5$ |
| 1-50 | H | Cl | H | $CH_3$ | $CH_3$ | $NHCH_2COO^nC_3H_7$ |
| 1-51 | H | Cl | H | $CH_3$ | $CH_3$ | $NHCH_2COO^nC_4H_9$ |
| 1-52 | H | Cl | H | $CH_3$ | $CH_3$ | $NHCH_2COO^nC_5H_{11}$ |
| 1-53 | H | Cl | H | $CH_3$ | $CH_3$ | $NHCH_2COO^iC_3H_7$ |
| 1-54 | H | Cl | H | $CH_3$ | $CH_3$ | $NHCH_2COO^cC_5H_9$ |
| 1-55 | H | Cl | H | $CH_3$ | $CH_3$ | $NHCH_2COO^cC_6H_{11}$ |
| 1-56 | H | Cl | H | $CH_3$ | $CH_3$ | $NHCH(CH_3)COOCH_3$ |
| 1-57 | H | Cl | H | $CH_3$ | $CH_3$ | $NHCH(CH_3)COOC_2H_5$ |
| 1-58 | H | Cl | H | $CH_3$ | $CH_3$ | $NHCH(CH_3)COO^nC_3H_7$ |
| 1-59 | H | Cl | H | $CH_3$ | $CH_3$ | $NHCH(CH_3)COO^nC_4H_9$ |
| 1-60 | H | Cl | H | $CH_3$ | $CH_3$ | $NHCH(CH_3)COO^nC_5H_{11}$ |
| 1-61 | H | Cl | H | $CH_3$ | $CH_3$ | $NHCH(CH_3)COO^iC_3H_7$ |
| 1-62 | H | Cl | H | $CH_3$ | $CH_3$ | $NHCH(CH_3)COO^cC_5H_9$ |
| 1-63 | H | Cl | H | $CH_3$ | $CH_3$ | $NHCH(CH_3)COO^cC_6H_{11}$ |
| 1-64 | F | Cl | H | $CH_3$ | $CH_3$ | $NHCH_3$ |
| 1-65 | F | Cl | H | $CH_3$ | $CH_3$ | $NHC_2H_5$ |
| 1-66 | F | Cl | H | $CH_3$ | $CH_3$ | $NHCH_2CH{=}CH_2$ |
| 1-67 | F | Cl | H | $CH_3$ | $CH_3$ | $NHCH_2C{\equiv}CH$ |
| 1-68 | F | Cl | H | $CH_3$ | $CH_3$ | $NHCH(CH_3)C{\equiv}CH$ |
| 1-69 | F | Cl | H | $CH_3$ | $CH_3$ | $NHSO_2CH_3$ |
| 1-70 | F | Cl | H | $CH_3$ | $CH_3$ | $NHSO_2C_2H_5$ |
| 1-71 | F | Cl | H | $CH_3$ | $CH_3$ | $NHSO_2CH_2Cl$ |
| 1-72 | F | Cl | H | $CH_3$ | $CH_3$ | $NHSO_2CF_3$ |
| 1-73 | F | Cl | H | $CH_3$ | $CH_3$ | $N(CH_3)SO_2CH_3$ |
| 1-74 | F | Cl | H | $CH_3$ | $CH_3$ | $N(CH_2C{\equiv}CH)SO_2CH_3$ |
| 1-75 | F | Cl | H | $CH_3$ | $CH_3$ | $NHCOOCH_3$ |
| 1-76 | F | Cl | H | $CH_3$ | $CH_3$ | $NHCOOC_2H_5$ |
| 1-77 | F | Cl | H | $CH_3$ | $CH_3$ | $NHCOO^nC_3H_7$ |
| 1-78 | F | Cl | H | $CH_3$ | $CH_3$ | $NHCOO^iC_3H_7$ |
| 1-79 | F | Cl | H | $CH_3$ | $CH_3$ | $NHCOO^nC_4H_9$ |
| 1-80 | F | Cl | H | $CH_3$ | $CH_3$ | $NHCOO^nC_5H_{11}$ |
| 1-81 | F | Cl | H | $CH_3$ | $CH_3$ | $NHCH_2COOCH_3$ |
| 1-82 | F | Cl | H | $CH_3$ | $CH_3$ | $NHCH_2COOC_2H_5$ |
| 1-83 | F | Cl | H | $CH_3$ | $CH_3$ | $NHCH_2COO^nC_3H_7$ |
| 1-84 | F | Cl | H | $CH_3$ | $CH_3$ | $NHCH_2COO^nC_4H_9$ |
| 1-85 | F | Cl | H | $CH_3$ | $CH_3$ | $NHCH_2COO^nC_5H_{11}$ |
| 1-86 | F | Cl | H | $CH_3$ | $CH_3$ | $NHCH_2COO^iC_3H_7$ |
| 1-87 | F | Cl | H | $CH_3$ | $CH_3$ | $NHCH_2COO^cC_5H_9$ |
| 1-88 | F | Cl | H | $CH_3$ | $CH_3$ | $NH_2CH_2COO^cC_6H_{11}$ |
| 1-89 | F | Cl | H | $CH_3$ | $CH_3$ | $NHCH(CH_3)COOCH_3$ |
| 1-90 | F | Cl | H | $CH_3$ | $CH_3$ | $NHCH(CH_3)COOC_2H_5$ |
| 1-91 | F | Cl | H | $CH_3$ | $CH_3$ | $NHCH(CH_3)COO^nC_3H_7$ |
| 1-92 | F | Cl | H | $CH_3$ | $CH_3$ | $NHCH(CH_3)COO^nC_4H_9$ |
| 1-93 | F | Cl | H | $CH_3$ | $CH_3$ | $NHCH(CH_3)COO^nC_5H_{11}$ |
| 1-94 | F | Cl | H | $CH_3$ | $CH_3$ | $NHCH(CH_3)COO^iC_3H_7$ |
| 1-95 | F | Cl | H | $CH_3$ | $CH_3$ | $NHCH(CH_3)COO^cC_5H_9$ |
| 1-96 | F | Cl | H | $CH_3$ | $CH_3$ | $NHCH(CH_3)COO^cC_6H_{11}$ |
| 1-97 | H | Cl | H | $CH_3$ | $CH_3$ | $OCH_3$ |
| 1-98 | H | Cl | H | $CH_3$ | $CH_3$ | $OC_2H_5$ |
| 1-99 | H | Cl | H | $CH_3$ | $CH_3$ | $O^iC_3H_7$ |
| 1-100 | H | Cl | H | $CH_3$ | $CH_3$ | $O^nC_3H_7$ |
| 1-101 | H | Cl | H | $CH_3$ | $CH_3$ | $OCH_2CH_2Cl$ |
| 1-102 | H | Cl | H | $CH_3$ | $CH_3$ | $OCF_2CF_2H$ |
| 1-103 | H | Cl | H | $CH_3$ | $CH_3$ | $O^cC_5H_9$ |
| 1-104 | H | Cl | H | $CH_3$ | $CH_3$ | $O^cC_6H_{11}$ |
| 1-105 | F | Cl | H | $CH_3$ | $CH_3$ | $OCH_2CH{=}CH_2$ |
| 1-106 | F | Cl | H | $CH_3$ | $CH_3$ | $OCH_2CCl{=}CH_2$ |
| 1-107 | F | Cl | H | $CH_3$ | $CH_3$ | $OCH_2CCl{=}CHCl$ |
| 1-108 | F | Cl | H | $CH_3$ | $CH_3$ | $OCH(CH_3)CH{=}CH_2$ |
| 1-109 | F | Cl | H | $CH_3$ | $CH_3$ | $OCH_2C{\equiv}CH$ |
| 1-110 | H | Cl | H | $CH_3$ | $CH_3$ | $OCH(CH_3)C{\equiv}CH$ |
| 1-111 | H | Cl | H | $CH_3$ | $CH_3$ | $OCH_2C{\equiv}CBr$ |
| 1-112 | H | Cl | H | $CH_3$ | $CH_3$ | $OCH_2C{\equiv}CCl$ |
| 1-113 | H | Cl | H | $CH_3$ | $CH_3$ | $OCH_2C{\equiv}CCH_2Cl$ |
| 1-114 | H | Cl | H | $CH_3$ | $CH_3$ | $OCH_2CN$ |
| 1-115 | H | Cl | H | $CH_3$ | $CH_3$ | $OCH_2OCH_3$ |
| 1-116 | H | Cl | H | $CH_3$ | $CH_3$ | $OCH_2OC_2H_5$ |
| 1-117 | H | Cl | H | $CH_3$ | $CH_3$ | $OCH_2SCH_3$ |
| 1-118 | H | Cl | H | $CH_3$ | $CH_3$ | $OCH_2COOCH_3$ |
| 1-119 | H | Cl | H | $CH_3$ | $CH_3$ | $OCH_2COOC_2H_5$ |
| 1-120 | H | Cl | H | $CH_3$ | $CH_3$ | $OCH_2COO^nC_3H_7$ |
| 1-121 | H | Cl | H | $CH_3$ | $CH_3$ | $OCH_2COO^nC_4H_9$ |
| 1-122 | H | Cl | H | $CH_3$ | $CH_3$ | $OCH_2COO^nC_5H_{11}$ |
| 1-123 | H | Cl | H | $CH_3$ | $CH_3$ | $OCH_2COO^iC_3H_7$ |
| 1-124 | H | Cl | H | $CH_3$ | $CH_3$ | $OCH_2COO^cC_5H_9$ |
| 1-125 | H | Cl | H | $CH_3$ | $CH_3$ | $OCH_2COO^cC_6H_{11}$ |
| 1-126 | H | Cl | H | $CH_3$ | $CH_3$ | $OCH(CH_3)COOCH_3$ |
| 1-127 | H | Cl | H | $CH_3$ | $CH_3$ | $OCH(CH_3)COOC_2H_5$ |
| 1-128 | H | Cl | H | $CH_3$ | $CH_3$ | $OCH(CH_3)COO^nC_3H_7$ |
| 1-129 | H | Cl | H | $CH_3$ | $CH_3$ | $OCH(CH_3)COO^nC_4H_9$ |
| 1-130 | H | Cl | H | $CH_3$ | $CH_3$ | $OCH(CH_3)COO^nC_5H_{11}$ |
| 1-131 | H | Cl | H | $CH_3$ | $CH_3$ | $OCH(CH_3)COO^iC_3H_7$ |
| 1-132 | H | Cl | H | $CH_3$ | $CH_3$ | $OCH(CH_3)COO^cC_5H_9$ |
| 1-133 | H | Cl | H | $CH_3$ | $CH_3$ | $OCH(CH_3)COO^cC_6H_{11}$ |
| 1-134 | H | Cl | H | $CH_3$ | $CH_3$ | $OCH_2CON(CH_3)_2$ |
| 1-135 | H | Cl | H | $CH_3$ | $CH_3$ | $OCH_2CON(C_2H_5)_2$ |
| 1-136 | H | Cl | H | $CH_3$ | $CH_3$ | $OCH(CH_3)_2C_2H_5$ |
| 1-137 | H | Cl | H | $CH_3$ | $CH_3$ | $OCH(CH_3)CON(CH_3)_2$ |
| 1-138 | H | Cl | H | $CH_3$ | $CH_3$ | $OCH(CH_3)CON(C_2H_5)_2$ |
| 1-139 | H | Cl | H | $CH_3$ | $CH_3$ | $OCH(CH_3)CON(CH_3)C_2H_5$ |
| 1-140 | H | Cl | H | $CH_3$ | $CH_3$ | $OCH_2COON(CH_3)_2$ |
| 1-141 | H | Cl | H | $CH_3$ | $CH_3$ | $OCH_2COON(C_2H_5)_2$ |
| 1-142 | H | Cl | H | $CH_3$ | $CH_3$ | $OCH(CH_3)COON(CH_3)_2$ |
| 1-143 | H | Cl | H | $CH_3$ | $CH_3$ | $OCH(CH_3)COON(C_2H_5)_2$ |

TABLE 1-continued

Compounds of the formula:

| Compound No. | X | Y | R¹ | R² | R³ | B |
|---|---|---|---|---|---|---|
| 1-144 | F | Cl | H | $CH_3$ | $CH_3$ | $OCH_3$ |
| 1-145 | F | Cl | H | $CH_3$ | $CH_3$ | $OC_2H_5$ |
| 1-146 | F | Cl | H | $CH_3$ | $CH_3$ | $O^iC_3H_7$ |
| 1-147 | F | Cl | H | $CH_3$ | $CH_3$ | $O^nC_3H_7$ |
| 1-148 | F | Cl | H | $CH_3$ | $CH_3$ | $OCH_2CH_2Cl$ |
| 1-149 | F | Cl | H | $CH_3$ | $CH_3$ | $OCF_2CF_2H$ |
| 1-150 | F | Cl | H | $CH_3$ | $CH_3$ | $O^cC_5H_9$ |
| 1-151 | F | Cl | H | $CH_3$ | $CH_3$ | $O^cC_6H_{11}$ |
| 1-152 | F | Cl | H | $CH_3$ | $CH_3$ | $OCH_2CH=CH_2$ |
| 1-153 | F | Cl | H | $CH_3$ | $CH_3$ | $OCH_2CCl=CH_2$ |
| 1-154 | F | Cl | H | $CH_3$ | $CH_3$ | $OCH_2CCl=CHCl$ |
| 1-155 | F | Cl | H | $CH_3$ | $CH_3$ | $OCH(CH_3)CH=CH_2$ |
| 1-156 | F | Cl | H | $CH_3$ | $CH_3$ | $OCH_2C\equiv CH$ |
| 1-157 | F | Cl | H | $CH_3$ | $CH_3$ | $OCH(CH_3)C\equiv CH$ |
| 1-158 | F | Cl | H | $CH_3$ | $CH_3$ | $OCH_2C\equiv CBr$ |
| 1-159 | F | Cl | H | $CH_3$ | $CH_3$ | $OCH_2C\equiv CCl$ |
| 1-160 | F | Cl | H | $CH_3$ | $CH_3$ | $OCH_2C\equiv CCH_2Cl$ |
| 1-161 | F | Cl | H | $CH_3$ | $CH_3$ | $OCH_2CN$ |
| 1-162 | F | Cl | H | $CH_3$ | $CH_3$ | $OCH_2OCH_3$ |
| 1-163 | F | Cl | H | $CH_3$ | $CH_3$ | $OCH_2OC_2H_5$ |
| 1-164 | F | Cl | H | $CH_3$ | $CH_3$ | $OCH_2SCH_3$ |
| 1-165 | F | Cl | H | $CH_3$ | $CH_3$ | $OCH_2COOCH_3$ |
| 1-166 | F | Cl | H | $CH_3$ | $CH_3$ | $OCH_2COOC_2H_5$ |
| 1-167 | F | Cl | H | $CH_3$ | $CH_3$ | $OCH_2COO^nC_3H_7$ |
| 1-168 | F | Cl | H | $CH_3$ | $CH_3$ | $OCH_2COO^nC_4H_9$ |
| 1-169 | F | Cl | H | $CH_3$ | $CH_3$ | $OCH_2COO^nC_5H_{11}$ |
| 1-170 | F | Cl | H | $CH_3$ | $CH_3$ | $OCH_2COO^iC_3H_7$ |
| 1-171 | F | Cl | H | $CH_3$ | $CH_3$ | $OCH_2COO^cC_5H_9$ |
| 1-172 | F | Cl | H | $CH_3$ | $CH_3$ | $OCH_2COO^cC_6H_{11}$ |
| 1-173 | F | Cl | H | $CH_3$ | $CH_3$ | $OCH(CH_3)COOCH_3$ |
| 1-174 | F | Cl | H | $CH_3$ | $CH_3$ | $OCH(CH_3)COOC_2H_5$ |
| 1-175 | F | Cl | H | $CH_3$ | $CH_3$ | $OCH(CH_3)COO^nC_3H_7$ |
| 1-176 | F | Cl | H | $CH_3$ | $CH_3$ | $OCH(CH_3)COO^nC_4H_9$ |
| 1-177 | F | Cl | H | $CH_3$ | $CH_3$ | $OCH(CH_3)COO^nC_5H_{11}$ |
| 1-178 | F | Cl | H | $CH_3$ | $CH_3$ | $OCH(CH_3)COO^iC_3H_7$ |
| 1-179 | F | Cl | H | $CH_3$ | $CH_3$ | $OCH(CH_3)COO^cC_5H_9$ |
| 1-180 | F | Cl | H | $CH_3$ | $CH_3$ | $OCH(CH_3)COO^cC_6H_{11}$ |
| 1-181 | F | Cl | H | $CH_3$ | $CH_3$ | $OCH_2CON(CH_3)_2$ |
| 1-182 | F | Cl | H | $CH_3$ | $CH_3$ | $OCH_2CON(C_2H_5)_2$ |
| 1-183 | F | Cl | H | $CH_3$ | $CH_3$ | $OCH_2CON(CH_3)C_2H_5$ |
| 1-184 | F | Cl | H | $CH_3$ | $CH_3$ | $OCH(CH_3)CON(CH_3)_2$ |
| 1-185 | F | Cl | H | $CH_3$ | $CH_3$ | $OCH(CH_3)CON(C_2H_5)_2$ |
| 1-186 | F | Cl | H | $CH_3$ | $CH_3$ | $OCH(CH_3)CON(CH_3)C_2H_5$ |
| 1-187 | F | Cl | H | $CH_3$ | $CH_3$ | $OCH_2COON(CH_3)_2$ |
| 1-188 | F | Cl | H | $CH_3$ | $CH_3$ | $OCH_2COON(C_2H_5)_2$ |
| 1-189 | F | Cl | H | $CH_3$ | $CH_3$ | $OCH(CH_3)COON(CH_3)_2$ |
| 1-190 | F | Cl | H | $CH_3$ | $CH_3$ | $OCH(CH_3)COON(C_2H_5)_2$ |
| 1-191 | H | F | H | $CH_3$ | $CH_3$ | SH |
| 1-192 | H | Cl | H | $CH_3$ | $CH_3$ | SH |
| 1-193 | H | Br | H | $CH_3$ | $CH_3$ | SH |
| 1-194 | F | F | H | $CH_3$ | $CH_3$ | SH |
| 1-195 | F | Cl | H | $CH_3$ | $CH_3$ | SH |
| 1-196 | F | Br | H | $CH_3$ | $CH_3$ | SH |
| 1-197 | H | Cl | H | $CH_3$ | $CH_3$ | $SCH_3$ |
| 1-198 | H | Cl | H | $CH_3$ | $CH_3$ | $SC_2H_5$ |
| 1-199 | H | Cl | H | $CH_3$ | $CH_3$ | $S^iC_3H_7$ |
| 1-200 | H | Cl | H | $CH_3$ | $CH_3$ | $SCH_2CH_2Cl$ |
| 1-201 | H | Cl | H | $CH_3$ | $CH_3$ | $S^cC_5H_9$ |
| 1-202 | H | Cl | H | $CH_3$ | $CH_3$ | $S^cC_6H_{11}$ |
| 1-203 | H | Cl | H | $CH_3$ | $CH_3$ | $SCH_2CH=CH_2$ |
| 1-204 | H | Cl | H | $CH_3$ | $CH_3$ | $SCH_2CCl=CH_2$ |
| 1-205 | H | Cl | H | $CH_3$ | $CH_3$ | $SCH_2CCl=CHCl$ |
| 1-206 | H | Cl | H | $CH_3$ | $CH_3$ | $SCH(CH_3)CH=CH_2$ |
| 1-207 | H | Cl | H | $CH_3$ | $CH_3$ | $SCH_2C\equiv CH$ |
| 1-208 | H | Cl | H | $CH_3$ | $CH_3$ | $SCH(CH_3)C\equiv CH$ |
| 1-209 | H | Cl | H | $CH_3$ | $CH_3$ | $SCH_2COOCH_3$ |
| 1-210 | H | Cl | H | $CH_3$ | $CH_3$ | $SCH_2COOC_2H_5$ |
| 1-211 | H | Cl | H | $CH_3$ | $CH_3$ | $SCH_2COO^nC_3H_7$ |
| 1-212 | H | Cl | H | $CH_3$ | $CH_3$ | $SCH_2COO^nC_4H_9$ |
| 1-213 | H | Cl | H | $CH_3$ | $CH_3$ | $SCH_2COO^nC_5H_{11}$ |
| 1-214 | H | Cl | H | $CH_3$ | $CH_3$ | $SCH_2COO^iC_3H_7$ |
| 1-215 | H | Cl | H | $CH_3$ | $CH_3$ | $SCH_2COO^cC_5H_9$ |
| 1-216 | H | Cl | H | $CH_3$ | $CH_3$ | $SCH_2COO^cC_6H_{11}$ |
| 1-217 | H | Cl | H | $CH_3$ | $CH_3$ | $SCH(CH_3)COOCH_3$ |
| 1-218 | H | Cl | H | $CH_3$ | $CH_3$ | $SCH(CH_3)COOC_2H_5$ |
| 1-219 | H | Cl | H | $CH_3$ | $CH_3$ | $SCH(CH_3)COO^nC_3H_7$ |
| 1-220 | H | Cl | H | $CH_3$ | $CH_3$ | $SCH(CH_3)COO^nC_4H_9$ |
| 1-221 | H | Cl | H | $CH_3$ | $CH_3$ | $SCH(CH_3)COO^nC_5H_{11}$ |
| 1-222 | H | Cl | H | $CH_3$ | $CH_3$ | $SCH(CH_3)COO^iC_3H_7$ |
| 1-223 | H | Cl | H | $CH_3$ | $CH_3$ | $SCH(CH_3)COO^cC_5H_9$ |
| 1-224 | H | Cl | H | $CH_3$ | $CH_3$ | $SCH(CH_3)COO^cC_6H_{11}$ |
| 1-225 | H | Cl | H | $CH_3$ | $CH_3$ | $SCH_2CON(CH_3)_2$ |
| 1-226 | H | Cl | H | $CH_3$ | $CH_3$ | $SCH_2CON(C_2H_5)_2$ |
| 1-227 | H | Cl | H | $CH_3$ | $CH_3$ | $SCH_2CON(tetramethylene)$ |
| 1-228 | H | Cl | H | $CH_3$ | $CH_3$ | $SCH_2CON(pentamethylene)$ |
| 1-229 | H | Cl | H | $CH_3$ | $CH_3$ | $SCH_2CON(ethyleneoxyethylene)$ |
| 1-230 | H | Cl | H | $CH_3$ | $CH_3$ | $SCH(CH_3)CON(CH_3)_2$ |
| 1-231 | H | Cl | H | $CH_3$ | $CH_3$ | $SCH(CH_3)CON(C_2H_5)_2$ |
| 1-232 | H | Cl | H | $CH_3$ | $CH_3$ | $SCH(CH_3)CON(tetramethylene)$ |
| 1-233 | H | Cl | H | $CH_3$ | $CH_3$ | $SCH(CH_3)CON(pentamethylene)$ |
| 1-234 | F | Cl | H | $CH_3$ | $CH_3$ | $SCH_3$ |
| 1-235 | F | Cl | H | $CH_3$ | $CH_3$ | $SC_2H_5$ |
| 1-236 | F | Cl | H | $CH_3$ | $CH_3$ | $S^iC_3H_7$ |
| 1-237 | F | Cl | H | $CH_3$ | $CH_3$ | $SCH_2CH_2Cl$ |
| 1-238 | F | Cl | H | $CH_3$ | $CH_3$ | $S^cC_5H_9$ |
| 1-239 | F | Cl | H | $CH_3$ | $CH_3$ | $S^cC_6H_{11}$ |
| 1-240 | F | Cl | H | $CH_3$ | $CH_3$ | $SCH_2CH=CH_2$ |
| 1-241 | F | Cl | H | $CH_3$ | $CH_3$ | $SCH_2CCl=CH_2$ |
| 1-242 | F | Cl | H | $CH_3$ | $CH_3$ | $SCH_2CCl=CHCl$ |
| 1-243 | F | Cl | H | $CH_3$ | $CH_3$ | $SCH(CH_3)CH=CH_2$ |
| 1-244 | F | Cl | H | $CH_3$ | $CH_3$ | $SCH_2C\equiv CH$ |
| 1-245 | F | Cl | H | $CH_3$ | $CH_3$ | $SCH(CH_3)C\equiv CH$ |
| 1-246 | F | Cl | H | $CH_3$ | $CH_3$ | $SCH_2COOCH_3$ |
| 1-247 | F | Cl | H | $CH_3$ | $CH_3$ | $SCH_2COOC_2H_5$ |
| 1-248 | F | Cl | H | $CH_3$ | $CH_3$ | $SCH_2COO^nC_3H_7$ |
| 1-249 | F | Cl | H | $CH_3$ | $CH_3$ | $SCH_2COO^nC_4H_9$ |
| 1-250 | F | Cl | H | $CH_3$ | $CH_3$ | $SCH_2COO^nC_5H_{11}$ |
| 1-251 | F | Cl | H | $CH_3$ | $CH_3$ | $SCH_2COO^iC_3H_7$ |
| 1-252 | F | Cl | H | $CH_3$ | $CH_3$ | $SCH_2COO^cC_5H_9$ |
| 1-253 | F | Cl | H | $CH_3$ | $CH_3$ | $SCH_2COO^cC_6H_{11}$ |
| 1-254 | F | Cl | H | $CH_3$ | $CH_3$ | $SCH(CH_3)COOCH_3$ |
| 1-255 | F | Cl | H | $CH_3$ | $CH_3$ | $SCH(CH_3)COOC_2H_5$ |
| 1-256 | F | Cl | H | $CH_3$ | $CH_3$ | $SCH(CH_3)COO^nC_3H_7$ |
| 1-257 | F | Cl | H | $CH_3$ | $CH_3$ | $SCH(CH_3)COO^nC_4H_9$ |
| 1-258 | F | Cl | H | $CH_3$ | $CH_3$ | $SCH(CH_3)COO^nC_5H_{11}$ |
| 1-259 | F | Cl | H | $CH_3$ | $CH_3$ | $SCH(CH_3)COO^iC_3H_7$ |
| 1-260 | F | Cl | H | $CH_3$ | $CH_3$ | $SCH(CH_3)COO^cC_5H_9$ |
| 1-261 | F | Cl | H | $CH_3$ | $CH_3$ | $SCH(CH_3)COO^cC_6H_{11}$ |
| 1-262 | F | Cl | H | $CH_3$ | $CH_3$ | $SCH_2CON(CH_3)_2$ |
| 1-263 | F | Cl | H | $CH_3$ | $CH_3$ | $SCH_2CON(C_2H_5)_2$ |
| 1-264 | F | Cl | H | $CH_3$ | $CH_3$ | $SCH_2CON(tetramethylene)$ |
| 1-265 | F | Cl | H | $CH_3$ | $CH_3$ | $SCH_2CON(penta-$ |

TABLE 1-continued

Compounds of the formula:

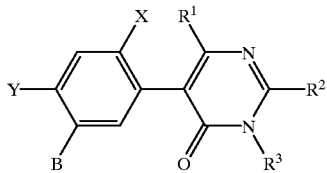 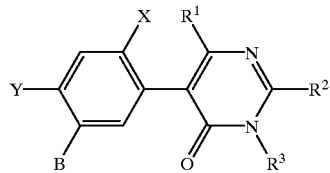

| Compound No. | X | Y | R¹ | R² | R³ | B |
|---|---|---|---|---|---|---|
| 1-266 | F | Cl | H | $CH_3$ | $CH_3$ | $SCH_2CON$(ethyleneoxy-ethylene) |
| 1-267 | F | Cl | H | $CH_3$ | $CH_3$ | $SCH(CH_3)CON(CH_3)_2$ |
| 1-268 | F | Cl | H | $CH_3$ | $CH_3$ | $SCH(CH_3)CON(C_2H_5)_2$ |
| 1-269 | F | Cl | H | $CH_3$ | $CH_3$ | $SCH(CH_3)CON$(tetra-methylene) |
| 1-270 | F | Cl | H | $CH_3$ | $CH_3$ | $SCH(CH_3)CON$(penta-methylene) |
| 1-271 | H | F | H | $CH_3$ | $CH_3$ | $SO_2Cl$ |
| 1-272 | H | Cl | H | $CH_3$ | $CH_3$ | $SO_2Cl$ |
| 1-273 | H | Br | H | $CH_3$ | $CH_3$ | $SO_2Cl$ |
| 1-274 | F | F | H | $CH_3$ | $CH_3$ | $SO_2Cl$ |
| 1-275 | F | Cl | H | $CH_3$ | $CH_3$ | $SO_2Cl$ |
| 1-276 | F | Br | H | $CH_3$ | $CH_3$ | $SO_2Cl$ |
| 1-277 | H | Cl | H | $CH_3$ | $CH_3$ | $SO_2OCH_3$ |
| 1-278 | H | Cl | H | $CH_3$ | $CH_3$ | $SO_2OC_2H_5$ |
| 1-279 | H | Cl | H | $CH_3$ | $CH_3$ | $SO_2O^iC_3H_7$ |
| 1-280 | H | Cl | H | $CH_3$ | $CH_3$ | $SO_2OCH_2CH=CH_2$ |
| 1-281 | F | Cl | H | $CH_3$ | $CH_3$ | $SO_2OCH_3$ |
| 1-282 | F | Cl | H | $CH_3$ | $CH_3$ | $SO_2OC_2H_5$ |
| 1-283 | F | Cl | H | $CH_3$ | $CH_3$ | $SO_2O^iC_3H_7$ |
| 1-284 | F | Cl | H | $CH_3$ | $CH_3$ | $SO_2OCH_2CH=CH_2$ |
| 1-285 | H | Cl | H | $CH_3$ | $CH_3$ | $SO_2N(CH_3)_2$ |
| 1-286 | H | Cl | H | $CH_3$ | $CH_3$ | $SO_2N(C_2H_5)_2$ |
| 1-287 | F | Cl | H | $CH_3$ | $CH_3$ | $SO_2N(CH_3)_2$ |
| 1-288 | F | Cl | H | $CH_3$ | $CH_3$ | $SO_2N(C_2H_5)_2$ |
| 1-289 | H | Cl | H | $CH_3$ | $CH_3$ | COOH |
| 1-290 | H | Cl | H | $CH_3$ | $CH_3$ | $COOCH_3$ |
| 1-291 | H | Cl | H | $CH_3$ | $CH_3$ | $COOC_2H_5$ |
| 1-292 | H | Cl | H | $CH_3$ | $CH_3$ | $COO^nC_3H_7$ |
| 1-293 | H | Cl | H | $CH_3$ | $CH_3$ | $COO^nC_4H_9$ |
| 1-294 | H | Cl | H | $CH_3$ | $CH_3$ | $COO^nC_5H_{11}$ |
| 1-295 | H | Cl | H | $CH_3$ | $CH_3$ | $COO^iC_3H_7$ |
| 1-296 | H | Cl | H | $CH_3$ | $CH_3$ | $COOCH_2CH_2Cl$ |
| 1-297 | H | Cl | H | $CH_3$ | $CH_3$ | $COOCH_2CH_2Br$ |
| 1-298 | H | Cl | H | $CH_3$ | $CH_3$ | $CON(CH_3)_2$ |
| 1-299 | H | Cl | H | $CH_3$ | $CH_3$ | $CONHCH_3$ |
| 1-300 | H | Cl | H | $CH_3$ | $CH_3$ | $CON(C_2H_5)_2$ |
| 1-301 | H | Cl | H | $CH_3$ | $CH_3$ | $CONHC_2H_5$ |
| 1-302 | H | Cl | H | $CH_3$ | $CH_3$ | $COCH_3$ |
| 1-303 | H | Cl | H | $CH_3$ | $CH_3$ | $COC_2H_5$ |
| 1-304 | H | Cl | H | $CH_3$ | $CH_3$ | $COCH_2Cl$ |
| 1-305 | H | Cl | H | $CH_3$ | $CH_3$ | CHO |
| 1-306 | H | Cl | H | $CH_3$ | $CH_3$ | $CH=CHCOOCH_3$ |
| 1-307 | H | Cl | H | $CH_3$ | $CH_3$ | $CH=CHCOOC_2H_5$ |
| 1-308 | H | Cl | H | $CH_3$ | $CH_3$ | $CH_2CH_2COOCH_3$ |
| 1-309 | H | Cl | H | $CH_3$ | $CH_3$ | $CH_2CH_2COOC_2H_5$ |
| 1-310 | F | Cl | H | $CH_3$ | $CH_3$ | COOH |
| 1-311 | F | Cl | H | $CH_3$ | $CH_3$ | $COOCH_3$ |
| 1-312 | F | Cl | H | $CH_3$ | $CH_3$ | $COOC_2H_5$ |
| 1-313 | F | Cl | H | $CH_3$ | $CH_3$ | $COO^nC_3H_7$ |
| 1-314 | F | Cl | H | $CH_3$ | $CH_3$ | $COO^nC_4H_9$ |
| 1-315 | F | Cl | H | $CH_3$ | $CH_3$ | $COO^nC_5H_{11}$ |
| 1-316 | F | Cl | H | $CH_3$ | $CH_3$ | $COO^iC_3H_7$ |
| 1-317 | F | Cl | H | $CH_3$ | $CH_3$ | $COOCH_2CH_2Cl$ |
| 1-318 | F | Cl | H | $CH_3$ | $CH_3$ | $COOCH_2CH_2Br$ |
| 1-319 | F | Cl | H | $CH_3$ | $CH_3$ | $CON(CH_3)_2$ |
| 1-320 | F | Cl | H | $CH_3$ | $CH_3$ | $CONHCH_3$ |
| 1-321 | F | Cl | H | $CH_3$ | $CH_3$ | $CON(C_2H_5)_2$ |
| 1-322 | F | Cl | H | $CH_3$ | $CH_3$ | $CONHC_2H_5$ |
| 1-323 | F | Cl | H | $CH_3$ | $CH_3$ | $COCH_3$ |
| 1-324 | F | Cl | H | $CH_3$ | $CH_3$ | $COC_2H_5$ |
| 1-325 | F | Cl | H | $CH_3$ | $CH_3$ | $COCH_2Cl$ |
| 1-326 | F | Cl | H | $CH_3$ | $CH_3$ | CHO |
| 1-327 | F | Cl | H | $CH_3$ | $CH_3$ | $CH=CHCOOCH_3$ |
| 1-328 | F | Cl | H | $CH_3$ | $CH_3$ | $CH=CHCOOC_2H_5$ |
| 1-329 | F | Cl | H | $CH_3$ | $CH_3$ | $CH_2CH_2COOCH_3$ |
| 1-330 | F | Cl | H | $CH_3$ | $CH_3$ | $CH_2CH_2COOC_2H_5$ |
| 1-331 | H | F | H | $CF_3$ | $C_2H_5$ | H |
| 1-332 | H | Cl | H | $CF_3$ | $C_2H_5$ | H |
| 1-333 | H | Br | H | $CF_3$ | $C_2H_5$ | H |
| 1-334 | H | F | H | $CF_3$ | $CH_3$ | H |
| 1-335 | H | Cl | H | $CF_3$ | $CH_3$ | H |
| 1-336 | H | Br | H | $CF_3$ | $CH_3$ | H |
| 1-337 | F | F | H | $CF_3$ | $C_2H_5$ | H |
| 1-338 | F | Cl | H | $CF_3$ | $C_2H_5$ | H |
| 1-339 | F | Br | H | $CF_3$ | $C_2H_5$ | H |
| 1-340 | F | F | H | $CF_3$ | $CH_3$ | H |
| 1-341 | F | Cl | H | $CF_3$ | $CH_3$ | H |
| 1-342 | F | Br | H | $CF_3$ | $CH_3$ | H |
| 1-343 | H | F | H | $CF_3$ | $CH_3$ | $NO_2$ |
| 1-344 | H | Cl | H | $CF_3$ | $CH_3$ | $NO_2$ |
| 1-345 | H | Br | H | $CF_3$ | $CH_3$ | $NO_2$ |
| 1-346 | F | F | H | $CF_3$ | $CH_3$ | $NO_2$ |
| 1-347 | F | Cl | H | $CF_3$ | $CH_3$ | $NO_2$ |
| 1-348 | F | Br | H | $CF_3$ | $CH_3$ | $NO_2$ |
| 1-349 | H | F | H | $CF_3$ | $CH_3$ | $NH_2$ |
| 1-350 | H | Cl | H | $CF_3$ | $CH_3$ | $NH_2$ |
| 1-351 | H | Br | H | $CF_3$ | $CH_3$ | $NH_2$ |
| 1-352 | F | F | H | $CF_3$ | $CH_3$ | $NH_2$ |
| 1-353 | F | Cl | H | $CF_3$ | $CH_3$ | $NH_2$ |
| 1-354 | H | Cl | H | $CF_3$ | $CH_3$ | $NHCH(CH_3)COOCH_3$ |
| 1-355 | H | Cl | H | $CF_3$ | $CH_3$ | $NHCH(CH_3)COOC_2H_5$ |
| 1-356 | H | Cl | H | $CF_3$ | $CH_3$ | $NHCH(CH_3)COO^nC_3H_7$ |
| 1-357 | H | Cl | H | $CF_3$ | $CH_3$ | $NHCH(CH_3)COO^nC_4H_9$ |
| 1-358 | H | Cl | H | $CF_3$ | $CH_3$ | $NHCH(CH_3)COO^nC_5H_{11}$ |
| 1-359 | H | Cl | H | $CF_3$ | $CH_3$ | $NHCH(CH_3)COO^iC_3H_7$ |
| 1-360 | H | Cl | H | $CF_3$ | $CH_3$ | $NHCH(CH_3)COO^cC_5H_9$ |
| 1-361 | H | Cl | H | $CF_3$ | $CH_3$ | $NHCH(CH_3)COO^cC_6H_{11}$ |
| 1-362 | F | Cl | H | $CF_3$ | $CH_3$ | $NHCH_3$ |
| 1-363 | F | Cl | H | $CF_3$ | $CH_3$ | $NHC_2H_5$ |
| 1-364 | F | Cl | H | $CF_3$ | $CH_3$ | $NHCH_2CH=CH_2$ |
| 1-365 | F | Cl | H | $CF_3$ | $CH_3$ | $NHCH_2C\equiv CH$ |
| 1-366 | F | Cl | H | $CF_3$ | $CH_3$ | $NHCH(CH_3)C\equiv CH$ |
| 1-367 | F | Cl | H | $CF_3$ | $CH_3$ | $NHSO_2CH_3$ |
| 1-368 | F | Cl | H | $CF_3$ | $CH_3$ | $NHSO_2C_2H_5$ |
| 1-369 | F | Cl | H | $CF_3$ | $CH_3$ | $NHSO_2CH_2Cl$ |
| 1-370 | F | Cl | H | $CF_3$ | $CH_3$ | $NHSO_2CF_3$ |
| 1-371 | F | Cl | H | $CF_3$ | $CH_3$ | $N(CH_3)SO_2CH_3$ |
| 1-372 | F | Cl | H | $CF_3$ | $CH_3$ | $N(CH_2C\equiv CH)SO_2CH_3$ |
| 1-373 | F | Cl | H | $CF_3$ | $CH_3$ | $NHCOOCH_3$ |
| 1-374 | F | Cl | H | $CF_3$ | $CH_3$ | $NHCOOC_2H_5$ |
| 1-375 | F | Cl | H | $CF_3$ | $CH_3$ | $NHCOO^nC_3H_7$ |
| 1-376 | F | Cl | H | $CF_3$ | $CH_3$ | $NHCOO^iC_3H_7$ |
| 1-377 | F | Cl | H | $CF_3$ | $CH_3$ | $NHCOO^nC_4H_9$ |
| 1-378 | F | Cl | H | $CF_3$ | $CH_3$ | $NHCOO^nC_5H_{11}$ |
| 1-379 | F | Cl | H | $CF_3$ | $CH_3$ | $NHCH_2COOCH_3$ |
| 1-380 | F | Cl | H | $CF_3$ | $CH_3$ | $NHCH_2COOC_2H_5$ |
| 1-381 | F | Cl | H | $CF_3$ | $CH_3$ | $NHCH_2COO^nC_3H_7$ |
| 1-382 | F | Cl | H | $CF_3$ | $CH_3$ | $NHCH_2COO^nC_4H_9$ |
| 1-383 | F | Cl | H | $CF_3$ | $CH_3$ | $NHCH_2COO^nC_5H_{11}$ |
| 1-384 | F | Cl | H | $CF_3$ | $CH_3$ | $NHCH_2COO^iC_3H_7$ |
| 1-385 | F | Cl | H | $CF_3$ | $CH_3$ | $NHCH_2COO^cC_5H_9$ |
| 1-386 | F | Br | H | $CF_3$ | $CH_3$ | $NH_2$ |
| 1-387 | H | F | H | $CF_3$ | $CH_3$ | OH |

TABLE 1-continued

Compounds of the formula:

| Compound No. | X | Y | R¹ | R² | R³ | B |
|---|---|---|---|---|---|---|
| 1-388 | H | Cl | H | $CF_3$ | $CH_3$ | OH |
| 1-389 | H | Br | H | $CF_3$ | $CH_3$ | OH |
| 1-390 | F | F | H | $CF_3$ | $CH_3$ | OH |
| 1-391 | F | Cl | H | $CF_3$ | $CH_3$ | OH |
| 1-392 | F | Br | H | $CF_3$ | $CH_3$ | OH |
| 1-393 | H | Cl | H | $CF_3$ | $CH_3$ | $NHCH_3$ |
| 1-394 | H | Cl | H | $CF_3$ | $CH_3$ | $NHC_2H_5$ |
| 1-395 | H | Cl | H | $CF_3$ | $CH_3$ | $NHCH_2CH=CH_2$ |
| 1-396 | H | Cl | H | $CF_3$ | $CH_3$ | $NHCH_2C\equiv CH$ |
| 1-397 | H | Cl | H | $CF_3$ | $CH_3$ | $NHCH(CH_3)C\equiv CH$ |
| 1-398 | H | Cl | H | $CF_3$ | $CH_3$ | $NHSO_2CH_3$ |
| 1-399 | H | Cl | H | $CF_3$ | $CH_3$ | $NHSO_2C_2H_5$ |
| 1-400 | H | Cl | H | $CF_3$ | $CH_3$ | $NHSO_2CH_2Cl$ |
| 1-401 | H | Cl | H | $CF_3$ | $CH_3$ | $NHSO_2CF_3$ |
| 1-402 | H | Cl | H | $CF_3$ | $CH_3$ | $N(CH_3)SO_2CH_3$ |
| 1-403 | H | Cl | H | $CF_3$ | $CH_3$ | $N(CH_2C\equiv CH)SO_2CH_3$ |
| 1-404 | H | Cl | H | $CF_3$ | $CH_3$ | $NHCOOCH_3$ |
| 1-405 | H | Cl | H | $CF_3$ | $CH_3$ | $NHCOOC_2H_5$ |
| 1-406 | H | Cl | H | $CF_3$ | $CH_3$ | $NHCOO^nC_3H_7$ |
| 1-407 | H | Cl | H | $CF_3$ | $CH_3$ | $NHCOO^iC_3H_7$ |
| 1-408 | H | Cl | H | $CF_3$ | $CH_3$ | $NHCOO^nC_4H_9$ |
| 1-409 | H | Cl | H | $CF_3$ | $CH_3$ | $NHCOO^nC_5H_{11}$ |
| 1-410 | H | Cl | H | $CF_3$ | $CH_3$ | $NHCH_2COOCH_3$ |
| 1-411 | H | Cl | H | $CF_3$ | $CH_3$ | $NHCH_2COOC_2H_5$ |
| 1-412 | H | Cl | H | $CF_3$ | $CH_3$ | $NHCH_2COO^nC_3H_7$ |
| 1-413 | H | Cl | H | $CF_3$ | $CH_3$ | $NHCH_2COO^nC_4H_9$ |
| 1-414 | H | Cl | H | $CF_3$ | $CH_3$ | $NHCH_2COO^nC_5H_{11}$ |
| 1-415 | H | Cl | H | $CF_3$ | $CH_3$ | $NHCH_2COO^iC_3H_7$ |
| 1-416 | H | Cl | H | $CF_3$ | $CH_3$ | $NHCH_2COO^cC_5H_9$ |
| 1-417 | H | Cl | H | $CF_3$ | $CH_3$ | $NHCH_2COO^cC_6H_{11}$ |
| 1-418 | F | Cl | H | $CF_3$ | $CH_3$ | $NHCH_2COO^cC_6H_{11}$ |
| 1-419 | F | Cl | H | $CF_3$ | $CH_3$ | $NHCH(CH_3)COOCH_3$ |
| 1-420 | F | Cl | H | $CF_3$ | $CH_3$ | $NHCH(CH_3)COOC_2H_5$ |
| 1-421 | F | Cl | H | $CF_3$ | $CH_3$ | $NHCH(CH_3)COO^nC_3H_7$ |
| 1-422 | F | Cl | H | $CF_3$ | $CH_3$ | $NHCH(CH_3)COO^nC_4H_9$ |
| 1-423 | F | Cl | H | $CF_3$ | $CH_3$ | $NHCH(CH_3)COO^nC_5H_{11}$ |
| 1-424 | F | Cl | H | $CF_3$ | $CH_3$ | $NHCH(CH_3)COO^iC_3H_7$ |
| 1-425 | F | Cl | H | $CF_3$ | $CH_3$ | $NHCH(CH_3)COO^cC_5H_9$ |
| 1-426 | F | Cl | H | $CF_3$ | $CH_3$ | $NHCH(CH_3)COO^cC_6H_{11}$ |
| 1-427 | H | Cl | H | $CF_3$ | $CH_3$ | $OCH_3$ |
| 1-428 | H | Cl | H | $CF_3$ | $CH_3$ | $OC_2H_5$ |
| 1-429 | H | Cl | H | $CF_3$ | $CH_3$ | $O^iC_3H_7$ |
| 1-430 | H | Cl | H | $CF_3$ | $CH_3$ | $O^nC_3H_7$ |
| 1-431 | H | Cl | H | $CF_3$ | $CH_3$ | $OCH_2CH_2Cl$ |
| 1-432 | H | Cl | H | $CF_3$ | $CH_3$ | $OCF_2CF_2H$ |
| 1-433 | H | Cl | H | $CF_3$ | $CH_3$ | $O^cC_5H_9$ |
| 1-434 | H | Cl | H | $CF_3$ | $CH_3$ | $O^cC_6H_{11}$ |
| 1-435 | H | Cl | H | $CF_3$ | $CH_3$ | $OCH_2CH=CH_2$ |
| 1-436 | H | Cl | H | $CF_3$ | $CH_3$ | $OCH_2CCl=CH_2$ |
| 1-437 | H | Cl | H | $CF_3$ | $CH_3$ | $OCH_2CCl=CHCl$ |
| 1-438 | H | Cl | H | $CF_3$ | $CH_3$ | $OCH(CH_3)CH=CH_2$ |
| 1-439 | H | Cl | H | $CF_3$ | $CH_3$ | $OCH_2C\equiv CH$ |
| 1-440 | H | Cl | H | $CF_3$ | $CH_3$ | $OCH(CH_3)C\equiv CH$ |
| 1-441 | H | Cl | H | $CF_3$ | $CH_3$ | $OCH_2C\equiv CBr$ |
| 1-442 | H | Cl | H | $CF_3$ | $CH_3$ | $OCH_2C\equiv CCl$ |
| 1-443 | H | Cl | H | $CF_3$ | $CH_3$ | $OCH_2C\equiv CCH_2Cl$ |
| 1-444 | H | Cl | H | $CF_3$ | $CH_3$ | $OCH_2CN$ |
| 1-445 | H | Cl | H | $CF_3$ | $CH_3$ | $OCH_2OCH_3$ |
| 1-446 | H | Cl | H | $CF_3$ | $CH_3$ | $OCH_2OC_2H_5$ |
| 1-447 | H | Cl | H | $CF_3$ | $CH_3$ | $OCH_2SCH_3$ |
| 1-448 | H | Cl | H | $CF_3$ | $CH_3$ | $OCH_2COOCH_3$ |
| 1-449 | H | Cl | H | $CF_3$ | $CH_3$ | $OCH_2COOC_2H_5$ |
| 1-450 | H | Cl | H | $CF_3$ | $CH_3$ | $OCH_2COO^nC_3H_7$ |
| 1-451 | H | Cl | H | $CF_3$ | $CH_3$ | $OCH_2COO^nC_4H_9$ |
| 1-452 | H | Cl | H | $CF_3$ | $CH_3$ | $OCH_2COO^nC_5H_{11}$ |
| 1-453 | H | Cl | H | $CF_3$ | $CH_3$ | $OCH_2COO^iC_3H_7$ |
| 1-454 | H | Cl | H | $CF_3$ | $CH_3$ | $OCH_2COO^cC_5H_9$ |
| 1-455 | H | Cl | H | $CF_3$ | $CH_3$ | $OCH_2COO^cC_6H_{11}$ |
| 1-456 | H | Cl | H | $CF_3$ | $CH_3$ | $OCH(CH_3)COOCH_3$ |
| 1-457 | H | Cl | H | $CF_3$ | $CH_3$ | $OCH(CH_3)COOC_2H_5$ |
| 1-458 | H | Cl | H | $CF_3$ | $CH_3$ | $OCH(CH_3)COO^nC_3H_7$ |
| 1-459 | H | Cl | H | $CF_3$ | $CH_3$ | $OCH(CH_3)COO^nC_4H_9$ |
| 1-460 | H | Cl | H | $CF_3$ | $CH_3$ | $OCH(CH_3)COO^nC_5H_{11}$ |
| 1-461 | H | Cl | H | $CF_3$ | $CH_3$ | $OCH(CH_3)COO^iC_3H_7$ |
| 1-462 | H | Cl | H | $CF_3$ | $CH_3$ | $OCH(CH_3)COO^cC_5H_9$ |
| 1-463 | H | Cl | H | $CF_3$ | $CH_3$ | $OCH(CH_3)COO^cC_6H_{11}$ |
| 1-464 | H | Cl | H | $CF_3$ | $CH_3$ | $OCH_2CON(CH_3)_2$ |
| 1-465 | H | Cl | H | $CF_3$ | $CH_3$ | $OCH_2CON(C_2H_5)_2$ |
| 1-466 | H | Cl | H | $CF_3$ | $CH_3$ | $OCH_2CON(CH_3)C_2H_5$ |
| 1-467 | H | Cl | H | $CF_3$ | $CH_3$ | $OCH(CH_3)CON(CH_3)_2$ |
| 1-468 | H | Cl | H | $CF_3$ | $CH_3$ | $OCH(CH_3)CON(C_2H_5)_2$ |
| 1-469 | H | Cl | H | $CF_3$ | $CH_3$ | $OCH(CH_3)CON(CH_3)C_2H_5$ |
| 1-470 | H | Cl | H | $CF_3$ | $CH_3$ | $OCH_2COON(CH_3)_2$ |
| 1-471 | H | Cl | H | $CF_3$ | $CH_3$ | $OCH_2COON(C_2H_5)_2$ |
| 1-472 | H | Cl | H | $CF_3$ | $CH_3$ | $OCH(CH_3)COON(CH_3)_2$ |
| 1-473 | H | Cl | H | $CF_3$ | $CH_3$ | $OCH(CH_3)COON(C_2H_5)_2$ |
| 1-474 | F | Cl | H | $CF_3$ | $CH_3$ | $OCH_3$ |
| 1-475 | F | Cl | H | $CF_3$ | $CH_3$ | $OC_2H_5$ |
| 1-476 | F | Cl | H | $CF_3$ | $CH_3$ | $O^iC_3H_7$ |
| 1-477 | F | Cl | H | $CF_3$ | $CH_3$ | $O^nC_3H_7$ |
| 1-478 | F | Cl | H | $CF_3$ | $CH_3$ | $OCH_2CH_2Cl$ |
| 1-479 | F | Cl | H | $CF_3$ | $CH_3$ | $OCF_2CF_2H$ |
| 1-480 | F | Cl | H | $CF_3$ | $CH_3$ | $O^cC_5H_9$ |
| 1-481 | F | Cl | H | $CF_3$ | $CH_3$ | $O^cC_6H_{11}$ |
| 1-482 | F | Cl | H | $CF_3$ | $CH_3$ | $OCH_2CH=CH_2$ |
| 1-483 | F | Cl | H | $CF_3$ | $CH_3$ | $OCH_2CCl=CH_2$ |
| 1-484 | F | Cl | H | $CF_3$ | $CH_3$ | $OCH_2CCl=CHCl$ |
| 1-485 | F | Cl | H | $CF_3$ | $CH_3$ | $OCH(CH_3)CH=CH_2$ |
| 1-486 | F | Cl | H | $CF_3$ | $CH_3$ | $OCH_2C\equiv CH$ |
| 1-487 | F | Cl | H | $CF_3$ | $CH_3$ | $OCH(CH_3)C\equiv CH$ |
| 1-488 | F | Cl | H | $CF_3$ | $CH_3$ | $OCH_2C\equiv CBr$ |
| 1-489 | F | Cl | H | $CF_3$ | $CH_3$ | $OCH_2C\equiv CCl$ |
| 1-490 | F | Cl | H | $CF_3$ | $CH_3$ | $OCH_2C\equiv CCH_2Cl$ |
| 1-491 | F | Cl | H | $CF_3$ | $CH_3$ | $OCH_2CN$ |
| 1-492 | F | Cl | H | $CF_3$ | $CH_3$ | $OCH_2OCH_3$ |
| 1-493 | F | Cl | H | $CF_3$ | $CH_3$ | $OCH_2OC_2H_5$ |
| 1-494 | F | Cl | H | $CF_3$ | $CH_3$ | $OCH_2SCH_3$ |
| 1-495 | F | Cl | H | $CF_3$ | $CH_3$ | $OCH_2COOCH_3$ |
| 1-496 | F | Cl | H | $CF_3$ | $CH_3$ | $OCH_2COOC_2H_5$ |
| 1-497 | F | Cl | H | $CF_3$ | $CH_3$ | $OCH_2COO^nC_3H_7$ |
| 1-498 | F | Cl | H | $CF_3$ | $CH_3$ | $OCH_2COO^nC_4H_9$ |
| 1-499 | F | Cl | H | $CF_3$ | $CH_3$ | $OCH_2COO^nC_5H_{11}$ |
| 1-500 | F | Cl | H | $CF_3$ | $CH_3$ | $OCH_2COO^iC_3H_7$ |
| 1-501 | F | Cl | H | $CF_3$ | $CH_3$ | $OCH_2COO^cC_5H_9$ |
| 1-502 | F | Cl | H | $CF_3$ | $CH_3$ | $OCH_2COO^cC_6H_{11}$ |
| 1-503 | F | Cl | H | $CF_3$ | $CH_3$ | $OCH(CH_3)COOCH_3$ |
| 1-504 | F | Cl | H | $CF_3$ | $CH_3$ | $OCH(CH_3)COOC_2H_5$ |
| 1-505 | F | Cl | H | $CF_3$ | $CH_3$ | $OCH(CH_3)COO^nC_3H_7$ |
| 1-506 | F | Cl | H | $CF_3$ | $CH_3$ | $OCH(CH_3)COO^nC_4H_9$ |
| 1-507 | F | Cl | H | $CF_3$ | $CH_3$ | $OCH(CH_3)COO^nC_5H_{11}$ |
| 1-508 | F | Cl | H | $CF_3$ | $CH_3$ | $OCH(CH_3)COO^iC_3H_7$ |
| 1-509 | F | Cl | H | $CF_3$ | $CH_3$ | $OCH(CH_3)COO^cC_5H_9$ |
| 1-510 | F | Cl | H | $CF_3$ | $CH_3$ | $OCH(CH_3)COO^cC_6H_{11}$ |
| 1-511 | F | Cl | H | $CF_3$ | $CH_3$ | $OCH_2CON(CH_3)_2$ |
| 1-512 | F | Cl | H | $CF_3$ | $CH_3$ | $OCH_2CON(C_2H_5)_2$ |
| 1-513 | F | Cl | H | $CF_3$ | $CH_3$ | $OCH_2CON(CH_3)C_2H_5$ |

TABLE 1-continued

Compounds of the formula:

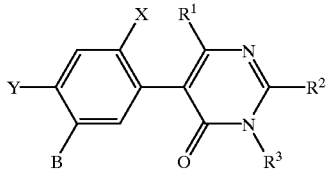

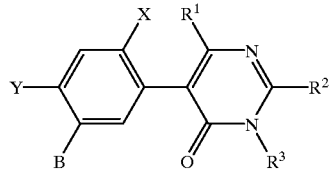

| Compound No. | X | Y | R¹ | R² | R³ | B |
|---|---|---|---|---|---|---|
| 1-514 | F | Cl | H | CF₃ | CH₃ | OCH(CH₃)CON(CH₃)₂ |
| 1-515 | F | Cl | H | CF₃ | CH₃ | OCH(CH₃)CON(C₂H₅)₂ |
| 1-516 | F | Cl | H | CF₃ | CH₃ | OCH(CH₃)CON(CH₃)C₂H₅ |
| 1-517 | F | Cl | H | CF₃ | CH₃ | OCH₂COON(CH₃)₂ |
| 1-518 | F | Cl | H | CF₃ | CH₃ | OCH₂COON(C₂H₅)₂ |
| 1-519 | F | Cl | H | CF₃ | CH₃ | OCH(CH₃)COON(CH₃)₂ |
| 1-520 | F | Cl | H | CF₃ | CH₃ | OCH(CH₃)COON(C₂H₅)₂ |
| 1-521 | H | F | H | CF₃ | CH₃ | SH |
| 1-522 | H | Cl | H | CF₃ | CH₃ | SH |
| 1-523 | H | Br | H | CF₃ | CH₃ | SH |
| 1-524 | F | F | H | CF₃ | CH₃ | SH |
| 1-525 | F | Cl | H | CF₃ | CH₃ | SH |
| 1-526 | F | Br | H | CF₃ | CH₃ | SH |
| 1-527 | H | Cl | H | CF₃ | CH₃ | SCH₃ |
| 1-528 | H | Cl | H | CF₃ | CH₃ | SC₂H₅ |
| 1-529 | H | Cl | H | CF₃ | CH₃ | S$^i$C₃H₇ |
| 1-530 | H | Cl | H | CF₃ | CH₃ | SCH₂CH₂Cl |
| 1-531 | H | Cl | H | CF₃ | CH₃ | S$^c$C₅H₉ |
| 1-532 | H | Cl | H | CF₃ | CH₃ | S$^c$C₆H₁₁ |
| 1-533 | H | Cl | H | CF₃ | CH₃ | SCH₂CH=CH₂ |
| 1-534 | H | Cl | H | CF₃ | CH₃ | SCH₂CCl=CH₂ |
| 1-535 | H | Cl | H | CF₃ | CH₃ | SCH₂CCl=CHCl |
| 1-536 | H | Cl | H | CF₃ | CH₃ | SCH(CH₃)CH=CH₂ |
| 1-537 | H | Cl | H | CF₃ | CH₃ | SCH₂C≡CH |
| 1-538 | H | Cl | H | CF₃ | CH₃ | SCH(CH₃)C≡CH |
| 1-539 | H | Cl | H | CF₃ | CH₃ | SCH₂COOCH₃ |
| 1-540 | H | Cl | H | CF₃ | CH₃ | SCH₂COOC₂H₅ |
| 1-541 | H | Cl | H | CF₃ | CH₃ | SCH₂COO$^n$C₃H₇ |
| 1-542 | H | Cl | H | CF₃ | CH₃ | SCH₂COO$^n$C₄H₉ |
| 1-543 | H | Cl | H | CF₃ | CH₃ | SCH₂COO$^n$C₅H₁₁ |
| 1-544 | H | Cl | H | CF₃ | CH₃ | SCH₂COO$^i$C₃H₇ |
| 1-545 | H | Cl | H | CF₃ | CH₃ | SCH₂COO$^c$C₅H₉ |
| 1-546 | H | Cl | H | CF₃ | CH₃ | SCH₂COO$^c$C₆H₁₁ |
| 1-547 | H | Cl | H | CF₃ | CH₃ | SCH(CH₃)COOCH₃ |
| 1-548 | H | Cl | H | CF₃ | CH₃ | SCH(CH₃)COOC₂H₅ |
| 1-549 | H | Cl | H | CF₃ | CH₃ | SCH(CH₃)COO$^n$C₃H₇ |
| 1-550 | H | Cl | H | CF₃ | CH₃ | SCH(CH₃)COO$^n$C₄H₉ |
| 1-551 | H | Cl | H | CF₃ | CH₃ | SCH(CH₃)COO$^n$C₅H₁₁ |
| 1-552 | H | Cl | H | CF₃ | CH₃ | SCH(CH₃)COO$^i$C₃H₇ |
| 1-553 | H | Cl | H | CF₃ | CH₃ | SCH(CH₃)COO$^c$C₅H₉ |
| 1-554 | H | Cl | H | CF₃ | CH₃ | SCH(CH₃)COO$^c$C₆H₁₁ |
| 1-555 | H | Cl | H | CF₃ | CH₃ | SCH₂CON(CH₃)₂ |
| 1-556 | H | Cl | H | CF₃ | CH₃ | SCH₂CON(C₂H₅)₂ |
| 1-557 | H | Cl | H | CF₃ | CH₃ | SCH₂CON(tetramethylene) |
| 1-558 | H | Cl | H | CF₃ | CH₃ | SCH₂CON(pentamethylene) |
| 1-559 | H | Cl | H | CF₃ | CH₃ | SCH₂CON(ethyleneoxyethylene) |
| 1-560 | H | Cl | H | CF₃ | CH₃ | SCH(CH₃)CON(CH₃)₂ |
| 1-561 | H | Cl | H | CF₃ | CH₃ | SCH(CH₃)CON(C₂H₅)₂ |
| 1-562 | H | Cl | H | CF₃ | CH₃ | SCH(CH₃)CON(tetramethylene) |
| 1-563 | H | Cl | H | CF₃ | CH₃ | SCH₂(CH₃)CON(pentamethylene) |
| 1-564 | F | Cl | H | CF₃ | CH₃ | SCH₃ |
| 1-565 | F | Cl | H | CF₃ | CH₃ | SC₂H₅ |
| 1-566 | F | Cl | H | CF₃ | CH₃ | S$^i$C₃H₇ |
| 1-567 | F | Cl | H | CF₃ | CH₃ | SCH₂CH₂Cl |
| 1-568 | F | Cl | H | CF₃ | CH₃ | S$^c$C₅H₉ |
| 1-569 | F | Cl | H | CF₃ | CH₃ | S$^c$C₆H₁₁ |
| 1-570 | F | Cl | H | CF₃ | CH₃ | SCH₂CH=CH₂ |
| 1-571 | F | Cl | H | CF₃ | CH₃ | SCH₂CCl=CH₂ |
| 1-572 | F | Cl | H | CF₃ | CH₃ | SCH₂CCl=CHCl |
| 1-573 | F | Cl | H | CF₃ | CH₃ | SCH(CH₃)CH=CH₂ |
| 1-574 | F | Cl | H | CF₃ | CH₃ | SCH₂C≡CH |
| 1-575 | F | Cl | H | CF₃ | CH₃ | SCH(CH₃)C≡CH |
| 1-576 | F | Cl | H | CF₃ | CH₃ | SCH₂COOCH₃ |
| 1-577 | F | Cl | H | CF₃ | CH₃ | SCH₂COOC₂H₅ |
| 1-578 | F | Cl | H | CF₃ | CH₃ | SCH₂COO$^n$C₃H₇ |
| 1-579 | F | Cl | H | CF₃ | CH₃ | SCH₂COO$^n$C₄H₉ |
| 1-580 | F | Cl | H | CF₃ | CH₃ | SCH₂COO$^n$C₅H₁₁ |
| 1-581 | F | Cl | H | CF₃ | CH₃ | SCH₂COO$^i$C₃H₇ |
| 1-582 | F | Cl | H | CF₃ | CH₃ | SCH₂COO$^c$C₅H₉ |
| 1-583 | F | Cl | H | CF₃ | CH₃ | SCH₂COO$^c$C₆H₁₁ |
| 1-584 | F | Cl | H | CF₃ | CH₃ | SCH(CH₃)COOCH₃ |
| 1-585 | F | Cl | H | CF₃ | CH₃ | SCH(CH₃)COOC₂H₅ |
| 1-586 | F | Cl | H | CF₃ | CH₃ | SCH(CH₃)COO$^n$C₃H₇ |
| 1-587 | F | Cl | H | CF₃ | CH₃ | SCH(CH₃)COO$^n$C₄H₉ |
| 1-588 | F | Cl | H | CF₃ | CH₃ | SCH(CH₃)COO$^n$C₅H₁₁ |
| 1-589 | F | Cl | H | CF₃ | CH₃ | SCH(CH₃)COO$^i$C₃H₇ |
| 1-590 | F | Cl | H | CF₃ | CH₃ | SCH(CH₃)COO$^c$C₅H₉ |
| 1-591 | F | Cl | H | CF₃ | CH₃ | SCH(CH₃)COO$^c$C₆H₁₁ |
| 1-592 | F | Cl | H | CF₃ | CH₃ | SCH₂CON(CH₃)₂ |
| 1-593 | F | Cl | H | CF₃ | CH₃ | SCH₂CON(C₂H₅)₂ |
| 1-594 | F | Cl | H | CF₃ | CH₃ | SCH₂CON(tetramethylene) |
| 1-595 | F | Cl | H | CF₃ | CH₃ | SCH₂CON(pentamethylene) |
| 1-596 | F | Cl | H | CF₃ | CH₃ | SCH₂CON(ethyleneoxyethylene) |
| 1-597 | F | Cl | H | CF₃ | CH₃ | SCH(CH₃)CON(CH₃)₂ |
| 1-598 | F | Cl | H | CF₃ | CH₃ | SCH(CH₃)CON(C₂H₅)₂ |
| 1-599 | F | Cl | H | CF₃ | CH₃ | SCH(CH₃)CON(tetramethylene) |
| 1-600 | F | Cl | H | CF₃ | CH₃ | SCH₂(CH₃)CON(pentamethylene) |
| 1-601 | H | F | H | CF₃ | CH₃ | SO₂Cl |
| 1-602 | H | Cl | H | CF₃ | CH₃ | SO₂Cl |
| 1-603 | H | Br | H | CF₃ | CH₃ | SO₂Cl |
| 1-604 | F | F | H | CF₃ | CH₃ | SO₂Cl |
| 1-605 | F | Cl | H | CF₃ | CH₃ | SO₂Cl |
| 1-606 | F | Br | H | CF₃ | CH₃ | SO₂Cl |
| 1-607 | H | Cl | H | CF₃ | CH₃ | SO₂OCH₃ |
| 1-608 | H | Cl | H | CF₃ | CH₃ | SO₂OC₂H₅ |
| 1-609 | H | Cl | H | CF₃ | CH₃ | SO₂O$^i$C₃H₇ |
| 1-610 | H | Cl | H | CF₃ | CH₃ | SO₂OCH₂CH=CH₂ |
| 1-611 | F | Cl | H | CF₃ | CH₃ | SO₂OCH₃ |
| 1-612 | F | Cl | H | CF₃ | CH₃ | SO₂OC₂H₅ |
| 1-613 | F | Cl | H | CF₃ | CH₃ | SO₂O$^i$C₃H₇ |
| 1-614 | F | Cl | H | CF₃ | CH₃ | SO₂OCH₂CH=CH₂ |
| 1-615 | H | Cl | H | CF₃ | CH₃ | SO₂N(CH₃)₂ |
| 1-616 | H | Cl | H | CF₃ | CH₃ | SO₂N(C₂H₅)₂ |
| 1-617 | F | Cl | H | CF₃ | CH₃ | SO₂N(CH₃)₂ |
| 1-618 | F | Cl | H | CF₃ | CH₃ | SO₂N(C₂H₅)₂ |
| 1-619 | H | Cl | H | CF₃ | CH₃ | COOH |
| 1-620 | H | Cl | H | CF₃ | CH₃ | COOCH₃ |
| 1-621 | H | Cl | H | CF₃ | CH₃ | COOC₂H₅ |
| 1-622 | H | Cl | H | CF₃ | CH₃ | COO$^n$C₃H₇ |
| 1-623 | H | Cl | H | CF₃ | CH₃ | COO$^n$C₄H₉ |
| 1-624 | H | Cl | H | CF₃ | CH₃ | COO$^n$C₅H₁₁ |
| 1-625 | H | Cl | H | CF₃ | CH₃ | COO$^i$C₃H₇ |
| 1-626 | H | Cl | H | CF₃ | CH₃ | COOCH₂CH₂Cl |
| 1-627 | H | Cl | H | CF₃ | CH₃ | COOCH₂CH₂Br |
| 1-628 | H | Cl | H | CF₃ | CH₃ | CON(CH₃)₂ |
| 1-629 | H | Cl | H | CF₃ | CH₃ | CONHCH₃ |
| 1-630 | H | Cl | H | CF₃ | CH₃ | CON(C₂H₅)₂ |
| 1-631 | H | Cl | H | CF₃ | CH₃ | CONHC₂H₅ |

TABLE 1-continued

Compounds of the formula:

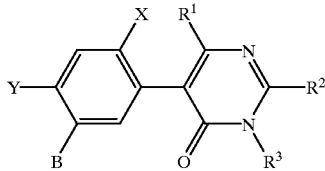

| Compound No. | X | Y | R¹ | R² | R³ | B |
|---|---|---|---|---|---|---|
| 1-632 | H | Cl | H | CF$_3$ | CH$_3$ | COCH$_3$ |
| 1-633 | H | Cl | H | CF$_3$ | CH$_3$ | COC$_2$H$_5$ |
| 1-634 | H | Cl | H | CF$_3$ | CH$_3$ | COCH$_2$Cl |
| 1-635 | H | Cl | H | CF$_3$ | CH$_3$ | CHO |
| 1-636 | H | Cl | H | CF$_3$ | CH$_3$ | CH=CHCOOCH$_3$ |
| 1-637 | H | Cl | H | CF$_3$ | CH$_3$ | CH=CHCOOC$_2$H$_5$ |
| 1-638 | H | Cl | H | CF$_3$ | CH$_3$ | CH$_2$CH$_2$COOCH$_3$ |
| 1-639 | H | Cl | H | CF$_3$ | CH$_3$ | CH$_2$CH$_2$COOC$_2$H$_5$ |
| 1-640 | F | Cl | H | CF$_3$ | CH$_3$ | COOH |
| 1-641 | F | Cl | H | CF$_3$ | CH$_3$ | COOCH$_3$ |
| 1-642 | F | Cl | H | CF$_3$ | CH$_3$ | COOC$_2$H$_5$ |
| 1-643 | F | Cl | H | CF$_3$ | CH$_3$ | COO$^n$C$_3$H$_7$ |
| 1-644 | F | Cl | H | CF$_3$ | CH$_3$ | COO$^n$C$_4$H$_9$ |
| 1-645 | F | Cl | H | CF$_3$ | CH$_3$ | COO$^n$C$_5$H$_{11}$ |
| 1-646 | F | Cl | H | CF$_3$ | CH$_3$ | COO$^i$C$_3$H$_7$ |
| 1-647 | F | Cl | H | CF$_3$ | CH$_3$ | COOCH$_2$CH$_2$Cl |
| 1-648 | F | Cl | H | CF$_3$ | CH$_3$ | COOCH$_2$CH$_2$Br |
| 1-649 | F | Cl | H | CF$_3$ | CH$_3$ | CON(CH$_3$)$_2$ |
| 1-650 | F | Cl | H | CF$_3$ | CH$_3$ | CONHCH$_3$ |
| 1-651 | F | Cl | H | CF$_3$ | CH$_3$ | CON(C$_2$H$_5$)$_2$ |
| 1-652 | F | Cl | H | CF$_3$ | CH$_3$ | CONHC$_2$H$_5$ |
| 1-653 | F | Cl | H | CF$_3$ | CH$_3$ | COCH$_3$ |
| 1-654 | F | Cl | H | CF$_3$ | CH$_3$ | COC$_2$H$_5$ |
| 1-655 | F | Cl | H | CF$_3$ | CH$_3$ | COCH$_2$Cl |
| 1-656 | F | Cl | H | CF$_3$ | CH$_3$ | CHO |
| 1-657 | F | Cl | H | CF$_3$ | CH$_3$ | CH=CHCOOCH$_3$ |
| 1-658 | F | Cl | H | CF$_3$ | CH$_3$ | CH=CHCOOC$_2$H$_5$ |
| 1-659 | F | Cl | H | CF$_3$ | CH$_3$ | CH$_2$CH$_2$COOCH$_3$ |
| 1-660 | F | Cl | H | CF$_3$ | CH$_3$ | CH$_2$CH$_2$COOC$_2$H$_5$ |
| 1-661 | Cl | Cl | H | CH$_3$ | C$_2$H$_5$ | H |
| 1-662 | Cl | Cl | H | CH$_3$ | CH$_3$ | H |
| 1-663 | F | F | H | CF$_3$ | CH$_3$ | NHCH(CH$_3$)COOC$_2$H$_5$ |
| 1-664 | Cl | Cl | H | CF$_3$ | CH$_3$ | H |
| 1-665 | Cl | Cl | H | CF$_3$ | CH$_3$ | NO$_2$ |
| 1-666 | Cl | Cl | H | CF$_3$ | CH$_3$ | NH$_2$ |
| 1-667 | Cl | Cl | H | CF$_3$ | CH$_3$ | NHCH(CH$_3$)COOC$_2$H$_5$ |
| 1-668 | Cl | Cl | H | CF$_3$ | CH$_3$ | NHSO$_2$CH$_3$ |
| 1-669 | F | Cl | H | CF$_3$ | CH$_3$ | NHCOCH$_3$ |
| 1-670 | Cl | Cl | H | CF$_3$ | CH$_3$ | OH |
| 1-671 | Cl | Cl | H | CF$_3$ | CH$_3$ | OCH(CH$_3$)$_2$ |
| 1-672 | Cl | Cl | H | CF$_3$ | CH$_3$ | OCH$_2$C≡CH |
| 1-673 | Cl | Cl | H | CF$_3$ | CH$_3$ | OCH(CH$_3$)C≡CH |
| 1-674 | Cl | Cl | H | CF$_3$ | CH$_3$ | OCH$_2$COOCH$_3$ |
| 1-675 | Cl | Cl | H | CF$_3$ | CH$_3$ | OCH$_2$COOC$_2$H$_5$ |
| 1-676 | Cl | Cl | H | CF$_3$ | CH$_3$ | OCH(CH$_3$)COOCH$_3$ |
| 1-677 | Cl | Cl | H | CF$_3$ | CH$_3$ | OCH(CH$_3$)COOC$_2$H$_5$ |
| 1-678 | Cl | Cl | H | CF$_3$ | CH$_3$ | SCH$_2$COOCH$_3$ |
| 1-679 | Cl | Cl | H | CF$_3$ | CH$_3$ | SCH$_2$COOC$_2$H$_5$ |
| 1-680 | Cl | Cl | H | CF$_3$ | CH$_3$ | SCH(CH$_3$)COOCH$_3$ |
| 1-681 | Cl | Cl | H | CF$_3$ | CH$_3$ | SCH(CH$_3$)COOC$_2$H$_5$ |
| 1-682 | Cl | Cl | H | CF$_3$ | CH$_3$ | NHCH$_2$COOCH$_3$ |
| 1-683 | Cl | Cl | H | CF$_3$ | CH$_3$ | NHCH$_2$COOCH$_3$ |
| 1-684 | Cl | Cl | H | CF$_3$ | CH$_3$ | NHCH(CH$_3$)COOC$_2$H$_5$ |
| 1-685 | F | Br | H | CF$_3$ | CH$_3$ | OCH$_2$C≡CH |
| 1-686 | F | Br | H | CF$_3$ | CH$_3$ | OCH$_2$COOC$_2$H$_5$ |
| 1-687 | F | Br | H | CF$_3$ | CH$_3$ | OCH(CH$_3$)COOC$_2$H$_5$ |
| 1-688 | F | Br | H | CF$_3$ | CH$_3$ | SCH$_2$COOC$_2$H$_5$ |
| 1-689 | F | Br | H | CF$_3$ | CH$_3$ | SCH(CH$_3$)COOC$_2$H$_5$ |
| 1-690 | F | Br | H | CF$_3$ | CH$_3$ | NHCH$_2$COOC$_2$H$_5$ |
| 1-691 | F | Br | H | CF$_3$ | CH$_3$ | NHCH(CH$_3$)COOC$_2$H$_5$ |
| 1-692 | F | F | H | CF$_3$ | CH$_3$ | OCH$_2$C≡CH |
| 1-693 | F | F | H | CF$_3$ | CH$_3$ | OCH$_2$COOC$_2$H$_5$ |
| 1-694 | F | F | H | CF$_3$ | CH$_3$ | OCH(CH$_3$)COOC$_2$H$_5$ |
| 1-695 | F | F | H | CF$_3$ | CH$_3$ | NHCH$_2$COOC$_2$H$_5$ |
| 1-696 | F | F | H | CF$_3$ | CH$_3$ | NHCH(CH$_3$)COOC$_2$H$_5$ |
| 1-697 | F | F | H | CF$_3$ | CH$_3$ | SCH$_2$COOC$_2$H$_5$ |
| 1-698 | F | F | H | CF$_3$ | CH$_3$ | SCH(CH$_3$)COOC$_2$H$_5$ |
| 1-699 | Cl | F | H | CF$_3$ | CH$_3$ | OCH$_2$C≡CH |
| 1-700 | Cl | F | H | CF$_3$ | CH$_3$ | OCH$_2$COOC$_2$H$_5$ |
| 1-701 | Cl | F | H | CF$_3$ | CH$_3$ | OCH(CH$_3$)COOC$_2$H$_5$ |
| 1-702 | Cl | F | H | CF$_3$ | CH$_3$ | SCH$_2$COOC$_2$H$_5$ |
| 1-703 | Cl | F | H | CF$_3$ | CH$_3$ | SCH(CH$_3$)COOC$_2$H$_5$ |
| 1-704 | Cl | F | H | CF$_3$ | CH$_3$ | NHCH$_2$COOC$_2$H$_5$ |
| 1-705 | Cl | F | H | CF$_3$ | CH$_3$ | NHCH(CH$_3$)COOC$_2$H$_5$ |
| 1-706 | F | Cl | H | CF$_2$H | CH$_3$ | OCH(CH$_3$)$_2$ |
| 1-707 | F | Cl | H | CF$_2$H | CH$_3$ | OCH$_2$C≡CH |
| 1-708 | F | Cl | H | CF$_2$CF$_3$ | CH$_3$ | OCH(CH$_3$)$_2$ |
| 1-709 | F | Cl | H | CF$_2$CF$_3$ | CH$_3$ | OCH$_2$C≡CH |
| 1-710 | F | Cl | H | CF$_2$Cl | CH$_3$ | OCH(CH$_3$)$_2$ |
| 1-711 | F | Cl | H | CF$_2$Cl | CH$_3$ | OCH$_2$C≡CH |
| 1-712 | Cl | Cl | H | CF$_3$ | CH$_3$ | NHCH$_2$COOC$_2$H$_5$ |
| 1-713 | F | Cl | H | CF$_3$ | CH$_3$ | CH$_2$CHClCOOC$_2$H$_5$ |
| 1-714 | F | Cl | H | CF$_3$ | CH$_3$ | I |
| 1-715 | F | Cl | H | CF$_3$ | CH$_3$ | OCH$_2$C(CH$_3$)=CH$_2$ |

TABLE 2

Compounds of the formula:

| Compound No. | X | Z¹ | n | R¹ | R² | R³ | R⁴ | R⁵ |
|---|---|---|---|---|---|---|---|---|
| 2-1 | H | O | 1 | H | CH$_3$ | CH$_3$ | H | H |
| 2-2 | H | O | 1 | H | CH$_3$ | CH$_3$ | H | CH$_3$ |
| 2-3 | H | O | 1 | H | CH$_3$ | CH$_3$ | H | C$_2$H$_5$ |
| 2-4 | H | O | 1 | H | CH$_3$ | CH$_3$ | H | $^n$C$_3$H$_7$ |
| 2-5 | H | O | 1 | H | CH$_3$ | CH$_3$ | H | $^i$C$_3$H$_7$ |
| 2-6 | H | O | 1 | H | CH$_3$ | CH$_3$ | H | $^i$C$_4$H$_9$ |
| 2-7 | H | O | 1 | H | CH$_3$ | CH$_3$ | H | $^i$C$_4$H$_9$ |
| 2-8 | H | O | 1 | H | CH$_3$ | CH$_3$ | H | CH$_2$CH$_2$Cl |
| 2-9 | H | O | 1 | H | CH$_3$ | CH$_3$ | H | CH$_2$CH$_2$Br |
| 2-10 | H | O | 1 | H | CH$_3$ | CH$_3$ | H | CH$_2$CH=CH$_2$ |
| 2-11 | H | O | 1 | H | CH$_3$ | CH$_3$ | H | CH(CH$_3$)CH=CH$_2$ |
| 2-12 | H | O | 1 | H | CH$_3$ | CH$_3$ | H | CH$_2$CCl=CH$_2$ |
| 2-13 | H | O | 1 | H | CH$_3$ | CH$_3$ | H | CH$_2$C≡CH |
| 2-14 | H | O | 1 | H | CH$_3$ | CH$_3$ | H | CH(CH$_3$)C≡CH |
| 2-15 | H | O | 1 | H | CH$_3$ | CH$_3$ | H | CH$_2$CN |
| 2-16 | H | O | 1 | H | CH$_3$ | CH$_3$ | H | CH$_2$OCH$_3$ |
| 2-17 | H | O | 1 | H | CH$_3$ | CH$_3$ | H | CH$_2$OC$_2$H$_5$ |
| 2-18 | H | O | 1 | H | CH$_3$ | CH$_3$ | H | CH$_2$COOH |
| 2-19 | H | O | 1 | H | CH$_3$ | CH$_3$ | H | CH$_2$COOCH$_3$ |

TABLE 2-continued

Compounds of the formula:

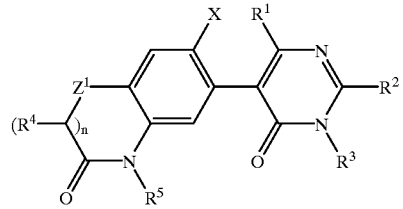 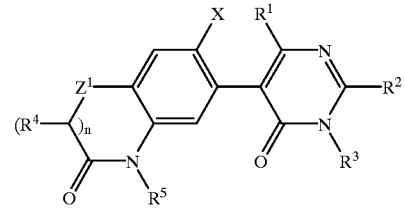

| Compound No. | X | $Z^1$ | n | $R^1$ | $R^2$ | $R^3$ | $R^4$ | $R^5$ |
|---|---|---|---|---|---|---|---|---|
| 2-20 | H | O | 1 | H | $CH_3$ | $CH_3$ | H | $CH_2COOC_2H_5$ |
| 2-21 | H | O | 1 | H | $CH_3$ | $CH_3$ | H | $CH_2COO^nC_3H_7$ |
| 2-22 | H | O | 1 | H | $CH_3$ | $CH_3$ | H | $CH_2COO^nC_4H_9$ |
| 2-23 | H | O | 1 | H | $CH_3$ | $CH_3$ | H | $CH_2COO^nC_5H_{11}$ |
| 2-24 | H | O | 1 | H | $CH_3$ | $CH_3$ | H | $CH_2COO^iC_3H_7$ |
| 2-25 | H | O | 1 | H | $CH_3$ | $CH_3$ | H | $CH_2COO^cC_5H_9$ |
| 2-26 | H | O | 1 | H | $CH_3$ | $CH_3$ | H | $CH_2COO^cC_6H_{11}$ |
| 2-27 | H | O | 1 | H | $CH_3$ | $CH_3$ | H | $CH(CH_3)COOH$ |
| 2-28 | H | O | 1 | H | $CH_3$ | $CH_3$ | H | $CH(CH_3)COOCH_3$ |
| 2-29 | H | O | 1 | H | $CH_3$ | $CH_3$ | H | $CH(CH_3)COOC_2H_5$ |
| 2-30 | H | O | 1 | H | $CH_3$ | $CH_3$ | H | $CH(CH_3)COO^nC_3H_7$ |
| 2-31 | H | O | 1 | H | $CH_3$ | $CH_3$ | H | $CH(CH_3)COO^nC_4H_9$ |
| 2-32 | H | O | 1 | H | $CH_3$ | $CH_3$ | H | $CH(CH_3)COO^nC_5H_{11}$ |
| 2-33 | H | O | 1 | H | $CH_3$ | $CH_3$ | H | $CH(CH_3)COO^iC_3H_7$ |
| 2-34 | H | O | 1 | H | $CH_3$ | $CH_3$ | H | $CH(CH_3)COO^cC_5H_9$ |
| 2-35 | H | O | 1 | H | $CH_3$ | $CH_3$ | H | $CH(CH_3)COO^cC_6H_{11}$ |
| 2-36 | H | O | 1 | H | $CH_3$ | $CH_3$ | $CH_3$ | H |
| 2-37 | H | O | 1 | H | $CH_3$ | $CH_3$ | $CH_3$ | $CH_3$ |
| 2-38 | H | O | 1 | H | $CH_3$ | $CH_3$ | $CH_3$ | $C_2H_5$ |
| 2-39 | H | O | 1 | H | $CH_3$ | $CH_3$ | $CH_3$ | $^nC_3H_7$ |
| 2-40 | H | O | 1 | H | $CH_3$ | $CH_3$ | $CH_3$ | $^iC_3H_7$ |
| 2-41 | H | O | 1 | H | $CH_3$ | $CH_3$ | $CH_3$ | $^iC_4H_9$ |
| 2-42 | H | O | 1 | H | $CH_3$ | $CH_3$ | $CH_3$ | $^nC_4H_9$ |
| 2-43 | H | O | 1 | H | $CH_3$ | $CH_3$ | $CH_3$ | $CH_2CH=CH_2$ |
| 2-44 | H | O | 1 | H | $CH_3$ | $CH_3$ | $CH_3$ | $CH(CH_3)CH=CH_2$ |
| 2-45 | H | O | 1 | H | $CH_3$ | $CH_3$ | $CH_3$ | $CH_2C\equiv CH$ |
| 2-46 | H | O | 1 | H | $CH_3$ | $CH_3$ | $CH_3$ | $CH(CH_3)C\equiv CH$ |
| 2-47 | H | O | 1 | H | $CH_3$ | $CH_3$ | $CH_3$ | $CH_2OCH_3$ |
| 2-48 | H | O | 1 | H | $CH_3$ | $CH_3$ | $CH_3$ | $CH_2OC_2H_5$ |
| 2-49 | F | O | 1 | H | $CH_3$ | $CH_3$ | H | H |
| 2-50 | F | O | 1 | H | $CH_3$ | $CH_3$ | H | $CH_3$ |
| 2-51 | F | O | 1 | H | $CH_3$ | $CH_3$ | H | $C_2H_5$ |
| 2-52 | F | O | 1 | H | $CH_3$ | $CH_3$ | H | $^nC_3H_7$ |
| 2-53 | F | O | 1 | H | $CH_3$ | $CH_3$ | H | $^iC_3H_7$ |
| 2-54 | F | O | 1 | H | $CH_3$ | $CH_3$ | H | $^iC_4H_9$ |
| 2-55 | F | O | 1 | H | $CH_3$ | $CH_3$ | H | $^nC_4H_9$ |
| 2-56 | F | O | 1 | H | $CH_3$ | $CH_3$ | H | $CH_2CH_2Cl$ |
| 2-57 | F | O | 1 | H | $CH_3$ | $CH_3$ | H | $CH_2CH_2Br$ |
| 2-58 | F | O | 1 | H | $CH_3$ | $CH_3$ | H | $CH_2CH=CH_2$ |
| 2-59 | F | O | 1 | H | $CH_3$ | $CH_3$ | H | $CH(CH_3)CH=CH_2$ |
| 2-60 | F | O | 1 | H | $CH_3$ | $CH_3$ | H | $CH_2CCl=CH_2$ |
| 2-61 | F | O | 1 | H | $CH_3$ | $CH_3$ | H | $CH_2C\equiv CH$ |
| 2-62 | F | O | 1 | H | $CH_3$ | $CH_3$ | H | $CH(CH_3)C\equiv CH$ |
| 2-63 | F | O | 1 | H | $CH_3$ | $CH_3$ | H | $CH_2CN$ |
| 2-64 | F | O | 1 | H | $CH_3$ | $CH_3$ | H | $CH_2OCH_3$ |
| 2-65 | F | O | 1 | H | $CH_3$ | $CH_3$ | H | $CH_2OC_2H_5$ |
| 2-66 | F | O | 1 | H | $CH_3$ | $CH_3$ | H | $CH_2COOH$ |
| 2-67 | F | O | 1 | H | $CH_3$ | $CH_3$ | H | $CH_2COOCH_3$ |
| 2-68 | F | O | 1 | H | $CH_3$ | $CH_3$ | H | $CH_2COOC_2H_5$ |
| 2-69 | F | O | 1 | H | $CH_3$ | $CH_3$ | H | $CH_2COO^nC_3H_7$ |
| 2-70 | F | O | 1 | H | $CH_3$ | $CH_3$ | H | $CH_2COO^nC_4H_9$ |
| 2-71 | F | O | 1 | H | $CH_3$ | $CH_3$ | H | $CH_2COO^nC_5H_{11}$ |
| 2-72 | F | O | 1 | H | $CH_3$ | $CH_3$ | H | $CH_2COO^iC_3H_7$ |
| 2-73 | F | O | 1 | H | $CH_3$ | $CH_3$ | H | $CH_2COO^cC_5H_9$ |
| 2-74 | F | O | 1 | H | $CH_3$ | $CH_3$ | H | $CH_2COO^cC_6H_{11}$ |
| 2-75 | F | O | 1 | H | $CH_3$ | $CH_3$ | H | $CH(CH_3)COOH$ |
| 2-76 | F | O | 1 | H | $CH_3$ | $CH_3$ | H | $CH(CH_3)COOCH_3$ |
| 2-77 | F | O | 1 | H | $CH_3$ | $CH_3$ | H | $CH(CH_3)COOC_2H_5$ |
| 2-78 | F | O | 1 | H | $CH_3$ | $CH_3$ | H | $CH(CH_3)COO^nC_3H_7$ |
| 2-79 | F | O | 1 | H | $CH_3$ | $CH_3$ | H | $CH(CH_3)COO^nC_4H_9$ |
| 2-80 | F | O | 1 | H | $CH_3$ | $CH_3$ | H | $CH(CH_3)COO^nC_5H_{11}$ |
| 2-81 | F | O | 1 | H | $CH_3$ | $CH_3$ | H | $CH(CH_3)COO^iC_3H_7$ |
| 2-82 | F | O | 1 | H | $CH_3$ | $CH_3$ | H | $CH(CH_3)COO^cC_5H_9$ |
| 2-83 | F | O | 1 | H | $CH_3$ | $CH_3$ | H | $CH(CH_3)COO^cC_6H_{11}$ |
| 2-84 | F | O | 1 | H | $CH_3$ | $CH_3$ | $CH_3$ | H |
| 2-85 | F | O | 1 | H | $CH_3$ | $CH_3$ | $CH_3$ | $CH_3$ |
| 2-86 | F | O | 1 | H | $CH_3$ | $CH_3$ | $CH_3$ | $C_2H_5$ |
| 2-87 | F | O | 1 | H | $CH_3$ | $CH_3$ | $CH_3$ | $^nC_3H_7$ |
| 2-88 | F | O | 1 | H | $CH_3$ | $CH_3$ | $CH_3$ | $^iC_3H_7$ |
| 2-89 | F | O | 1 | H | $CH_3$ | $CH_3$ | $CH_3$ | $^iC_4H_9$ |
| 2-90 | F | O | 1 | H | $CH_3$ | $CH_3$ | $CH_3$ | $^nC_4H_9$ |
| 2-91 | F | O | 1 | H | $CH_3$ | $CH_3$ | $CH_3$ | $CH_2CH=CH_2$ |
| 2-92 | F | O | 1 | H | $CH_3$ | $CH_3$ | $CH_3$ | $CH(CH_3)CH=CH_2$ |
| 2-93 | F | O | 1 | H | $CH_3$ | $CH_3$ | $CH_3$ | $CH_2C\equiv CH$ |
| 2-94 | F | O | 1 | H | $CH_3$ | $CH_3$ | $CH_3$ | $CH(CH_3)C\equiv CH$ |
| 2-95 | F | O | 1 | H | $CH_3$ | $CH_3$ | $CH_3$ | $CH_2OCH_3$ |
| 2-96 | F | O | 1 | H | $CH_3$ | $CH_3$ | $CH_3$ | $CH_2OC_2H_5$ |
| 2-97 | H | S | 0 | H | $CH_3$ | $CH_3$ | — | H |
| 2-98 | H | S | 0 | H | $CH_3$ | $CH_3$ | — | $CH_3$ |
| 2-99 | H | S | 0 | H | $CH_3$ | $CH_3$ | — | $C_2H_5$ |
| 2-100 | H | S | 0 | H | $CH_3$ | $CH_3$ | — | $^nC_3H_7$ |
| 2-101 | H | S | 0 | H | $CH_3$ | $CH_3$ | — | $^nC_4H_9$ |
| 2-102 | H | S | 0 | H | $CH_3$ | $CH_3$ | — | $^iC_3H_7$ |
| 2-103 | H | S | 0 | H | $CH_3$ | $CH_3$ | — | $^iC_4H_9$ |
| 2-104 | H | S | 0 | H | $CH_3$ | $CH_3$ | — | $CH_2CH_2Cl$ |
| 2-105 | H | S | 0 | H | $CH_3$ | $CH_3$ | — | $CH_2CH_2Br$ |
| 2-106 | H | S | 0 | H | $CH_3$ | $CH_3$ | — | $CH_2CH=CH_2$ |
| 2-107 | H | S | 0 | H | $CH_3$ | $CH_3$ | — | $CH(CH_3)CH=CH_2$ |
| 2-108 | H | S | 0 | H | $CH_3$ | $CH_3$ | — | $CH_2CCl=CH_2$ |
| 2-109 | H | S | 0 | H | $CH_3$ | $CH_3$ | — | $CH_2C\equiv CH$ |
| 2-110 | H | S | 0 | H | $CH_3$ | $CH_3$ | — | $CH(CH_3)C\equiv CH$ |
| 2-111 | H | S | 0 | H | $CH_3$ | $CH_3$ | — | $CH_2CN$ |
| 2-112 | H | S | 0 | H | $CH_3$ | $CH_3$ | — | $CH_2OCH_3$ |
| 2-113 | H | S | 0 | H | $CH_3$ | $CH_3$ | — | $CH_2OC_2H_5$ |
| 2-114 | H | S | 0 | H | $CH_3$ | $CH_3$ | — | $CH_2COOH$ |
| 2-115 | H | S | 0 | H | $CH_3$ | $CH_3$ | — | $CH_2COOCH_3$ |
| 2-116 | H | S | 0 | H | $CH_3$ | $CH_3$ | — | $CH_2COOC_2H_5$ |
| 2-117 | H | S | 0 | H | $CH_3$ | $CH_3$ | — | $CH_2COO^nC_3H_7$ |
| 2-118 | H | S | 0 | H | $CH_3$ | $CH_3$ | — | $CH_2COO^nC_4H_9$ |
| 2-119 | H | S | 0 | H | $CH_3$ | $CH_3$ | — | $CH_2COO^nC_5H_{11}$ |
| 2-120 | H | S | 0 | H | $CH_3$ | $CH_3$ | — | $CH_2COO^iC_3H_7$ |
| 2-121 | H | S | 0 | H | $CH_3$ | $CH_3$ | — | $CH_2COO^cC_5H_9$ |
| 2-122 | H | S | 0 | H | $CH_3$ | $CH_3$ | — | $CH_2COO^cC_6H_{11}$ |
| 2-123 | H | S | 0 | H | $CH_3$ | $CH_3$ | — | $CH(CH_3)COOH$ |
| 2-124 | H | S | 0 | H | $CH_3$ | $CH_3$ | — | $CH(CH_3)COOCH_3$ |
| 2-125 | H | S | 0 | H | $CH_3$ | $CH_3$ | — | $CH(CH_3)COOC_2H_5$ |
| 2-126 | H | S | 0 | H | $CH_3$ | $CH_3$ | — | $CH(CH_3)COO^nC_3H_7$ |
| 2-127 | H | S | 0 | H | $CH_3$ | $CH_3$ | — | $CH(CH_3)COO^nC_4H_9$ |
| 2-128 | H | S | 0 | H | $CH_3$ | $CH_3$ | — | $CH(CH_3)COO^nC_5H_{11}$ |
| 2-129 | H | S | 0 | H | $CH_3$ | $CH_3$ | — | $CH(CH_3)COO^iC_3H_7$ |
| 2-130 | H | S | 0 | H | $CH_3$ | $CH_3$ | — | $CH(CH_3)COO^cC_5H_9$ |
| 2-131 | H | S | 0 | H | $CH_3$ | $CH_3$ | — | $CH(CH_3)COO^cC_6H_{11}$ |
| 2-132 | F | S | 0 | H | $CH_3$ | $CH_3$ | — | H |
| 2-133 | F | S | 0 | H | $CH_3$ | $CH_3$ | — | $CH_3$ |
| 2-134 | F | S | 0 | H | $CH_3$ | $CH_3$ | — | $C_2H_5$ |
| 2-135 | F | S | 0 | H | $CH_3$ | $CH_3$ | — | $^nC_3H_7$ |
| 2-136 | F | S | 0 | H | $CH_3$ | $CH_3$ | — | $^nC_4H_9$ |
| 2-137 | F | S | 0 | H | $CH_3$ | $CH_3$ | — | $^iC_3H_7$ |
| 2-138 | F | S | 0 | H | $CH_3$ | $CH_3$ | — | $^iC_4H_9$ |
| 2-139 | F | S | 0 | H | $CH_3$ | $CH_3$ | — | $CH_2CH_2Cl$ |
| 2-140 | F | S | 0 | H | $CH_3$ | $CH_3$ | — | $CH_2CH_2Br$ |
| 2-141 | F | S | 0 | H | $CH_3$ | $CH_3$ | — | $CH_2CH=CH_2$ |

TABLE 2-continued

Compounds of the formula:

| Compound No. | X | $Z^1$ | n | $R^1$ | $R^2$ | $R^3$ | $R^4$ | $R^5$ |
|---|---|---|---|---|---|---|---|---|
| 2-142 | F | S | 0 | H | $CH_3$ | $CH_3$ | — | $CH(CH_3)CH=CH_2$ |
| 2-143 | F | S | 0 | H | $CH_3$ | $CH_3$ | — | $CH_2CCl=CH_2$ |
| 2-144 | F | S | 0 | H | $CH_3$ | $CH_3$ | — | $CH_2C\equiv CH$ |
| 2-145 | F | S | 0 | H | $CH_3$ | $CH_3$ | — | $CH(CH_3)C\equiv CH$ |
| 2-146 | F | S | 0 | H | $CH_3$ | $CH_3$ | — | $CH_2CN$ |
| 2-147 | F | S | 0 | H | $CH_3$ | $CH_3$ | — | $CH_2OCH_3$ |
| 2-148 | F | S | 0 | H | $CH_3$ | $CH_3$ | — | $CH_2OC_2H_5$ |
| 2-149 | F | S | 0 | H | $CH_3$ | $CH_3$ | — | $CH_2COOH$ |
| 2-150 | F | S | 0 | H | $CH_3$ | $CH_3$ | — | $CH_2COOCH_3$ |
| 2-151 | F | S | 0 | H | $CH_3$ | $CH_3$ | — | $CH_2COOC_2H_5$ |
| 2-152 | F | S | 0 | H | $CH_3$ | $CH_3$ | — | $CH_2COO^nC_3H_7$ |
| 2-153 | F | S | 0 | H | $CH_3$ | $CH_3$ | — | $CH_2COO^nC_4H_9$ |
| 2-154 | F | S | 0 | H | $CH_3$ | $CH_3$ | — | $CH_2COO^nC_5H_{11}$ |
| 2-155 | F | S | 0 | H | $CH_3$ | $CH_3$ | — | $CH_2COO^iC_3H_7$ |
| 2-156 | F | S | 0 | H | $CH_3$ | $CH_3$ | — | $CH_2COO^cC_5H_9$ |
| 2-157 | F | S | 0 | H | $CH_3$ | $CH_3$ | — | $CH_2COO^cC_6H_{11}$ |
| 2-158 | F | S | 0 | H | $CH_3$ | $CH_3$ | — | $CH(CH_3)COOH$ |
| 2-159 | F | S | 0 | H | $CH_3$ | $CH_3$ | — | $CH(CH_3)COOCH_3$ |
| 2-160 | F | S | 0 | H | $CH_3$ | $CH_3$ | — | $CH(CH_3)COOC_2H_5$ |
| 2-161 | F | S | 0 | H | $CH_3$ | $CH_3$ | — | $CH(CH_3)COO^nC_3H_7$ |
| 2-162 | F | S | 0 | H | $CH_3$ | $CH_3$ | — | $CH(CH_3)COO^nC_4H_9$ |
| 2-163 | F | S | 0 | H | $CH_3$ | $CH_3$ | — | $CH(CH_3)COO^nC_5H_{11}$ |
| 2-164 | F | S | 0 | H | $CH_3$ | $CH_3$ | — | $CH(CH_3)COO^iC_3H_7$ |
| 2-165 | F | S | 0 | H | $CH_3$ | $CH_3$ | — | $CH(CH_3)COO^cC_5H_9$ |
| 2-166 | F | S | 0 | H | $CH_3$ | $CH_3$ | — | $CH(CH_3)COO^cC_6H_{11}$ |
| 2-167 | H | O | 0 | H | $CH_3$ | $CH_3$ | — | H |
| 2-168 | H | O | 0 | H | $CH_3$ | $CH_3$ | — | $CH_3$ |
| 2-169 | H | O | 0 | H | $CH_3$ | $CH_3$ | — | $C_2H_5$ |
| 2-170 | H | O | 0 | H | $CH_3$ | $CH_3$ | — | $^nC_3H_7$ |
| 2-171 | H | O | 0 | H | $CH_3$ | $CH_3$ | — | $^nC_4H_9$ |
| 2-172 | H | O | 0 | H | $CH_3$ | $CH_3$ | — | $^iC_3H_7$ |
| 2-173 | H | O | 0 | H | $CH_3$ | $CH_3$ | — | $^iC_4H_9$ |
| 2-174 | H | O | 0 | H | $CH_3$ | $CH_3$ | — | $CH_2CH=CH_2$ |
| 2-175 | H | O | 0 | H | $CH_3$ | $CH_3$ | — | $CH(CH_3)CH=CH_2$ |
| 2-176 | H | O | 0 | H | $CH_3$ | $CH_3$ | — | $CH_2C\equiv CH$ |
| 2-177 | H | O | 0 | H | $CH_3$ | $CH_3$ | — | $CH(CH_3)C\equiv CH$ |
| 2-178 | H | O | 0 | H | $CH_3$ | $CH_3$ | — | $CH_2OCH_3$ |
| 2-179 | H | O | 0 | H | $CH_3$ | $CH_3$ | — | $CH_2OC_2H_5$ |
| 2-180 | F | O | 0 | H | $CH_3$ | $CH_3$ | — | H |
| 2-181 | F | O | 0 | H | $CH_3$ | $CH_3$ | — | $CH_3$ |
| 2-182 | F | O | 0 | H | $CH_3$ | $CH_3$ | — | $C_2H_5$ |
| 2-183 | F | O | 0 | H | $CH_3$ | $CH_3$ | — | $^nC_3H_7$ |
| 2-184 | F | O | 0 | H | $CH_3$ | $CH_3$ | — | $^nC_4H_9$ |
| 2-185 | F | O | 0 | H | $CH_3$ | $CH_3$ | — | $CH_2CH=CH_2$ |
| 2-186 | F | O | 0 | H | $CH_3$ | $CH_3$ | — | $CH(CH_3)CH=CH_2$ |
| 2-187 | F | O | 0 | H | $CH_3$ | $CH_3$ | — | $CH_2C\equiv CH$ |
| 2-188 | F | O | 0 | H | $CH_3$ | $CH_3$ | — | $CH(CH_3)C\equiv CH$ |
| 2-189 | F | O | 0 | H | $CH_3$ | $CH_3$ | — | $CH_2OCH_3$ |
| 2-190 | F | O | 0 | H | $CH_3$ | $CH_3$ | — | $CH_2OC_2H_5$ |
| 2-191 | H | O | 1 | H | $CF_3$ | $CH_3$ | H | H |
| 2-192 | H | O | 1 | H | $CF_3$ | $CH_3$ | H | $CH_3$ |
| 2-193 | H | O | 1 | H | $CF_3$ | $CH_3$ | H | $C_2H_5$ |
| 2-194 | H | O | 1 | H | $CF_3$ | $CH_3$ | H | $^nC_3H_7$ |
| 2-195 | H | O | 1 | H | $CF_3$ | $CH_3$ | H | $^iC_3H_7$ |
| 2-196 | H | O | 1 | H | $CF_3$ | $CH_3$ | H | $^iC_4H_9$ |
| 2-197 | H | O | 1 | H | $CF_3$ | $CH_3$ | H | $^nC_4H_9$ |
| 2-198 | H | O | 1 | H | $CF_3$ | $CH_3$ | H | $CH_2CH_2Cl$ |
| 2-199 | H | O | 1 | H | $CF_3$ | $CH_3$ | H | $CH_2CH_2Br$ |
| 2-200 | H | O | 1 | H | $CF_3$ | $CH_3$ | H | $CH_2CH=CH_2$ |
| 2-201 | H | O | 1 | H | $CF_3$ | $CH_3$ | H | $CH(CH_3)CH=CH_2$ |
| 2-202 | H | O | 1 | H | $CF_3$ | $CH_3$ | H | $CH_2CCl=CH_2$ |
| 2-203 | H | O | 1 | H | $CF_3$ | $CH_3$ | H | $CH_2C\equiv CH$ |
| 2-204 | H | O | 1 | H | $CF_3$ | $CH_3$ | H | $CH(CH_3)C\equiv CH$ |
| 2-205 | H | O | 1 | H | $CF_3$ | $CH_3$ | H | $CH_2CN$ |
| 2-206 | H | O | 1 | H | $CF_3$ | $CH_3$ | H | $CH_2OCH_3$ |
| 2-207 | H | O | 1 | H | $CF_3$ | $CH_3$ | H | $CH_2OC_2H_5$ |
| 2-208 | H | O | 1 | H | $CF_3$ | $CH_3$ | H | $CH_2COOH$ |
| 2-209 | H | O | 1 | H | $CF_3$ | $CH_3$ | H | $CH_2COOCH_3$ |
| 2-210 | H | O | 1 | H | $CF_3$ | $CH_3$ | H | $CH_2COOC_2H_5$ |
| 2-211 | H | O | 1 | H | $CF_3$ | $CH_3$ | H | $CH_2COO^nC_3H_7$ |
| 2-212 | H | O | 1 | H | $CF_3$ | $CH_3$ | H | $CH_2COO^nC_4H_9$ |
| 2-213 | H | O | 1 | H | $CF_3$ | $CH_3$ | H | $CH_2COO^nC_5H_{11}$ |
| 2-214 | H | O | 1 | H | $CF_3$ | $CH_3$ | H | $CH_2COO^iC_3H_7$ |
| 2-215 | H | O | 1 | H | $CF_3$ | $CH_3$ | H | $CH_2COO^cC_5H_9$ |
| 2-216 | H | O | 1 | H | $CF_3$ | $CH_3$ | H | $CH_2COO^cC_6H_{11}$ |
| 2-217 | H | O | 1 | H | $CF_3$ | $CH_3$ | H | $CH(CH_3)COOH$ |
| 2-218 | H | O | 1 | H | $CF_3$ | $CH_3$ | H | $CH(CH_3)COOCH_3$ |
| 2-219 | H | O | 1 | H | $CF_3$ | $CH_3$ | H | $CH(CH_3)COOC_2H_5$ |
| 2-220 | H | O | 1 | H | $CF_3$ | $CH_3$ | H | $CH(CH_3)COO^nC_3H_7$ |
| 2-221 | H | O | 1 | H | $CF_3$ | $CH_3$ | H | $CH(CH_3)COO^nC_4H_9$ |
| 2-222 | H | O | 1 | H | $CF_3$ | $CH_3$ | H | $CH(CH_3)COO^nC_5H_{11}$ |
| 2-223 | H | O | 1 | H | $CF_3$ | $CH_3$ | H | $CH(CH_3)COO^iC_3H_7$ |
| 2-224 | H | O | 1 | H | $CF_3$ | $CH_3$ | H | $CH(CH_3)COO^cC_5H_9$ |
| 2-225 | H | O | 1 | H | $CF_3$ | $CH_3$ | H | $CH(CH_3)COO^cC_6H_{11}$ |
| 2-226 | H | O | 1 | H | $CF_3$ | $CH_3$ | $CH_3$ | H |
| 2-227 | H | O | 1 | H | $CF_3$ | $CH_3$ | $CH_3$ | $CH_3$ |
| 2-228 | H | O | 1 | H | $CF_3$ | $CH_3$ | $CH_3$ | $C_2H_5$ |
| 2-229 | H | O | 1 | H | $CF_3$ | $CH_3$ | $CH_3$ | $^nC_3H_7$ |
| 2-230 | H | O | 1 | H | $CF_3$ | $CH_3$ | $CH_3$ | $^iC_3H_7$ |
| 2-231 | H | O | 1 | H | $CF_3$ | $CH_3$ | $CH_3$ | $^iC_4H_9$ |
| 2-232 | H | O | 1 | H | $CF_3$ | $CH_3$ | $CH_3$ | $^nC_4H_9$ |
| 2-233 | H | O | 1 | H | $CF_3$ | $CH_3$ | $CH_3$ | $CH_2CH=CH_2$ |
| 2-234 | H | O | 1 | H | $CF_3$ | $CH_3$ | $CH_3$ | $CH(CH_3)CH=CH_2$ |
| 2-235 | H | O | 1 | H | $CF_3$ | $CH_3$ | $CH_3$ | $CH_2C\equiv CH$ |
| 2-236 | H | O | 1 | H | $CF_3$ | $CH_3$ | $CH_3$ | $CH(CH_3)C\equiv CH$ |
| 2-237 | H | O | 1 | H | $CF_3$ | $CH_3$ | $CH_3$ | $CH_2OCH_3$ |
| 2-238 | H | O | 1 | H | $CF_3$ | $CH_3$ | $CH_3$ | $CH_2OC_2H_5$ |
| 2-239 | F | O | 1 | H | $CF_3$ | $CH_3$ | H | H |
| 2-240 | F | O | 1 | H | $CF_3$ | $CH_3$ | H | $CH_3$ |
| 2-241 | F | O | 1 | H | $CF_3$ | $CH_3$ | H | $C_2H_5$ |
| 2-242 | F | O | 1 | H | $CF_3$ | $CH_3$ | H | $^nC_3H_7$ |
| 2-243 | F | O | 1 | H | $CF_3$ | $CH_3$ | H | $^iC_3H_7$ |
| 2-244 | F | O | 1 | H | $CF_3$ | $CH_3$ | H | $^iC_4H_9$ |
| 2-245 | F | O | 1 | H | $CF_3$ | $CH_3$ | H | $^nC_4H_9$ |
| 2-246 | F | O | 1 | H | $CF_3$ | $CH_3$ | H | $CH_2CH_2Cl$ |
| 2-247 | F | O | 1 | H | $CF_3$ | $CH_3$ | H | $CH_2CH_2Br$ |
| 2-248 | F | O | 1 | H | $CF_3$ | $CH_3$ | H | $CH_2CH=CH_2$ |
| 2-249 | F | O | 1 | H | $CF_3$ | $CH_3$ | H | $CH(CH_3)CH=CH_2$ |
| 2-250 | F | O | 1 | H | $CF_3$ | $CH_3$ | H | $CH_2CCl=CH_2$ |
| 2-251 | F | O | 1 | H | $CF_3$ | $CH_3$ | H | $CH_2C\equiv CH$ |
| 2-252 | F | O | 1 | H | $CF_3$ | $CH_3$ | H | $CH(CH_3)C\equiv CH$ |
| 2-253 | F | O | 1 | H | $CF_3$ | $CH_3$ | H | $CH_2CN$ |
| 2-254 | F | O | 1 | H | $CF_3$ | $CH_3$ | H | $CH_2OCH_3$ |
| 2-255 | F | O | 1 | H | $CF_3$ | $CH_3$ | H | $CH_2OC_2H_5$ |
| 2-256 | F | O | 1 | H | $CF_3$ | $CH_3$ | H | $CH_2COOH$ |
| 2-257 | F | O | 1 | H | $CF_3$ | $CH_3$ | H | $CH_2COOCH_3$ |
| 2-258 | F | O | 1 | H | $CF_3$ | $CH_3$ | H | $CH_2COOC_2H_5$ |
| 2-259 | F | O | 1 | H | $CF_3$ | $CH_3$ | H | $CH_2COO^nC_3H_7$ |
| 2-260 | F | O | 1 | H | $CF_3$ | $CH_3$ | H | $CH_2COO^nC_4H_9$ |
| 2-261 | F | O | 1 | H | $CF_3$ | $CH_3$ | H | $CH_2COO^nC_5H_{11}$ |
| 2-262 | F | O | 1 | H | $CF_3$ | $CH_3$ | H | $CH_2COO^iC_3H_7$ |
| 2-263 | F | O | 1 | H | $CF_3$ | $CH_3$ | H | $CH_2COO^cC_5H_9$ |

TABLE 2-continued

Compounds of the formula:

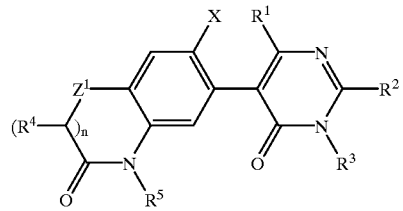
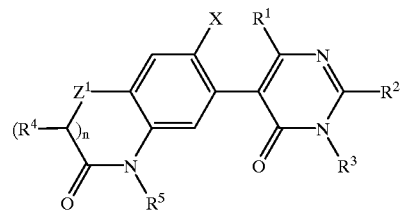

| Compound No. | X | $Z^1$ | n | $R^1$ | $R^2$ | $R^3$ | $R^4$ | $R^5$ |
|---|---|---|---|---|---|---|---|---|
| 2-264 | F | O | 1 | H | $CF_3$ | $CH_3$ | H | $CH_2COO^cC_6H_{11}$ |
| 2-265 | F | O | 1 | H | $CF_3$ | $CH_3$ | H | $CH(CH_3)COOH$ |
| 2-266 | F | O | 1 | H | $CF_3$ | $CH_3$ | H | $CH(CH_3)COOCH_3$ |
| 2-267 | F | O | 1 | H | $CF_3$ | $CH_3$ | H | $CH(CH_3)COOC_2H_5$ |
| 2-268 | F | O | 1 | H | $CF_3$ | $CH_3$ | H | $CH(CH_3)COO^nC_3H_7$ |
| 2-269 | F | O | 1 | H | $CF_3$ | $CH_3$ | H | $CH(CH_3)COO^nC_4H_9$ |
| 2-270 | F | O | 1 | H | $CF_3$ | $CH_3$ | H | $CH(CH_3)COO^nC_5H_{11}$ |
| 2-271 | F | O | 1 | H | $CF_3$ | $CH_3$ | H | $CH(CH_3)COO^iC_3H_7$ |
| 2-272 | F | O | 1 | H | $CF_3$ | $CH_3$ | H | $CH(CH_3)COO^cC_5H_9$ |
| 2-273 | F | O | 1 | H | $CF_3$ | $CH_3$ | H | $CH(CH_3)COO^cC_6H_{11}$ |
| 2-274 | F | O | 1 | H | $CF_3$ | $CH_3$ | $CH_3$ | H |
| 2-275 | F | O | 1 | H | $CF_3$ | $CH_3$ | $CH_3$ | $CH_3$ |
| 2-276 | F | O | 1 | H | $CF_3$ | $CH_3$ | $CH_3$ | $C_2H_5$ |
| 2-277 | F | O | 1 | H | $CF_3$ | $CH_3$ | $CH_3$ | $^nC_3H_7$ |
| 2-278 | F | O | 1 | H | $CF_3$ | $CH_3$ | $CH_3$ | $^iC_3H_7$ |
| 2-279 | F | O | 1 | H | $CF_3$ | $CH_3$ | $CH_3$ | $^iC_4H_9$ |
| 2-280 | F | O | 1 | H | $CF_3$ | $CH_3$ | $CH_3$ | $^nC_4H_9$ |
| 2-281 | F | O | 1 | H | $CF_3$ | $CH_3$ | $CH_3$ | $CH_2CH=CH_2$ |
| 2-282 | F | O | 1 | H | $CF_3$ | $CH_3$ | $CH_3$ | $CH(CH_3)CH=CH_2$ |
| 2-283 | F | O | 1 | H | $CF_3$ | $CH_3$ | $CH_3$ | $CH_2C\equiv CH$ |
| 2-284 | F | O | 1 | H | $CF_3$ | $CH_3$ | $CH_3$ | $CH(CH_3)C\equiv CH$ |
| 2-285 | F | O | 1 | H | $CF_3$ | $CH_3$ | $CH_3$ | $CH_2OCH_3$ |
| 2-286 | F | O | 1 | H | $CF_3$ | $CH_3$ | $CH_3$ | $CH_2OC_2H_5$ |
| 2-287 | H | S | 0 | H | $CF_3$ | $CH_3$ | — | H |
| 2-288 | H | S | 0 | H | $CF_3$ | $CH_3$ | — | $CH_3$ |
| 2-289 | H | S | 0 | H | $CF_3$ | $CH_3$ | — | $C_2H_5$ |
| 2-290 | H | S | 0 | H | $CF_3$ | $CH_3$ | — | $^nC_3H_7$ |
| 2-291 | H | S | 0 | H | $CF_3$ | $CH_3$ | — | $^nC_4H_9$ |
| 2-292 | H | S | 0 | H | $CF_3$ | $CH_3$ | — | $^iC_3H_7$ |
| 2-293 | H | S | 0 | H | $CF_3$ | $CH_3$ | — | $^iC_4H_9$ |
| 2-294 | H | S | 0 | H | $CF_3$ | $CH_3$ | — | $CH_2CH_2Cl$ |
| 2-295 | H | S | 0 | H | $CF_3$ | $CH_3$ | — | $CH_2CH_2Br$ |
| 2-296 | H | S | 0 | H | $CF_3$ | $CH_3$ | — | $CH_2CH=CH_2$ |
| 2-297 | H | S | 0 | H | $CF_3$ | $CH_3$ | — | $CH(CH_3)CH=CH_2$ |
| 2-298 | H | S | 0 | H | $CF_3$ | $CH_3$ | — | $CH_2CCl=CH_2$ |
| 2-299 | H | S | 0 | H | $CF_3$ | $CH_3$ | — | $CH_2C\equiv CH$ |
| 2-300 | H | S | 0 | H | $CF_3$ | $CH_3$ | — | $CH(CH_3)C\equiv CH$ |
| 2-301 | H | S | 0 | H | $CF_3$ | $CH_3$ | — | $CH_2CN$ |
| 2-302 | H | S | 0 | H | $CF_3$ | $CH_3$ | — | $CH_2OCH_3$ |
| 2-303 | H | S | 0 | H | $CF_3$ | $CH_3$ | — | $CH_2OC_2H_5$ |
| 2-304 | H | S | 0 | H | $CF_3$ | $CH_3$ | — | $CH_2COOH$ |
| 2-305 | H | S | 0 | H | $CF_3$ | $CH_3$ | — | $CH_2COOCH_3$ |
| 2-306 | H | S | 0 | H | $CF_3$ | $CH_3$ | — | $CH_2COOC_2H_5$ |
| 2-307 | H | S | 0 | H | $CF_3$ | $CH_3$ | — | $CH_2COO^nC_3H_7$ |
| 2-308 | H | S | 0 | H | $CF_3$ | $CH_3$ | — | $CH_2COO^nC_4H_9$ |
| 2-309 | H | S | 0 | H | $CF_3$ | $CH_3$ | — | $CH_2COO^nC_5H_{11}$ |
| 2-310 | H | S | 0 | H | $CF_3$ | $CH_3$ | — | $CH_2COO^iC_3H_7$ |
| 2-311 | H | S | 0 | H | $CF_3$ | $CH_3$ | — | $CH_2COO^cC_5H_9$ |
| 2-312 | H | S | 0 | H | $CF_3$ | $CH_3$ | — | $CH_2COO^cC_6H_{11}$ |
| 2-313 | H | S | 0 | H | $CF_3$ | $CH_3$ | — | $CH(CH_3)COOH$ |
| 2-314 | H | S | 0 | H | $CF_3$ | $CH_3$ | — | $CH(CH_3)COOCH_3$ |
| 2-315 | H | S | 0 | H | $CF_3$ | $CH_3$ | — | $CH(CH_3)COOC_2H_5$ |
| 2-316 | H | S | 0 | H | $CF_3$ | $CH_3$ | — | $CH(CH_3)COO^nC_3H_7$ |
| 2-317 | H | S | 0 | H | $CF_3$ | $CH_3$ | — | $CH(CH_3)COO^nC_4H_9$ |
| 2-318 | H | S | 0 | H | $CF_3$ | $CH_3$ | — | $CH(CH_3)COO^nC_5H_{11}$ |
| 2-319 | H | S | 0 | H | $CF_3$ | $CH_3$ | — | $CH(CH_3)COO^iC_3H_7$ |
| 2-320 | H | S | 0 | H | $CF_3$ | $CH_3$ | — | $CH(CH_3)COO^cC_5H_9$ |
| 2-321 | H | S | 0 | H | $CF_3$ | $CH_3$ | — | $CH(CH_3)COO^cC_6H_{11}$ |
| 2-322 | F | S | 0 | H | $CF_3$ | $CH_3$ | — | H |
| 2-323 | F | S | 0 | H | $CF_3$ | $CH_3$ | — | $CH_3$ |
| 2-324 | F | S | 0 | H | $CF_3$ | $CH_3$ | — | $C_2H_5$ |
| 2-325 | F | S | 0 | H | $CF_3$ | $CH_3$ | — | $^nC_3H_7$ |
| 2-326 | F | S | 0 | H | $CF_3$ | $CH_3$ | — | $^nC_4H_9$ |
| 2-327 | F | S | 0 | H | $CF_3$ | $CH_3$ | — | $^iC_3H_7$ |
| 2-328 | F | S | 0 | H | $CF_3$ | $CH_3$ | — | $^iC_4H_9$ |
| 2-329 | F | S | 0 | H | $CF_3$ | $CH_3$ | — | $CH_2CH_2Cl$ |
| 2-330 | F | S | 0 | H | $CF_3$ | $CH_3$ | — | $CH_2CH_2Br$ |
| 2-331 | F | S | 0 | H | $CF_3$ | $CH_3$ | — | $CH_2CH=CH_2$ |
| 2-332 | F | S | 0 | H | $CF_3$ | $CH_3$ | — | $CH(CH_3)CH=CH_2$ |
| 2-333 | F | S | 0 | H | $CF_3$ | $CH_3$ | — | $CH_2CCl=CH_2$ |
| 2-334 | F | S | 0 | H | $CF_3$ | $CH_3$ | — | $CH_2C\equiv CH$ |
| 2-335 | F | S | 0 | H | $CF_3$ | $CH_3$ | — | $CH(CH_3)C\equiv CH$ |
| 2-336 | F | S | 0 | H | $CF_3$ | $CH_3$ | — | $CH_2CN$ |
| 2-337 | F | S | 0 | H | $CF_3$ | $CH_3$ | — | $CH_2OCH_3$ |
| 2-338 | F | S | 0 | H | $CF_3$ | $CH_3$ | — | $CH_2OC_2H_5$ |
| 2-339 | F | S | 0 | H | $CF_3$ | $CH_3$ | — | $CH_2COOH$ |
| 2-340 | F | S | 0 | H | $CF_3$ | $CH_3$ | — | $CH_2COOCH_3$ |
| 2-341 | F | S | 0 | H | $CF_3$ | $CH_3$ | — | $CH_2COOC_2H_5$ |
| 2-342 | F | S | 0 | H | $CF_3$ | $CH_3$ | — | $CH_2COO^nC_3H_7$ |
| 2-343 | F | S | 0 | H | $CF_3$ | $CH_3$ | — | $CH_2COO^nC_4H_9$ |
| 2-344 | F | S | 0 | H | $CF_3$ | $CH_3$ | — | $CH_2COO^nC_5H_{11}$ |
| 2-345 | F | S | 0 | H | $CF_3$ | $CH_3$ | — | $CH_2COO^iC_3H_7$ |
| 2-346 | F | S | 0 | H | $CF_3$ | $CH_3$ | — | $CH_2COO^cC_5H_9$ |
| 2-347 | F | S | 0 | H | $CF_3$ | $CH_3$ | — | $CH_2COO^cC_6H_{11}$ |
| 2-348 | F | S | 0 | H | $CF_3$ | $CH_3$ | — | $CH(CH_3)COOH$ |
| 2-349 | F | S | 0 | H | $CF_3$ | $CH_3$ | — | $CH(CH_3)COOCH_3$ |
| 2-350 | F | S | 0 | H | $CF_3$ | $CH_3$ | — | $CH(CH_3)COOC_2H_5$ |
| 2-351 | F | S | 0 | H | $CF_3$ | $CH_3$ | — | $CH(CH_3)COO^nC_3H_7$ |
| 2-352 | F | S | 0 | H | $CF_3$ | $CH_3$ | — | $CH(CH_3)COO^nC_4H_9$ |
| 2-353 | F | S | 0 | H | $CF_3$ | $CH_3$ | — | $CH(CH_3)COO^nC_5H_{11}$ |
| 2-354 | F | S | 0 | H | $CF_3$ | $CH_3$ | — | $CH(CH_3)COO^iC_3H_7$ |
| 2-355 | F | S | 0 | H | $CF_3$ | $CH_3$ | — | $CH(CH_3)COO^cC_5H_9$ |
| 2-356 | F | S | 0 | H | $CF_3$ | $CH_3$ | — | $CH(CH_3)COO^cC_6H_{11}$ |
| 2-357 | H | O | 0 | H | $CF_3$ | $CH_3$ | — | H |
| 2-358 | H | O | 0 | H | $CF_3$ | $CH_3$ | — | $CH_3$ |
| 2-359 | H | O | 0 | H | $CF_3$ | $CH_3$ | — | $C_2H_5$ |
| 2-360 | H | O | 0 | H | $CF_3$ | $CH_3$ | — | $^nC_3H_7$ |
| 2-361 | H | O | 0 | H | $CF_3$ | $CH_3$ | — | $^nC_4H_9$ |
| 2-362 | H | O | 0 | H | $CF_3$ | $CH_3$ | — | $^iC_3H_7$ |
| 2-363 | H | O | 0 | H | $CF_3$ | $CH_3$ | — | $^iC_4H_9$ |
| 2-364 | H | O | 0 | H | $CF_3$ | $CH_3$ | — | $CH_2CH=CH_2$ |
| 2-365 | H | O | 0 | H | $CF_3$ | $CH_3$ | — | $CH(CH_3)CH=CH_2$ |
| 2-366 | H | O | 0 | H | $CF_3$ | $CH_3$ | — | $CH_2C\equiv CH$ |
| 2-367 | H | O | 0 | H | $CF_3$ | $CH_3$ | — | $CH(CH_3)C\equiv CH$ |
| 2-368 | H | O | 0 | H | $CF_3$ | $CH_3$ | — | $CH_2OCH_3$ |
| 2-369 | H | O | 0 | H | $CF_3$ | $CH_3$ | — | $CH_2OC_2H_5$ |
| 2-370 | F | O | 0 | H | $CF_3$ | $CH_3$ | — | H |
| 2-371 | F | O | 0 | H | $CF_3$ | $CH_3$ | — | $CH_3$ |
| 2-372 | F | O | 0 | H | $CF_3$ | $CH_3$ | — | $C_2H_5$ |
| 2-373 | F | O | 0 | H | $CF_3$ | $CH_3$ | — | $^nC_3H_7$ |
| 2-374 | F | O | 0 | H | $CF_3$ | $CH_3$ | — | $^nC_4H_9$ |
| 2-375 | F | O | 0 | H | $CF_3$ | $CH_3$ | — | $CH_2CH=CH_2$ |
| 2-376 | F | O | 0 | H | $CF_3$ | $CH_3$ | — | $CH(CH_3)CH=CH_2$ |
| 2-377 | F | O | 0 | H | $CF_3$ | $CH_3$ | — | $CH_2C\equiv CH$ |
| 2-378 | F | O | 0 | H | $CF_3$ | $CH_3$ | — | $CH(CH_3)C\equiv CH$ |
| 2-379 | F | O | 0 | H | $CF_3$ | $CH_3$ | — | $CH_2OCH_3$ |
| 2-380 | F | O | 0 | H | $CF_3$ | $CH_3$ | — | $CH_2OC_2H_5$ |

TABLE 3

Compounds of the formula:

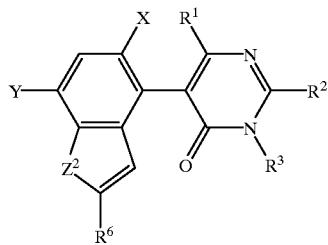
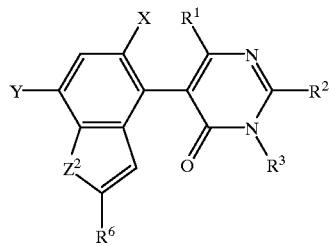

| Compound No. | X | Y | $Z^2$ | $R^1$ | $R^2$ | $R^3$ | $R^6$ |
|---|---|---|---|---|---|---|---|
| 3-1 | H | F | O | H | $CH_3$ | $C_2H_5$ | $CH_3$ |
| 3-2 | H | Cl | O | H | $CH_3$ | $C_2H_5$ | $CH_3$ |
| 3-3 | H | Br | O | H | $CH_3$ | $C_2H_5$ | $CH_3$ |
| 3-4 | F | F | O | H | $CH_3$ | $C_2H_5$ | $CH_3$ |
| 3-5 | F | Cl | O | H | $CH_3$ | $C_2H_5$ | $CH_3$ |
| 3-6 | F | Br | O | H | $CH_3$ | $C_2H_5$ | $CH_3$ |
| 3-7 | H | F | O | H | $CH_3$ | $CH_3$ | $CH_3$ |
| 3-8 | H | Cl | O | H | $CH_3$ | $CH_3$ | $CH_3$ |
| 3-9 | H | Br | O | H | $CH_3$ | $CH_3$ | $CH_3$ |
| 3-10 | F | F | O | H | $CH_3$ | $CH_3$ | $CH_3$ |
| 3-11 | F | Cl | O | H | $CH_3$ | $CH_3$ | $CH_3$ |
| 3-12 | F | Br | O | H | $CH_3$ | $CH_3$ | $CH_3$ |
| 3-13 | H | F | O | H | $CH_3$ | $CH_3$ | $C_2H_5$ |
| 3-14 | H | Cl | O | H | $CH_3$ | $C_2H_5$ | $C_2H_5$ |
| 3-15 | H | Br | O | H | $CH_3$ | $C_2H_5$ | $C_2H_5$ |
| 3-16 | F | F | O | H | $CH_3$ | $C_2H_5$ | $C_2H_5$ |
| 3-17 | F | Cl | O | H | $CH_3$ | $C_2H_5$ | $C_2H_5$ |
| 3-18 | F | Br | O | H | $CH_3$ | $C_2H_5$ | $C_2H_5$ |
| 3-19 | H | F | O | H | $CH_3$ | $CH_3$ | $C_2H_5$ |
| 3-20 | H | Cl | O | H | $CH_3$ | $CH_3$ | $C_2H_5$ |
| 3-21 | H | Br | O | H | $CH_3$ | $CH_3$ | $C_2H_5$ |
| 3-22 | F | F | O | H | $CH_3$ | $CH_3$ | $C_2H_5$ |
| 3-23 | F | Cl | O | H | $CH_3$ | $CH_3$ | $C_2H_5$ |
| 3-24 | F | Br | O | H | $CH_3$ | $CH_3$ | $C_2H_5$ |
| 3-25 | H | F | O | H | $CH_3$ | $CH_3$ | $CH_2Br$ |
| 3-26 | H | F | O | H | $CH_3$ | $CH_3$ | $CHBr_2$ |
| 3-27 | H | F | O | H | $CH_3$ | $CH_3$ | $CBr_3$ |
| 3-28 | H | F | O | H | $CH_3$ | $CH_3$ | $CHO$ |
| 3-29 | H | F | O | H | $CH_3$ | $CH_3$ | $CN$ |
| 3-30 | H | F | O | H | $CH_3$ | $CH_3$ | $COOH$ |
| 3-31 | H | F | O | H | $CH_3$ | $CH_3$ | $CH_2OH$ |
| 3-32 | H | F | O | H | $CH_3$ | $CH_3$ | $CH_2OCH_3$ |
| 3-33 | H | F | O | H | $CH_3$ | $CH_3$ | $CH_2OC_2H_5$ |
| 3-34 | H | F | O | H | $CH_3$ | $CH_3$ | $CH_2O^iC_3H_7$ |
| 3-35 | H | F | O | H | $CH_3$ | $CH_3$ | $CH_2OCH_2OCH_3$ |
| 3-36 | H | F | O | H | $CH_3$ | $CH_3$ | $CH_2OCH_2OC_2H_5$ |
| 3-37 | H | F | O | H | $CH_3$ | $CH_3$ | $CH_2OCOCH_3$ |
| 3-38 | H | F | O | H | $CH_3$ | $CH_3$ | $CH_2OCOC_2H_5$ |
| 3-39 | H | F | O | H | $CH_3$ | $CH_3$ | $CH_2OCO^iC_3H_7$ |
| 3-40 | H | F | O | H | $CH_3$ | $CH_3$ | $CH_2OCOCH_2Cl$ |
| 3-41 | H | F | O | H | $CH_3$ | $CH_3$ | $CH_2OCOCCl_3$ |
| 3-42 | H | F | O | H | $CH_3$ | $CH_3$ | $CH_2OCOCF_3$ |
| 3-43 | H | F | O | H | $CH_3$ | $CH_3$ | $COOCH_3$ |
| 3-44 | H | F | O | H | $CH_3$ | $CH_3$ | $COOC_2H_5$ |
| 3-45 | H | F | O | H | $CH_3$ | $CH_3$ | $COO^nC_3H_7$ |
| 3-46 | H | F | O | H | $CH_3$ | $CH_3$ | $COO^nC_4H_9$ |
| 3-47 | H | F | O | H | $CH_3$ | $CH_3$ | $COO^nC_5H_{11}$ |
| 3-48 | H | F | O | H | $CH_3$ | $CH_3$ | $COO^iC_3H_7$ |
| 3-49 | H | F | O | H | $CH_3$ | $CH_3$ | $COCH_3$ |
| 3-50 | H | F | O | H | $CH_3$ | $CH_3$ | $COC_2H_5$ |
| 3-51 | H | Cl | O | H | $CH_3$ | $CH_3$ | $CH_2Br$ |
| 3-52 | H | Cl | O | H | $CH_3$ | $CH_3$ | $CHBr_2$ |
| 3-53 | H | Cl | O | H | $CH_3$ | $CH_3$ | $CBr_3$ |
| 3-54 | H | Cl | O | H | $CH_3$ | $CH_3$ | $CHO$ |
| 3-55 | H | Cl | O | H | $CH_3$ | $CH_3$ | $CN$ |
| 3-56 | H | Cl | O | H | $CH_3$ | $CH_3$ | $COOH$ |
| 3-57 | H | Cl | O | H | $CH_3$ | $CH_3$ | $CH_2OH$ |
| 3-58 | H | Cl | O | H | $CH_3$ | $CH_3$ | $CH_2OCH_3$ |
| 3-59 | H | Cl | O | H | $CH_3$ | $CH_3$ | $CH_2OC_2H_5$ |
| 3-60 | H | Cl | O | H | $CH_3$ | $CH_3$ | $CH_2O^iC_3H_7$ |
| 3-61 | H | Cl | O | H | $CH_3$ | $CH_3$ | $CH_2OCH_2OCH_3$ |
| 3-62 | H | Cl | O | H | $CH_3$ | $CH_3$ | $CH_2OCH_2OC_2H_5$ |
| 3-63 | H | Cl | O | H | $CH_3$ | $CH_3$ | $CH_2OCOCH_3$ |
| 3-64 | H | Cl | O | H | $CH_3$ | $CH_3$ | $CH_2OCOC_2H_5$ |
| 3-65 | H | Cl | O | H | $CH_3$ | $CH_3$ | $CH_2OCO^iC_3H_7$ |
| 3-66 | H | Cl | O | H | $CH_3$ | $CH_3$ | $CH_2OCOCH_2Cl$ |
| 3-67 | H | Cl | O | H | $CH_3$ | $CH_3$ | $CH_2OCOCCl_3$ |
| 3-68 | H | Cl | O | H | $CH_3$ | $CH_3$ | $CH_2OCOCF_3$ |
| 3-69 | H | Cl | O | H | $CH_3$ | $CH_3$ | $COOCH_3$ |
| 3-70 | H | Cl | O | H | $CH_3$ | $CH_3$ | $COOC_2H_5$ |
| 3-71 | H | Cl | O | H | $CH_3$ | $CH_3$ | $COO^nC_3H_7$ |
| 3-72 | H | Cl | O | H | $CH_3$ | $CH_3$ | $COO^nC_4H_9$ |
| 3-73 | H | Cl | O | H | $CH_3$ | $CH_3$ | $COO^nC_5H_{11}$ |
| 3-74 | H | Cl | O | H | $CH_3$ | $CH_3$ | $COO^iC_3H_7$ |
| 3-75 | H | Cl | O | H | $CH_3$ | $CH_3$ | $COCH_3$ |
| 3-76 | H | Cl | O | H | $CH_3$ | $CH_3$ | $COC_2H_5$ |
| 3-77 | F | F | O | O | $CH_3$ | $CH_3$ | $CH_2Br$ |
| 3-78 | F | F | O | H | $CH_3$ | $CH_3$ | $CHBr_2$ |
| 3-79 | F | F | O | H | $CH_3$ | $CH_3$ | $CBr_3$ |
| 3-80 | F | F | O | H | $CH_3$ | $CH_3$ | $CHO$ |
| 3-81 | F | F | O | H | $CH_3$ | $CH_3$ | $CN$ |
| 3-82 | F | F | O | H | $CH_3$ | $CH_3$ | $COOH$ |
| 3-83 | F | F | O | H | $CH_3$ | $CH_3$ | $CH_2OH$ |
| 3-84 | F | F | O | H | $CH_3$ | $CH_3$ | $CH_2OCH_3$ |
| 3-85 | F | F | O | H | $CH_3$ | $CH_3$ | $CH_2OC_2H_5$ |
| 3-86 | F | F | O | H | $CH_3$ | $CH_3$ | $CH_2O^iC_3H_7$ |
| 3-87 | F | F | O | H | $CH_3$ | $CH_3$ | $CH_2OCH_2OCH_3$ |
| 3-88 | F | F | O | H | $CH_3$ | $CH_3$ | $CH_2OCH_2OC_2H_5$ |
| 3-89 | F | F | O | H | $CH_3$ | $CH_3$ | $CH_2OCOCH_3$ |
| 3-90 | F | F | O | H | $CH_3$ | $CH_3$ | $CH_2OCOC_2H_5$ |
| 3-91 | F | F | O | H | $CH_3$ | $CH_3$ | $CH_2OCO^iC_3H_7$ |
| 3-92 | F | F | O | H | $CH_3$ | $CH_3$ | $CH_2OCOCH_2Cl$ |
| 3-93 | F | F | O | H | $CH_3$ | $CH_3$ | $CH_2OCOCCl_3$ |
| 3-94 | F | F | O | H | $CH_3$ | $CH_3$ | $CH_2OCOCF_3$ |
| 3-95 | F | F | O | H | $CH_3$ | $CH_3$ | $COOCH_3$ |
| 3-96 | F | F | O | H | $CH_3$ | $CH_3$ | $COOC_2H_5$ |
| 3-97 | F | F | O | H | $CH_3$ | $CH_3$ | $COO^nC_3H_7$ |
| 3-98 | F | F | O | H | $CH_3$ | $CH_3$ | $COO^nC_4H_9$ |
| 3-99 | F | F | O | H | $CH_3$ | $CH_3$ | $COO^nC_5H_{11}$ |
| 3-100 | F | F | O | H | $CH_3$ | $CH_3$ | $COO^iC_3H_7$ |
| 3-101 | F | F | O | H | $CH_3$ | $CH_3$ | $COCH_3$ |
| 3-102 | F | F | O | H | $CH_3$ | $CH_3$ | $COC_2H_5$ |
| 3-103 | F | Cl | O | H | $CH_3$ | $CH_3$ | $CH_2Br$ |
| 3-104 | F | Cl | O | H | $CH_3$ | $CH_3$ | $CHBr_2$ |
| 3-105 | F | Cl | O | H | $CH_3$ | $CH_3$ | $CBr_3$ |
| 3-106 | F | Cl | O | H | $CH_3$ | $CH_3$ | $CHO$ |
| 3-107 | F | Cl | O | H | $CH_3$ | $CH_3$ | $CN$ |
| 3-108 | F | Cl | O | H | $CH_3$ | $CH_3$ | $COOH$ |
| 3-109 | F | Cl | O | H | $CH_3$ | $CH_3$ | $CH_2OH$ |
| 3-110 | F | Cl | O | H | $CH_3$ | $CH_3$ | $CH_2OCH_3$ |
| 3-111 | F | Cl | O | H | $CH_3$ | $CH_3$ | $CH_2OC_2H_5$ |
| 3-112 | F | Cl | O | H | $CH_3$ | $CH_3$ | $CH_2O^iC_3H_7$ |
| 3-113 | F | Cl | O | H | $CH_3$ | $CH_3$ | $CH_2OCH_2OCH_3$ |
| 3-114 | F | Cl | O | H | $CH_3$ | $CH_3$ | $CH_2OCH_2OC_2H_5$ |
| 3-115 | F | Cl | O | H | $CH_3$ | $CH_3$ | $CH_2OCOCH_3$ |
| 3-116 | F | Cl | O | H | $CH_3$ | $CH_3$ | $CH_2OCOC_2H_5$ |
| 3-117 | F | Cl | O | H | $CH_3$ | $CH_3$ | $CH_2OCO^iC_3H_7$ |
| 3-118 | F | Cl | O | H | $CH_3$ | $CH_3$ | $CH_2OCOCH_2Cl$ |
| 3-119 | F | Cl | O | H | $CH_3$ | $CH_3$ | $CH_2OCOCCl_3$ |
| 3-120 | F | Cl | O | H | $CH_3$ | $CH_3$ | $CH_2OCOCF_3$ |
| 3-121 | F | Cl | O | H | $CH_3$ | $CH_3$ | $COOCH_3$ |
| 3-122 | F | Cl | O | H | $CH_3$ | $CH_3$ | $COOC_2H_5$ |

TABLE 3-continued

Compounds of the formula:

[Structure: benzofuran fused with pyrimidinone, substituents X, Y, Z², R¹, R², R³, R⁶]

| Compound No. | X | Y | Z² | R¹ | R² | R³ | R⁶ |
|---|---|---|---|---|---|---|---|
| 3-123 | F | Cl | O | H | $CH_3$ | $CH_3$ | $COO^nC_3H_7$ |
| 3-124 | F | Cl | O | H | $CH_3$ | $CH_3$ | $COO^nC_4H_9$ |
| 3-125 | F | Cl | O | H | $CH_3$ | $CH_3$ | $COO^nC_5H_{11}$ |
| 3-126 | F | Cl | O | H | $CH_3$ | $CH_3$ | $COO^iC_3H_7$ |
| 3-127 | F | Cl | O | H | $CH_3$ | $CH_3$ | $COCH_3$ |
| 3-128 | F | Cl | O | H | $CH_3$ | $CH_3$ | $COC_2H_5$ |
| 3-129 | H | F | O | H | $CF_3$ | $C_2H_5$ | $CH_3$ |
| 3-130 | H | Cl | O | H | $CF_3$ | $C_2H_5$ | $CH_3$ |
| 3-131 | H | Br | O | H | $CF_3$ | $C_2H_5$ | $CH_3$ |
| 3-132 | F | F | O | H | $CF_3$ | $C_2H_5$ | $CH_3$ |
| 3-133 | F | Cl | O | H | $CF_3$ | $C_2H_5$ | $CH_3$ |
| 3-134 | F | Br | O | H | $CF_3$ | $C_2H_5$ | $CH_3$ |
| 3-135 | H | F | O | H | $CF_3$ | $CH_3$ | $CH_3$ |
| 3-136 | H | Cl | O | H | $CF_3$ | $CH_3$ | $CH_3$ |
| 3-137 | H | Br | O | H | $CF_3$ | $CH_3$ | $CH_3$ |
| 3-138 | F | F | O | H | $CF_3$ | $CH_3$ | $CH_3$ |
| 3-139 | F | Cl | O | H | $CF_3$ | $CH_3$ | $CH_3$ |
| 3-140 | F | Br | O | H | $CF_3$ | $CH_3$ | $CH_3$ |
| 3-141 | H | F | O | H | $CF_3$ | $C_2H_5$ | $C_2H_5$ |
| 3-142 | H | Cl | O | H | $CF_3$ | $C_2H_5$ | $C_2H_5$ |
| 3-143 | H | Br | O | H | $CF_3$ | $C_2H_5$ | $C_2H_5$ |
| 3-144 | F | F | O | H | $CF_3$ | $C_2H_5$ | $C_2H_5$ |
| 3-145 | F | Cl | O | H | $CF_3$ | $C_2H_5$ | $C_2H_5$ |
| 3-146 | F | Br | O | H | $CF_3$ | $C_2H_5$ | $C_2H_5$ |
| 3-147 | H | F | O | H | $CF_3$ | $CH_3$ | $C_2H_5$ |
| 3-148 | H | Cl | O | H | $CF_3$ | $CH_3$ | $C_2H_5$ |
| 3-149 | H | Br | O | H | $CF_3$ | $CH_3$ | $C_2H_5$ |
| 3-150 | F | F | O | H | $CF_3$ | $CH_3$ | $C_2H_5$ |
| 3-151 | F | Cl | O | H | $CF_3$ | $CH_3$ | $C_2H_5$ |
| 3-152 | F | Br | O | H | $CF_3$ | $CH_3$ | $C_2H_5$ |
| 3-153 | H | F | O | H | $CF_3$ | $CH_3$ | $CH_2Br$ |
| 3-154 | H | F | O | H | $CF_3$ | $CH_3$ | $CHBr_2$ |
| 3-155 | H | F | O | H | $CF_3$ | $CH_3$ | $CBr_3$ |
| 3-156 | H | F | O | H | $CF_3$ | $CH_3$ | $CHO$ |
| 3-157 | H | F | O | H | $CF_3$ | $CH_3$ | $CN$ |
| 3-158 | H | F | O | H | $CF_3$ | $CH_3$ | $COOH$ |
| 3-159 | H | F | O | H | $CF_3$ | $CH_3$ | $CH_2OH$ |
| 3-160 | H | F | O | H | $CF_3$ | $CH_3$ | $CH_2OCH_3$ |
| 3-161 | H | F | O | H | $CF_3$ | $CH_3$ | $CH_2OC_2H_5$ |
| 3-162 | H | F | O | H | $CF_3$ | $CH_3$ | $CH_2O^iC_3H_7$ |
| 3-163 | H | F | O | H | $CF_3$ | $CH_3$ | $CH_2OCH_2OCH_3$ |
| 3-164 | H | F | O | H | $CF_3$ | $CH_3$ | $CH_2OCH_2OC_2H_5$ |
| 3-165 | H | F | O | H | $CF_3$ | $CH_3$ | $CH_2OCOCH_3$ |
| 3-166 | H | F | O | H | $CF_3$ | $CH_3$ | $CH_2OCOC_2H_5$ |
| 3-167 | H | F | O | H | $CF_3$ | $CH_3$ | $CH_2OCO^iC_3H_7$ |
| 3-168 | H | F | O | H | $CF_3$ | $CH_3$ | $CH_2OCOCH_2Cl$ |
| 3-169 | H | F | O | H | $CF_3$ | $CH_3$ | $CH_2OCOCCl_3$ |
| 3-170 | H | F | O | H | $CF_3$ | $CH_3$ | $CH_2OCOCF_3$ |
| 3-171 | H | F | O | H | $CF_3$ | $CH_3$ | $COOCH_3$ |
| 3-172 | H | F | O | H | $CF_3$ | $CH_3$ | $COOC_2H_5$ |
| 3-173 | H | F | O | H | $CF_3$ | $CH_3$ | $COO^nC_3H_7$ |
| 3-174 | H | F | O | H | $CF_3$ | $CH_3$ | $COO^nC_4H_9$ |
| 3-175 | H | F | O | H | $CF_3$ | $CH_3$ | $COO^nC_5H_{11}$ |
| 3-176 | H | F | O | H | $CF_3$ | $CH_3$ | $COO^iC_3H_7$ |
| 3-177 | H | F | O | H | $CF_3$ | $CH_3$ | $COCH_3$ |
| 3-178 | H | F | O | H | $CF_3$ | $CH_3$ | $COC_2H_5$ |
| 3-179 | H | Cl | O | H | $CF_3$ | $CH_3$ | $CH_2Br$ |
| 3-180 | H | Cl | O | H | $CF_3$ | $CH_3$ | $CHBr_2$ |
| 3-181 | H | Cl | O | H | $CF_3$ | $CH_3$ | $CBr_3$ |
| 3-182 | H | Cl | O | H | $CF_3$ | $CH_3$ | $CHO$ |
| 3-183 | H | Cl | O | H | $CF_3$ | $CH_3$ | $CN$ |
| 3-184 | H | Cl | O | H | $CF_3$ | $CH_3$ | $COOH$ |
| 3-185 | H | Cl | O | H | $CF_3$ | $CH_3$ | $CH_2OH$ |
| 3-186 | H | Cl | O | H | $CF_3$ | $CH_3$ | $CH_2OCH_3$ |
| 3-187 | H | Cl | O | H | $CF_3$ | $CH_3$ | $CH_2OC_2H_5$ |
| 3-188 | H | Cl | O | H | $CF_3$ | $CH_3$ | $CH_2O^iC_3H_7$ |
| 3-189 | H | Cl | O | H | $CF_3$ | $CH_3$ | $CH_2OCH_2OCH_3$ |
| 3-190 | H | Cl | O | H | $CF_3$ | $CH_3$ | $CH_2OCH_2OC_2H_5$ |
| 3-191 | H | Cl | O | H | $CF_3$ | $CH_3$ | $CH_2OCOCH_3$ |
| 3-192 | H | Cl | O | H | $CF_3$ | $CH_3$ | $CH_2OCOC_2H_5$ |
| 3-193 | H | Cl | O | H | $CF_3$ | $CH_3$ | $CH_2OCO^iC_3H_7$ |
| 3-194 | H | Cl | O | H | $CF_3$ | $CH_3$ | $CH_2OCOCH_2Cl$ |
| 3-195 | H | Cl | O | H | $CF_3$ | $CH_3$ | $CH_2OCOCCl_3$ |
| 3-196 | H | Cl | O | H | $CF_3$ | $CH_3$ | $CH_2OCOCF_3$ |
| 3-197 | H | Cl | O | H | $CF_3$ | $CH_3$ | $COOCH_3$ |
| 3-198 | H | Cl | O | H | $CF_3$ | $CH_3$ | $COOC_2H_5$ |
| 3-199 | H | Cl | O | H | $CF_3$ | $CH_3$ | $COO^nC_3H_7$ |
| 3-200 | H | Cl | O | H | $CF_3$ | $CH_3$ | $COO^nC_4H_9$ |
| 3-201 | H | Cl | O | H | $CF_3$ | $CH_3$ | $COO^nC_5H_{11}$ |
| 3-202 | H | Cl | O | H | $CF_3$ | $CH_3$ | $COO^iC_3H_7$ |
| 3-203 | H | Cl | O | H | $CF_3$ | $CH_3$ | $COCH_3$ |
| 3-204 | H | Cl | O | H | $CF_3$ | $CH_3$ | $COC_2H_5$ |
| 3-205 | F | F | O | H | $CF_3$ | $CH_3$ | $CH_2Br$ |
| 3-206 | F | F | O | H | $CF_3$ | $CH_3$ | $CHBr_2$ |
| 3-207 | F | F | O | H | $CF_3$ | $CH_3$ | $CBr_3$ |
| 3-208 | F | F | O | H | $CF_3$ | $CH_3$ | $CHO$ |
| 3-209 | F | F | O | H | $CF_3$ | $CH_3$ | $CN$ |
| 3-210 | F | F | O | H | $CF_3$ | $CH_3$ | $COOH$ |
| 3-211 | F | F | O | H | $CF_3$ | $CH_3$ | $CH_2OH$ |
| 3-212 | F | F | O | H | $CF_3$ | $CH_3$ | $CH_2OCH_3$ |
| 3-213 | F | F | O | H | $CF_3$ | $CH_3$ | $CH_2OC_2H_5$ |
| 3-214 | F | F | O | H | $CF_3$ | $CH_3$ | $CH_2O^iC_3H_7$ |
| 3-215 | F | F | O | H | $CF_3$ | $CH_3$ | $CH_2OCH_2OCH_3$ |
| 3-216 | F | F | O | H | $CF_3$ | $CH_3$ | $CH_2OCH_2OC_2H_5$ |
| 3-217 | F | F | O | H | $CF_3$ | $CH_3$ | $CH_2OCOCH_3$ |
| 3-218 | F | F | O | H | $CF_3$ | $CH_3$ | $CH_2OCOC_2H_5$ |
| 3-219 | F | F | O | H | $CF_3$ | $CH_3$ | $CH_2OCO^iC_3H_7$ |
| 3-220 | F | F | O | H | $CF_3$ | $CH_3$ | $CH_2OCOCH_2Cl$ |
| 3-221 | F | F | O | H | $CF_3$ | $CH_3$ | $CH_2OCOCCl_3$ |
| 3-222 | F | F | O | H | $CF_3$ | $CH_3$ | $CH_2OCOCF_3$ |
| 3-223 | F | F | O | H | $CF_3$ | $CH_3$ | $COOCH_3$ |
| 3-224 | F | F | O | H | $CF_3$ | $CH_3$ | $COOC_2H_5$ |
| 3-225 | F | F | O | H | $CF_3$ | $CH_3$ | $COO^nC_3H_7$ |
| 3-226 | F | F | O | H | $CF_3$ | $CH_3$ | $COO^nC_4H_9$ |
| 3-227 | F | F | O | H | $CF_3$ | $CH_3$ | $COO^nC_5H_{11}$ |
| 3-228 | F | F | O | H | $CF_3$ | $CH_3$ | $COO^iC_3H_7$ |
| 3-229 | F | F | O | H | $CF_3$ | $CH_3$ | $COCH_3$ |
| 3-230 | F | F | O | H | $CF_3$ | $CH_3$ | $COC_2H_5$ |
| 3-231 | F | Cl | O | H | $CF_3$ | $CH_3$ | $CH_2Br$ |
| 3-232 | F | Cl | O | H | $CF_3$ | $CH_3$ | $CHBr_2$ |
| 3-233 | F | Cl | O | H | $CF_3$ | $CH_3$ | $CBr_3$ |
| 3-234 | F | Cl | O | H | $CF_3$ | $CH_3$ | $CHO$ |
| 3-235 | F | Cl | O | H | $CF_3$ | $CH_3$ | $CN$ |
| 3-236 | F | Cl | O | H | $CF_3$ | $CH_3$ | $COOH$ |
| 3-237 | F | Cl | O | H | $CF_3$ | $CH_3$ | $CH_2OH$ |
| 3-238 | F | Cl | O | H | $CF_3$ | $CH_3$ | $CH_2OCH_3$ |
| 3-239 | F | Cl | O | H | $CF_3$ | $CH_3$ | $CH_2OC_2H_5$ |
| 3-240 | F | Cl | O | H | $CF_3$ | $CH_3$ | $CH_2O^iC_3H_7$ |
| 3-241 | F | Cl | O | H | $CF_3$ | $CH_3$ | $CH_2OCH_2OCH_3$ |
| 3-242 | F | Cl | O | H | $CF_3$ | $CH_3$ | $CH_2OCH_2OC_2H_5$ |
| 3-243 | F | Cl | O | H | $CF_3$ | $CH_3$ | $CH_2OCOCH_3$ |
| 3-244 | F | Cl | O | H | $CF_3$ | $CH_3$ | $CH_2OCOC_2H_5$ |

TABLE 3-continued

Compounds of the formula:

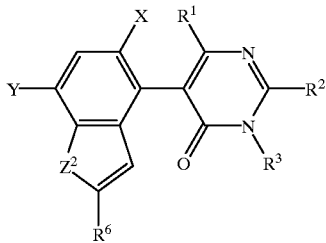

| Compound No. | X | Y | Z² | R¹ | R² | R³ | R⁶ |
|---|---|---|---|---|---|---|---|
| 3-245 | F | Cl | O | H | CF₃ | CH₃ | CH₂OCO$^i$C₃H₇ |
| 3-246 | F | Cl | O | H | CF₃ | CH₃ | CH₂OCOCH₂Cl |
| 3-247 | F | Cl | O | H | CF₃ | CH₃ | CH₂OCOCCl₃ |
| 3-248 | F | Cl | O | H | CF₃ | CH₃ | CH₂OCOCF₃ |
| 3-249 | F | Cl | O | H | CF₃ | CH₃ | COOCH₃ |
| 3-250 | F | Cl | O | H | CF₃ | CH₃ | COOC₂H₅ |
| 3-251 | F | Cl | O | H | CF₃ | CH₃ | COO$^n$C₃H₇ |
| 3-252 | F | Cl | O | H | CF₃ | CH₃ | COO$^n$C₄H₉ |
| 3-253 | F | Cl | O | H | CF₃ | CH₃ | COO$^n$C₅H₁₁ |
| 3-254 | F | Cl | O | H | CF₃ | CH₃ | COO$^i$C₃H₇ |
| 3-255 | F | Cl | O | H | CF₃ | CH₃ | COCH₃ |
| 3-256 | F | Cl | O | H | CF₃ | CH₃ | COC₂H₅ |

TABLE 4

Compounds of the formula:

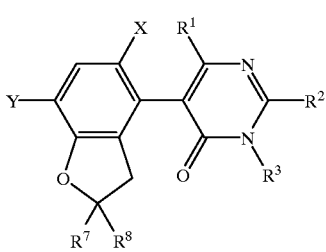

| Compound No. | X | Y | R¹ | R² | R³ | R⁷ | R⁸ |
|---|---|---|---|---|---|---|---|
| 4-1 | H | F | H | CH₃ | C₂H₅ | H | CH₃ |
| 4-2 | H | Cl | H | CH₃ | C₂H₅ | H | CH₃ |
| 4-3 | H | Br | H | CH₃ | C₂H₅ | H | CH₃ |
| 4-4 | H | F | H | CH₃ | C₂H₅ | H | CH₂OH |
| 4-5 | H | Cl | H | CH₃ | C₂H₅ | H | CH₂OH |
| 4-6 | H | Br | H | CH₃ | C₂H₅ | H | CH₂OH |
| 4-7 | H | F | H | CH₃ | C₂H₅ | CH₃ | CH₃ |
| 4-8 | H | Cl | H | CH₃ | C₂H₅ | CH₃ | CH₃ |
| 4-9 | H | Br | H | CH₃ | C₂H₅ | CH₃ | CH₃ |
| 4-10 | H | F | H | CH₃ | C₂H₅ | CH₃ | CH₂OH |
| 4-11 | H | Cl | H | CH₃ | C₂H₅ | CH₃ | CH₂OH |
| 4-12 | H | Br | H | CH₃ | C₂H₅ | CH₃ | CH₂OH |
| 4-13 | F | F | H | CH₃ | C₂H₅ | H | CH₃ |
| 4-14 | F | Cl | H | CH₃ | C₂H₅ | H | CH₃ |
| 4-15 | F | Br | H | CH₃ | C₂H₅ | H | CH₃ |
| 4-16 | F | F | H | CH₃ | C₂H₅ | H | CH₂OH |
| 4-17 | F | Cl | H | CH₃ | C₂H₅ | H | CH₂OH |
| 4-18 | F | Br | H | CH₃ | C₂H₅ | H | CH₂OH |
| 4-19 | F | F | H | CH₃ | C₂H₅ | CH₃ | CH₃ |
| 4-20 | F | Cl | H | CH₃ | C₂H₅ | CH₃ | CH₃ |
| 4-21 | F | Br | H | CH₃ | C₂H₅ | CH₃ | CH₃ |
| 4-22 | F | F | H | CH₃ | C₂H₅ | CH₃ | CH₂OH |
| 4-23 | F | Cl | H | CH₃ | C₂H₅ | CH₃ | CH₂OH |
| 4-24 | F | Br | H | CH₃ | C₂H₅ | CH₃ | CH₂OH |
| 4-25 | H | Cl | H | CH₃ | CH₃ | H | CH₂Cl |
| 4-26 | H | Cl | H | CH₃ | CH₃ | H | CH₂Br |

TABLE 4-continued

Compounds of the formula:

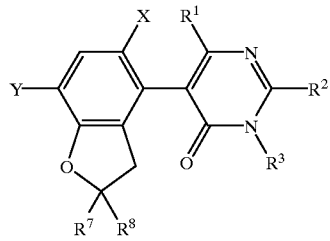

| Compound No. | X | Y | R¹ | R² | R³ | R⁷ | R⁸ |
|---|---|---|---|---|---|---|---|
| 4-27 | H | Cl | H | CH₃ | CH₃ | H | CH₂OCH₃ |
| 4-28 | H | Cl | H | CH₃ | CH₃ | H | CH₂OC₂H₅ |
| 4-29 | H | Cl | H | CH₃ | CH₃ | H | CH₂OCH₂OCH₃ |
| 4-30 | H | Cl | H | CH₃ | CH₃ | H | CH₂OCH₂OC₂H₅ |
| 4-31 | H | Cl | H | CH₃ | CH₃ | H | CH₂OCOCH₃ |
| 4-32 | H | Cl | H | CH₃ | CH₃ | H | CH₂OCOC₂H₅ |
| 4-33 | H | Cl | H | CH₃ | CH₃ | H | CH₂OCO$^i$C₃H₇ |
| 4-34 | H | Cl | H | CH₃ | CH₃ | H | CH₂OCOCH₂Cl |
| 4-35 | H | Cl | H | CH₃ | CH₃ | H | CH₂OCOCCl₃ |
| 4-36 | H | Cl | H | CH₃ | CH₃ | H | CH₂OCOCF₃ |
| 4-37 | H | Cl | H | CH₃ | CH₃ | H | COOH |
| 4-38 | H | Cl | H | CH₃ | CH₃ | H | COOCH₃ |
| 4-39 | H | Cl | H | CH₃ | CH₃ | H | COO₂H₅ |
| 4-40 | H | Cl | H | CH₃ | CH₃ | H | COO$^n$C₃H₇ |
| 4-41 | H | Cl | H | CH₃ | CH₃ | H | COO$^n$C₄H₉ |
| 4-42 | H | Cl | H | CH₃ | CH₃ | H | COO$^n$C₅H₁₁ |
| 4-43 | H | Cl | H | CH₃ | CH₃ | H | COO$^i$C₃H₇ |
| 4-44 | H | Cl | H | CH₃ | CH₃ | H | COO$^c$C₅H₉ |
| 4-45 | H | Cl | H | CH₃ | CH₃ | H | COO$^c$C₆H₁₁ |
| 4-46 | H | Cl | H | CH₃ | CH₃ | H | COOCH₂CH=CH₂ |
| 4-47 | H | Cl | H | CH₃ | CH₃ | H | COOCH₂C≡CH |
| 4-48 | H | Cl | H | CH₃ | CH₃ | H | CONH₂ |
| 4-49 | H | Cl | H | CH₃ | CH₃ | H | CONHCH₃ |
| 4-50 | H | Cl | H | CH₃ | CH₃ | H | CONHC₂H₅ |
| 4-51 | H | Cl | H | CH₃ | CH₃ | H | CON(CH₃)₂ |
| 4-52 | H | Cl | H | CH₃ | CH₃ | H | CON(C₂H₅)₂ |
| 4-53 | F | Cl | H | CH₃ | CH₃ | H | CH₂Cl |
| 4-54 | F | Cl | H | CH₃ | CH₃ | H | CH₂Br |
| 4-55 | F | Cl | H | CH₃ | CH₃ | H | CH₂OCH₃ |
| 4-56 | F | Cl | H | CH₃ | CH₃ | H | CH₂OC₂H₅ |
| 4-57 | F | Cl | H | CH₃ | CH₃ | H | CH₂OCH₂OCH₃ |
| 4-58 | F | Cl | H | CH₃ | CH₃ | H | CH₂OCH₂OC₂H₅ |
| 4-59 | F | Cl | H | CH₃ | CH₃ | H | CH₂OCOCH₃ |
| 4-60 | F | Cl | H | CH₃ | CH₃ | H | CH₂OCOC₂H₅ |
| 4-61 | F | Cl | H | CH₃ | CH₃ | H | CH₂OCO$^i$C₃H₇ |
| 4-62 | F | Cl | H | CH₃ | CH₃ | H | CH₂OCOCH₂Cl |
| 4-63 | F | Cl | H | CH₃ | CH₃ | H | CH₂OCOCCl₃ |
| 4-64 | F | Cl | H | CH₃ | CH₃ | H | CH₂OCOCF₃ |
| 4-65 | F | Cl | H | CH₃ | CH₃ | H | COOH |
| 4-66 | F | Cl | H | CH₃ | CH₃ | H | COOCH₃ |
| 4-67 | F | Cl | H | CH₃ | CH₃ | H | COOC₂H₅ |
| 4-68 | F | Cl | H | CH₃ | CH₃ | H | COO$^n$C₃H₇ |
| 4-69 | F | Cl | H | CH₃ | CH₃ | H | COO$^n$C₄H₉ |
| 4-70 | F | Cl | H | CH₃ | CH₃ | H | COO$^n$C₅H₁₁ |
| 4-71 | F | Cl | H | CH₃ | CH₃ | H | COO$^i$C₃H₇ |
| 4-72 | F | Cl | H | CH₃ | CH₃ | H | COO$^c$C₅H₉ |
| 4-73 | F | Cl | H | CH₃ | CH₃ | H | COO$^c$C₆H₁₁ |
| 4-74 | F | Cl | H | CH₃ | CH₃ | H | COOCH₂CH=CH₂ |
| 4-75 | F | Cl | H | CH₃ | CH₃ | H | COOCH₂C≡CH |
| 4-76 | F | Cl | H | CH₃ | CH₃ | H | CONH₂ |
| 4-77 | F | Cl | H | CH₃ | CH₃ | H | CONHCH₃ |
| 4-78 | F | Cl | H | CH₃ | CH₃ | H | CONHC₂H₅ |
| 4-79 | F | Cl | H | CH₃ | CH₃ | H | CON(CH₃)₂ |
| 4-80 | F | Cl | H | CH₃ | CH₃ | H | CON(C₂H₅)₂ |
| 4-81 | H | Cl | H | CH₃ | CH₃ | CH₃ | CH₂Cl |
| 4-82 | H | Cl | H | CH₃ | CH₃ | CH₃ | CH₂Br |
| 4-83 | H | Cl | H | CH₃ | CH₃ | CH₃ | CH₂OCH₃ |
| 4-84 | H | Cl | H | CH₃ | CH₃ | CH₃ | CH₂OC₂H₅ |
| 4-85 | H | Cl | H | CH₃ | CH₃ | CH₃ | CH₂OCH₂OCH₃ |
| 4-86 | H | Cl | H | CH₃ | CH₃ | CH₃ | CH₂OCH₂OC₂H₅ |
| 4-87 | H | Cl | H | CH₃ | CH₃ | CH₃ | CH₂OCOCH₃ |

TABLE 4-continued

Compounds of the formula:

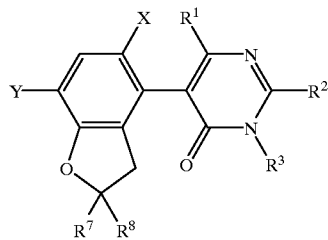
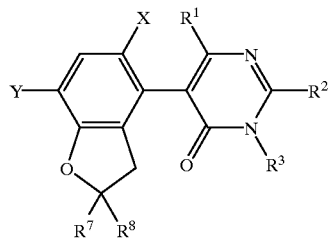

| Compound No. | X | Y | R¹ | R² | R³ | R⁷ | R⁸ |
|---|---|---|---|---|---|---|---|
| 4-88 | H | Cl | H | CH$_3$ | CH$_3$ | CH$_3$ | CH$_2$OCOC$_2$H$_5$ |
| 4-89 | H | Cl | H | CH$_3$ | CH$_3$ | CH$_3$ | CH$_2$OCO$^i$C$_3$H$_7$ |
| 4-90 | H | Cl | H | CH$_3$ | CH$_3$ | CH$_3$ | CH$_2$OCOCH$_2$Cl |
| 4-91 | H | Cl | H | CH$_3$ | CH$_3$ | CH$_3$ | CH$_2$OCOCCl$_3$ |
| 4-92 | H | Cl | H | CH$_3$ | CH$_3$ | CH$_3$ | CH$_2$OCOCF$_3$ |
| 4-93 | H | Cl | H | CH$_3$ | CH$_3$ | CH$_3$ | COOH |
| 4-94 | H | Cl | H | CH$_3$ | CH$_3$ | CH$_3$ | COOCH$_3$ |
| 4-95 | H | Cl | H | CH$_3$ | CH$_3$ | CH$_3$ | COOC$_2$H$_5$ |
| 4-96 | H | Cl | H | CH$_3$ | CH$_3$ | CH$_3$ | COO$^n$C$_3$H$_7$ |
| 4-97 | H | Cl | H | CH$_3$ | CH$_3$ | CH$_3$ | COO$^n$C$_4$H$_9$ |
| 4-98 | H | Cl | H | CH$_3$ | CH$_3$ | CH$_3$ | COO$^n$C$_5$H$_{11}$ |
| 4-99 | H | Cl | H | CH$_3$ | CH$_3$ | CH$_3$ | COO$^i$C$_3$H$_7$ |
| 4-100 | H | Cl | H | CH$_3$ | CH$_3$ | CH$_3$ | COO$^c$C$_5$H$_9$ |
| 4-101 | H | Cl | H | CH$_3$ | CH$_3$ | CH$_3$ | COO$^c$C$_6$H$_{11}$ |
| 4-102 | H | Cl | H | CH$_3$ | CH$_3$ | CH$_3$ | COOCH$_2$CH=CH$_2$ |
| 4-103 | H | Cl | H | CH$_3$ | CH$_3$ | CH$_3$ | COOCH$_2$C≡CH |
| 4-104 | H | Cl | H | CH$_3$ | CH$_3$ | CH$_3$ | CONH$_2$ |
| 4-105 | H | Cl | H | CH$_3$ | CH$_3$ | CH$_3$ | CONHCH$_3$ |
| 4-106 | H | Cl | H | CH$_3$ | CH$_3$ | CH$_3$ | CONHC$_2$H$_5$ |
| 4-107 | H | Cl | H | CH$_3$ | CH$_3$ | CH$_3$ | CON(CH$_3$)$_2$ |
| 4-108 | H | Cl | H | CH$_3$ | CH$_3$ | CH$_3$ | CON(C$_2$H$_5$)$_2$ |
| 4-109 | F | Cl | H | CH$_3$ | CH$_3$ | CH$_3$ | CH$_2$Cl |
| 4-110 | F | Cl | H | CH$_3$ | CH$_3$ | CH$_3$ | CH$_2$Br |
| 4-111 | F | Cl | H | CH$_3$ | CH$_3$ | CH$_3$ | CH$_2$OCH$_3$ |
| 4-112 | F | Cl | H | CH$_3$ | CH$_3$ | CH$_3$ | CH$_2$OC$_2$H$_5$ |
| 4-113 | F | Cl | H | CH$_3$ | CH$_3$ | CH$_3$ | CH$_2$OCH$_2$OCH$_3$ |
| 4-114 | F | Cl | H | CH$_3$ | CH$_3$ | CH$_3$ | CH$_2$OCH$_2$OC$_2$H$_5$ |
| 4-115 | F | Cl | H | CH$_3$ | CH$_3$ | CH$_3$ | CH$_2$OCOCH$_3$ |
| 4-116 | F | Cl | H | CH$_3$ | CH$_3$ | CH$_3$ | CH$_2$OCOC$_2$H$_5$ |
| 4-117 | F | Cl | H | CH$_3$ | CH$_3$ | CH$_3$ | CH$_2$OCO$^i$C$_3$H$_7$ |
| 4-118 | F | Cl | H | CH$_3$ | CH$_3$ | CH$_3$ | CH$_2$OCOCH$_2$Cl |
| 4-119 | F | Cl | H | CH$_3$ | CH$_3$ | CH$_3$ | CH$_2$OCOCCl$_3$ |
| 4-120 | F | Cl | H | CH$_3$ | CH$_3$ | CH$_3$ | CH$_2$OCOCF$_3$ |
| 4-121 | F | Cl | H | CH$_3$ | CH$_3$ | CH$_3$ | COOH |
| 4-122 | F | Cl | H | CH$_3$ | CH$_3$ | CH$_3$ | COOCH$_3$ |
| 4-123 | F | Cl | H | CH$_3$ | CH$_3$ | CH$_3$ | COOC$_2$H$_5$ |
| 4-124 | F | Cl | H | CH$_3$ | CH$_3$ | CH$_3$ | COO$^n$C$_3$H$_7$ |
| 4-125 | F | Cl | H | CH$_3$ | CH$_3$ | CH$_3$ | COO$^n$C$_4$H$_9$ |
| 4-126 | F | Cl | H | CH$_3$ | CH$_3$ | CH$_3$ | COO$^n$C$_5$H$_{11}$ |
| 4-127 | F | Cl | H | CH$_3$ | CH$_3$ | CH$_3$ | COO$^i$C$_3$H$_7$ |
| 4-128 | F | Cl | H | CH$_3$ | CH$_3$ | CH$_3$ | COO$^c$C$_5$H$_9$ |
| 4-129 | F | Cl | H | CH$_3$ | CH$_3$ | CH$_3$ | COO$^c$C$_6$H$_{11}$ |
| 4-130 | F | Cl | H | CH$_3$ | CH$_3$ | CH$_3$ | COOCH$_2$CH=CH$_2$ |
| 4-131 | F | Cl | H | CH$_3$ | CH$_3$ | CH$_3$ | COOCH$_2$C≡CH |
| 4-132 | F | Cl | H | CH$_3$ | CH$_3$ | CH$_3$ | CONH$_2$ |
| 4-133 | F | Cl | H | CH$_3$ | CH$_3$ | CH$_3$ | CONHCH$_3$ |
| 4-134 | F | Cl | H | CH$_3$ | CH$_3$ | CH$_3$ | CONHC$_2$H$_5$ |
| 4-135 | F | Cl | H | CH$_3$ | CH$_3$ | CH$_3$ | CON(CH$_3$)$_2$ |
| 4-136 | F | Cl | H | CH$_3$ | CH$_3$ | CH$_3$ | CON(C$_2$H$_5$)$_2$ |
| 4-137 | H | F | H | CF$_3$ | C$_2$H$_5$ | H | CH$_3$ |
| 4-138 | H | Cl | H | CF$_3$ | C$_2$H$_5$ | H | CH$_3$ |
| 4-139 | H | Br | H | CF$_3$ | C$_2$H$_5$ | H | CH$_3$ |
| 4-140 | H | F | H | CF$_3$ | C$_2$H$_5$ | H | CH$_2$OH |
| 4-141 | H | Cl | H | CF$_3$ | C$_2$H$_5$ | H | CH$_2$OH |
| 4-142 | H | Br | H | CF$_3$ | C$_2$H$_5$ | H | CH$_2$OH |
| 4-143 | H | F | H | CF$_3$ | C$_2$H$_5$ | CH$_3$ | CH$_3$ |
| 4-144 | H | Cl | H | CF$_3$ | C$_2$H$_5$ | CH$_3$ | CH$_3$ |
| 4-145 | H | Br | H | CF$_3$ | C$_2$H$_5$ | CH$_3$ | CH$_3$ |
| 4-146 | H | F | H | CF$_3$ | C$_2$H$_5$ | CH$_3$ | CH$_2$OH |
| 4-147 | H | Cl | H | CF$_3$ | C$_2$H$_5$ | CH$_3$ | CH$_2$OH |
| 4-148 | H | Br | H | CF$_3$ | C$_2$H$_5$ | CH$_3$ | CH$_2$OH |
| 4-149 | F | F | H | CF$_3$ | C$_2$H$_5$ | H | CH$_3$ |
| 4-150 | F | Cl | H | CF$_3$ | C$_2$H$_5$ | H | CH$_3$ |
| 4-151 | F | Br | H | CF$_3$ | C$_2$H$_5$ | H | CH$_3$ |
| 4-152 | F | F | H | CF$_3$ | C$_2$H$_5$ | H | CH$_2$OH |
| 4-153 | F | Cl | H | CF$_3$ | C$_2$H$_5$ | H | CH$_2$OH |
| 4-154 | F | Br | H | CF$_3$ | C$_2$H$_5$ | H | CH$_2$OH |
| 4-155 | F | F | H | CF$_3$ | C$_2$H$_5$ | CH$_3$ | CH$_3$ |
| 4-156 | F | Cl | H | CF$_3$ | C$_2$H$_5$ | CH$_3$ | CH$_3$ |
| 4-157 | F | Br | H | CF$_3$ | C$_2$H$_5$ | CH$_3$ | CH$_3$ |
| 4-158 | F | F | H | CF$_3$ | C$_2$H$_5$ | CH$_3$ | CH$_2$OH |
| 4-159 | F | Cl | H | CF$_3$ | C$_2$H$_5$ | CH$_3$ | CH$_2$OH |
| 4-160 | F | Br | H | CF$_3$ | C$_2$H$_5$ | CH$_3$ | CH$_2$OH |
| 4-161 | H | Cl | H | CF$_3$ | CH$_3$ | H | CH$_2$Cl |
| 4-162 | H | Cl | H | CF$_3$ | CH$_3$ | H | CH$_2$Br |
| 4-163 | H | Cl | H | CF$_3$ | CH$_3$ | H | CH$_2$OCH$_3$ |
| 4-164 | H | Cl | H | CF$_3$ | CH$_3$ | H | CH$_2$OC$_2$H$_5$ |
| 4-165 | H | Cl | H | CF$_3$ | CH$_3$ | H | CH$_2$OCH$_2$OCH$_3$ |
| 4-166 | H | Cl | H | CF$_3$ | CH$_3$ | H | CH$_2$OCH$_2$OC$_2$H$_5$ |
| 4-167 | H | Cl | H | CF$_3$ | CH$_3$ | H | CH$_2$OCOCH$_3$ |
| 4-168 | H | Cl | H | CF$_3$ | CH$_3$ | H | CH$_2$OCOC$_2$H$_5$ |
| 4-169 | H | Cl | H | CF$_3$ | CH$_3$ | H | CH$_2$OCO$^i$C$_3$H$_7$ |
| 4-170 | H | Cl | H | CF$_3$ | CH$_3$ | H | CH$_2$OCOCH$_2$Cl |
| 4-171 | H | Cl | H | CF$_3$ | CH$_3$ | H | CH$_2$OCOCCl$_3$ |
| 4-172 | H | Cl | H | CF$_3$ | CH$_3$ | H | CH$_2$OCOCF$_3$ |
| 4-173 | H | Cl | H | CF$_3$ | CH$_3$ | H | COOH |
| 4-174 | H | Cl | H | CF$_3$ | CH$_3$ | H | COOCH$_3$ |
| 4-175 | H | Cl | H | CF$_3$ | CH$_3$ | H | COOC$_2$H$_5$ |
| 4-176 | H | Cl | H | CF$_3$ | CH$_3$ | H | COO$^n$C$_3$H$_7$ |
| 4-177 | H | Cl | H | CF$_3$ | CH$_3$ | H | COO$^n$C$_4$H$_9$ |
| 4-178 | H | Cl | H | CF$_3$ | CH$_3$ | H | COO$^n$C$_5$H$_{11}$ |
| 4-179 | H | Cl | H | CF$_3$ | CH$_3$ | H | COO$^i$C$_3$H$_7$ |
| 4-180 | H | Cl | H | CF$_3$ | CH$_3$ | H | COO$^c$C$_5$H$_9$ |
| 4-181 | H | Cl | H | CF$_3$ | CH$_3$ | H | COO$^c$C$_6$H$_{11}$ |
| 4-182 | H | Cl | H | CF$_3$ | CH$_3$ | H | COOCH$_2$CH=CH$_2$ |
| 4-183 | H | Cl | H | CF$_3$ | CH$_3$ | H | COOCH$_2$C≡CH |
| 4-184 | H | Cl | H | CF$_3$ | CH$_3$ | H | CONH$_2$ |
| 4-185 | H | Cl | H | CF$_3$ | CH$_3$ | H | CONHCH$_3$ |
| 4-186 | H | Cl | H | CF$_3$ | CH$_3$ | H | CONHC$_2$H$_5$ |
| 4-187 | H | Cl | H | CF$_3$ | CH$_3$ | H | CON(CH$_3$)$_2$ |
| 4-188 | H | Cl | H | CF$_3$ | CH$_3$ | H | CON(C$_2$H$_5$)$_2$ |
| 4-189 | F | Cl | H | CF$_3$ | CH$_3$ | H | CH$_2$Cl |
| 4-190 | F | Cl | H | CF$_3$ | CH$_3$ | H | CH$_2$Br |
| 4-191 | F | Cl | H | CF$_3$ | CH$_3$ | H | CH$_2$OCH$_3$ |
| 4-192 | F | Cl | H | CF$_3$ | CH$_3$ | H | CH$_2$OC$_2$H$_5$ |
| 4-193 | F | Cl | H | CF$_3$ | CH$_3$ | H | CH$_2$OCH$_2$OCH$_3$ |
| 4-194 | F | Cl | H | CF$_3$ | CH$_3$ | H | CH$_2$OCH$_2$OC$_2$H$_5$ |
| 4-195 | F | Cl | H | CF$_3$ | CH$_3$ | H | CH$_2$OCOCH$_3$ |
| 4-196 | F | Cl | H | CF$_3$ | CH$_3$ | H | CH$_2$OCOC$_2$H$_5$ |
| 4-197 | F | Cl | H | CF$_3$ | CH$_3$ | H | CH$_2$OCO$^i$C$_3$H$_7$ |
| 4-198 | F | Cl | H | CF$_3$ | CH$_3$ | H | CH$_2$OCOCH$_2$Cl |
| 4-199 | F | Cl | H | CF$_3$ | CH$_3$ | H | CH$_2$OCOCCl$_3$ |
| 4-200 | F | Cl | H | CF$_3$ | CH$_3$ | H | CH$_2$OCOCF$_3$ |
| 4-201 | F | Cl | H | CF$_3$ | CH$_3$ | H | COOH |
| 4-202 | F | Cl | H | CF$_3$ | CH$_3$ | H | COOCH$_3$ |
| 4-203 | F | Cl | H | CF$_3$ | CH$_3$ | H | COOC$_2$H$_5$ |
| 4-204 | F | Cl | H | CF$_3$ | CH$_3$ | H | COO$^n$C$_3$H$_7$ |
| 4-205 | F | Cl | H | CF$_3$ | CH$_3$ | H | COO$^n$C$_4$H$_9$ |
| 4-206 | F | Cl | H | CF$_3$ | CH$_3$ | H | COO$^n$C$_5$H$_{11}$ |
| 4-207 | F | Cl | H | CF$_3$ | CH$_3$ | H | COO$^i$C$_3$H$_7$ |
| 4-208 | F | Cl | H | CF$_3$ | CH$_3$ | H | COO$^c$C$_5$H$_9$ |
| 4-209 | F | Cl | H | CF$_3$ | CH$_3$ | H | COO$^c$C$_6$H$_{11}$ |

TABLE 4-continued

Compounds of the formula:

| Compound No. | X | Y | R¹ | R² | R³ | R⁷ | R⁸ |
|---|---|---|---|---|---|---|---|
| 4-210 | F | Cl | H | $CF_3$ | $CH_3$ | H | $COOCH_2CH=CH_2$ |
| 4-211 | F | Cl | H | $CF_3$ | $CH_3$ | H | $COOCH_2C\equiv CH$ |
| 4-212 | F | Cl | H | $CF_3$ | $CH_3$ | H | $CONH_2$ |
| 4-213 | F | Cl | H | $CF_3$ | $CH_3$ | H | $CONHCH_3$ |
| 4-214 | F | Cl | H | $CF_3$ | $CH_3$ | H | $CONHC_2H_5$ |
| 4-215 | F | Cl | H | $CF_3$ | $CH_3$ | H | $CON(CH_3)_2$ |
| 4-216 | F | Cl | H | $CF_3$ | $CH_3$ | H | $CON(C_2H_5)_2$ |
| 4-217 | H | Cl | H | $CF_3$ | $CH_3$ | $CH_3$ | $CH_2Cl$ |
| 4-218 | H | Cl | H | $CF_3$ | $CH_3$ | $CH_3$ | $CH_2Br$ |
| 4-219 | H | Cl | H | $CF_3$ | $CH_3$ | $CH_3$ | $CH_2OCH_3$ |
| 4-220 | H | Cl | H | $CF_3$ | $CH_3$ | $CH_3$ | $CH_2OC_2H_5$ |
| 4-221 | H | Cl | H | $CF_3$ | $CH_3$ | $CH_3$ | $CH_2OCH_2OCH_3$ |
| 4-222 | H | Cl | H | $CF_3$ | $CH_3$ | $CH_3$ | $CH_2OCH_2OC_2H_5$ |
| 4-223 | H | Cl | H | $CF_3$ | $CH_3$ | $CH_3$ | $CH_2OCOCH_3$ |
| 4-224 | H | Cl | H | $CF_3$ | $CH_3$ | $CH_3$ | $CH_2OCOC_2H_5$ |
| 4-225 | H | Cl | H | $CF_3$ | $CH_3$ | $CH_3$ | $CH_2OCO^iC_3H_7$ |
| 4-226 | H | Cl | H | $CF_3$ | $CH_3$ | $CH_3$ | $CH_2OCOCH_2Cl$ |
| 4-227 | H | Cl | H | $CF_3$ | $CH_3$ | $CH_3$ | $CH_2OCOCCl_3$ |
| 4-228 | H | Cl | H | $CF_3$ | $CH_3$ | $CH_3$ | $CH_2OCOCF_3$ |
| 4-229 | H | Cl | H | $CF_3$ | $CH_3$ | $CH_3$ | $COOH$ |
| 4-230 | H | Cl | H | $CF_3$ | $CH_3$ | $CH_3$ | $COOCH_3$ |
| 4-231 | H | Cl | H | $CF_3$ | $CH_3$ | $CH_3$ | $COOC_2H_5$ |
| 4-232 | H | Cl | H | $CF_3$ | $CH_3$ | $CH_3$ | $COO^nC_3H_7$ |
| 4-233 | H | Cl | H | $CF_3$ | $CH_3$ | $CH_3$ | $COO^nC_4H_9$ |
| 4-234 | H | Cl | H | $CF_3$ | $CH_3$ | $CH_3$ | $COO^nC_5H_{11}$ |
| 4-235 | H | Cl | H | $CF_3$ | $CH_3$ | $CH_3$ | $COO^iC_3H_7$ |
| 4-236 | H | Cl | H | $CF_3$ | $CH_3$ | $CH_3$ | $COO^cC_5H_9$ |
| 4-237 | H | Cl | H | $CF_3$ | $CH_3$ | $CH_3$ | $COO^cC_6H_{11}$ |
| 4-238 | H | Cl | H | $CF_3$ | $CH_3$ | $CH_3$ | $COOCH_2CH=CH_2$ |
| 4-239 | H | Cl | H | $CF_3$ | $CH_3$ | $CH_3$ | $COOCH_2C\equiv CH$ |
| 4-240 | H | Cl | H | $CF_3$ | $CH_3$ | $CH_3$ | $CONH_2$ |
| 4-241 | H | Cl | H | $CF_3$ | $CH_3$ | $CH_3$ | $CONHCH_3$ |
| 4-242 | H | Cl | H | $CF_3$ | $CH_3$ | $CH_3$ | $CONHC_2H_5$ |
| 4-243 | H | Cl | H | $CF_3$ | $CH_3$ | $CH_3$ | $CON(CH_3)_2$ |
| 4-244 | H | Cl | H | $CF_3$ | $CH_3$ | $CH_3$ | $CON(C_2H_5)_2$ |
| 4-245 | F | Cl | H | $CF_3$ | $CH_3$ | $CH_3$ | $CH_2Cl$ |
| 4-246 | F | Cl | H | $CF_3$ | $CH_3$ | $CH_3$ | $CH_2Br$ |
| 4-247 | F | Cl | H | $CF_3$ | $CH_3$ | $CH_3$ | $CH_2OCH_3$ |
| 4-248 | F | Cl | H | $CF_3$ | $CH_3$ | $CH_3$ | $CH_2OC_2H_5$ |
| 4-249 | F | Cl | H | $CF_3$ | $CH_3$ | $CH_3$ | $CH_2OCH_2OCH_3$ |
| 4-250 | F | Cl | H | $CF_3$ | $CH_3$ | $CH_3$ | $CH_2OCH_2OC_2H_5$ |
| 4-251 | F | Cl | H | $CF_3$ | $CH_3$ | $CH_3$ | $CH_2OCOCH_3$ |
| 4-252 | F | Cl | H | $CF_3$ | $CH_3$ | $CH_3$ | $CH_2OCOC_2H_5$ |
| 4-253 | F | Cl | H | $CF_3$ | $CH_3$ | $CH_3$ | $CH_2OCO^iC_3H_7$ |
| 4-254 | F | Cl | H | $CF_3$ | $CH_3$ | $CH_3$ | $CH_2OCOCH_2Cl$ |
| 4-255 | F | Cl | H | $CF_3$ | $CH_3$ | $CH_3$ | $CH_2OCOCCl_3$ |
| 4-256 | F | Cl | H | $CF_3$ | $CH_3$ | $CH_3$ | $CH_2OCOCF_3$ |
| 4-257 | F | Cl | H | $CF_3$ | $CH_3$ | $CH_3$ | $COOH$ |
| 4-258 | F | Cl | H | $CF_3$ | $CH_3$ | $CH_3$ | $COOCH_3$ |
| 4-259 | F | Cl | H | $CF_3$ | $CH_3$ | $CH_3$ | $COOC_2H_5$ |
| 4-260 | F | Cl | H | $CF_3$ | $CH_3$ | $CH_3$ | $COO^nC_3H_7$ |
| 4-261 | F | Cl | H | $CF_3$ | $CH_3$ | $CH_3$ | $COO^nC_4H_9$ |
| 4-262 | F | Cl | H | $CF_3$ | $CH_3$ | $CH_3$ | $COO^nC_5H_{11}$ |
| 4-263 | F | Cl | H | $CF_3$ | $CH_3$ | $CH_3$ | $COO^iC_3H_7$ |
| 4-264 | F | Cl | H | $CF_3$ | $CH_3$ | $CH_3$ | $COO^cC_5H_9$ |
| 4-265 | F | Cl | H | $CF_3$ | $CH_3$ | $CH_3$ | $COO^cC_6H_{11}$ |
| 4-266 | F | Cl | H | $CF_3$ | $CH_3$ | $CH_3$ | $COOCH_2CH=CH_2$ |
| 4-267 | F | Cl | H | $CF_3$ | $CH_3$ | $CH_3$ | $COOCH_2C\equiv CH$ |
| 4-268 | F | Cl | H | $CF_3$ | $CH_3$ | $CH_3$ | $CONH_2$ |
| 4-269 | F | Cl | H | $CF_3$ | $CH_3$ | $CH_3$ | $CONHCH_3$ |
| 4-270 | F | Cl | H | $CF_3$ | $CH_3$ | $CH_3$ | $CONHC_2H_5$ |
| 4-271 | F | Cl | H | $CF_3$ | $CH_3$ | $CH_3$ | $CON(CH_3)_2$ |
| 4-272 | F | Cl | H | $CF_3$ | $CH_3$ | $CH_3$ | $CON(C_2H_5)_2$ |

TABLE 5

Compounds of the formula:

| Compound No. | X | R¹ | R² | R³ | R⁵ |
|---|---|---|---|---|---|
| 5-1 | H | H | $CH_3$ | $CH_3$ | $CH_3$ |
| 5-2 | H | H | $CH_3$ | $CH_3$ | $C_2H_5$ |
| 5-3 | H | H | $CH_3$ | $CH_3$ | $^iC_3H_7$ |
| 5-4 | H | H | $CH_3$ | $CH_3$ | $^nC_3H_7$ |
| 5-5 | H | H | $CH_3$ | $CH_3$ | $^iC_4H_9$ |
| 5-6 | H | H | $CH_3$ | $CH_3$ | $CH_2CH=CH_2$ |
| 5-7 | H | H | $CH_3$ | $CH_3$ | $CH(CH_3)CH=CH_2$ |
| 5-8 | H | H | $CH_3$ | $CH_3$ | $CH_2C\equiv CH$ |
| 5-9 | H | H | $CH_3$ | $CH_3$ | $CH(CH_3)C\equiv CH$ |
| 5-10 | F | H | $CH_3$ | $CH_3$ | $CH_3$ |
| 5-11 | F | H | $CH_3$ | $CH_3$ | $C_2H_5$ |
| 5-12 | F | H | $CH_3$ | $CH_3$ | $^iC_3H_7$ |
| 5-13 | F | H | $CH_3$ | $CH_3$ | $^nC_3H_7$ |
| 5-14 | F | H | $CH_3$ | $CH_3$ | $^iC_4H_9$ |
| 5-15 | F | H | $CH_3$ | $CH_3$ | $CH_2CH=CH_2$ |
| 5-16 | F | H | $CH_3$ | $CH_3$ | $CH(CH_3)CH=CH_2$ |
| 5-17 | F | H | $CH_3$ | $CH_3$ | $CH_2C\equiv CH$ |
| 5-18 | F | H | $CH_3$ | $CH_3$ | $CH(CH_3)C\equiv CH$ |
| 5-19 | H | H | $CF_3$ | $CH_3$ | $CH_3$ |
| 5-20 | H | H | $CF_3$ | $CH_3$ | $C_2H_5$ |
| 5-21 | H | H | $CF_3$ | $CH_3$ | $^iC_3H_7$ |
| 5-22 | H | H | $CF_3$ | $CH_3$ | $^nC_3H_7$ |
| 5-23 | H | H | $CF_3$ | $CH_3$ | $^iC_4H_5$ |
| 5-24 | H | H | $CF_3$ | $CH_3$ | $CH_2CH=CH_2$ |
| 5-25 | H | H | $CF_3$ | $CH_3$ | $CH(CH_3)CH=CH_2$ |
| 5-26 | H | H | $CF_3$ | $CH_3$ | $CH_2C\equiv CH$ |
| 5-27 | H | H | $CF_3$ | $CH_3$ | $CH(CH_3)C\equiv CH$ |
| 5-28 | F | H | $CF_3$ | $CH_3$ | $CH_3$ |
| 5-29 | F | H | $CF_3$ | $CH_3$ | $C_2H_5$ |
| 5-30 | F | H | $CF_3$ | $CH_3$ | $^iC_3H_7$ |
| 5-31 | F | H | $CF_3$ | $CH_3$ | $^iC_4H_9$ |
| 5-32 | F | H | $CF_3$ | $CH_3$ | $CH_2CH=CH_2$ |
| 5-33 | F | H | $CF_3$ | $CH_3$ | $CH(CH_3)CH=CH_2$ |
| 5-34 | F | H | $CF_3$ | $CH_3$ | $CH_2C\equiv CH$ |
| 5-35 | F | H | $CF_3$ | $CH_3$ | $CH(CH_3)C\equiv CH$ |

The following will describe production examples for compound [2] which is an intermediate compound for the production of the present compounds.

INTERMEDIATE PRODUCTION EXAMPLE 1

First, 7.5 g of ethyl E- and Z-2-(4'-chlorophenyl)-3-methoxyacrylate was dissolved in 180 ml of ethanol, to which 11.0 g of acetarmfidine hydrochloride and 16.1 g of potassium carbonate were added, and the mixture was stirred at 60° C. for 2.5 hours. The reaction mixture was cooled to room temperature, neutralized by the addition of acetic acid, and concentrated. The precipitated crystals were collected by filtration, washed with water, and dried, which afforded 6.5 g of compound 1-1002.

$^1$H-NMR (60 MHz, DMSO-$d_6$): δ (ppm) 2.30 (3H, s), 7.35 (2H, d, J=9 Hz), 7.70 (2H, d, J=9 Hz), 8.05 (1H, s)

INTERMEDIATE PRODUCTION EXAMPLE 2

First, 2.8 g of ethyl E- and Z-2-(2',4'-difluorophenyl)-3-methoxyacrylate was dissolved in 70 ml of ethanol, to which 4.1 g of acetamidine hydrochloride and 6.0 g of potassium carbonate were added, and the mixture was stirred at 60° C. for 3 hours. The reaction mixture was cooled to room temperature, neutralized by the addition of acetic acid, and concentrated. The precipitated crystals were collected by filtration, washed with water, and dried, which afforded 2.0 g of compound 1-1004.

INTERMEDIATE PRODUCTION EXAMPLE 3

First, 1.5 ml of trifluoroacetamidine was added to 1.0 g of ethyl 2-(4'-chlorophenyl)-2-formylacetate, and the mixture was stirred at room temperature for 5 hours. After completion of the reaction, the reaction mixture was subjected to silica gel chromatography, which afforded 0.3 g of compound 1-1008.

$^1$H-NMR (60 MHz, CDCl$_3$+DMSO-$d_6$): δ (ppm) 7.30 (2H, d, J=9 Hz), 7.55 (2H, d, J=9 Hz), 8.30(1H, s)

INTERMEDIATE PRODUCTION EXAMPLE 4

First, 1.0 ml of trifluoroacetamidine was added to 1.0 g of ethyl E- and Z-2-(4'-chlorophenyl)-3-methoxyacrylate, followed by stirring for 3 hours, to which 0.5 ml of trifluoroacetamidine was further added, and the mixture was stiffed at 60° C. for 4 hours. The reaction mixture was cooled to room temperature and subjected to silica gel chromatography, which afforded 0.8 g of compound 1-1008. The physical properties are the same as those obtained in Intermediate Production Example 3.

INTERMEDIATE PRODUCTION EXAMPLE 5

First, 5.0 ml of trifluoroacetamidine was added to 5.0 g of ethyl 2-(2',4'-difluorophenyl)-2-formylacetate, and the mixture was stirred at room temperature for 17 hours. After completion of the reaction, the reaction mixture was subjected to silica gel chromatography, which afforded 0.5 g of compound 1-1010.

$^1$H-NMR (250 MHz, CDCl$_3$+DMSO-$d_6$): δ (ppm) 6.80–7.00 (2H, m), 7.45–7.55 (1H, m), 7.94 (1H, s)

INTERMEDIATE PRODUCTION EXAMPLE 6

First, 7 ml of trifluoroacetamidine was added to 6.9 g of ethyl E- and Z-2-(2',4'-difluorophenyl)-3-methoxyacrylate, and the mixture was stirred at room temperature for 23 hours. After completion of the reaction, the reaction mixture was subjected to silica gel chromatography, which afforded 3.9 g of compound 1-1010. The physical properties are the same as those obtained in Intermediate Production Example 5.

INTERMEDIATE PRODUCTION EXAMPLE 7

First, 5.15 g of ethyl E- and Z-2-(2',4'-dichlorophenyl)-3-methoxyacrylate was dissolved in 150 ml of ethanol, to which 6.08 g of acetamidine hydrochloride and 11.02 g of potassium carbonate were added, and the mixture was stirred at 60° C. for 3.5 hours. After completion of the reaction, the reaction mixture was cooled to room temperature, neutralized by the addition of acetic acid, and concentrated. The precipitated crystals were collected by filtration and dried, which afforded 4.35 g of compound 1-1013, m.p. 250° C. or higher (decomp.).

INTERMEDIATE PRODUCTION EXAMPLE 8

First, 10 ml of trifluoroacetamidine was added to 2.2 g of ethyl (E- and Z-) 2-(4'-chloro-2'-fluoro-5'-isopropoxy)-3-methoxyacrylate, and the mixture was stirred at room temperature for 28 hours. After completion of the reaction, the reaction mixture was subjected to silica gel column chromatography, which afforded 2.0 g of compound 1-1014.

$^1$H-NMR (250 MHz, CDCl$_3$): δ (ppm) 1.34 (6H, d, J=6.0 Hz), 4.44 (1H, hp, J=6 Hz), 6.82 (1H, d, J=6.6 Hz), 7.00 (1H, d, J=7.8 Hz), 8.18 (1H, s)

INTERMEDIATE PRODUCTION EXAMPLE 9

First, 5 ml of trifluoroacetamidine was added to 4.0 g of ethyl E- and Z-2-(4'-fluorophenyl)-3-methoxyacrylate, and the reaction was allowed to proceed at room temperature for 47 hours. After completion of the reaction, the reaction mixture was subjected to silica gel column chromatography, which afforded 3.5 g of compound 1-1007.

$^1$H-NMR (250 MHz, CDCl$_3$): δ (ppm) 7.05 (2H, dd, J=9.7, 9.7 Hz), 7.62 (2H, dd, J=5.5, 9.7 Hz), 8.23 (1H, s)

INTERMEDIATE PRODUCTION EXAMPLE 10

First, 5.0 ml of trifluoroacetamidine was added to 3.0 g of ethyl E- and Z-2-(2',4'-dichlorophenyl)-3-methoxyacrylate, and the reaction was allowed to proceed for 5 days. After completion of the reaction, the reaction mixture was subjected to silica gel column chromatography, which afforded 3.5 g of compound 1-1015 as a crude product.

INTERMEDIATE PRODUCTION EXAMPLE 11

First, 50 g of trifluoroacetamidine was added to 34 g of ethyl E- and Z-2-(4'-chloro-2'-fluorophenyl)-3-methoxyacrylate, and the reaction was allowed to proceed for 4 days. After completion of the reaction, the reaction mixture was subjected to silica gel column chromatography, which afforded 25.6 g of compound 1-1011.

$^1$H-NMR (250 MHz, CDCl$_3$): δ (ppm) 7.05–7.12 (2H, m), 7.40 (1H, dd, J=7.9, 7.9 Hz), 8.21 (1H, d, J=1.2 Hz)

Examples of compound [2] are shown with their compound numbers in Tables 6 to 8.

TABLE 6

Compound of the formula:

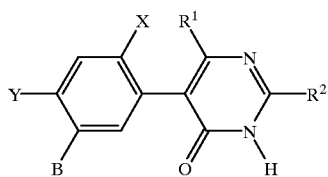

| Compound No. | X | Y | R¹ | R² | B |
|---|---|---|---|---|---|
| 1-1001 | H | F | H | $CH_3$ | H |
| 1-1002 | H | Cl | H | $CH_3$ | H |
| 1-1003 | H | Br | H | $CH_3$ | H |
| 1-1004 | F | F | H | $CH_3$ | H |
| 1-1005 | F | Cl | H | $CH_3$ | H |
| 1-1006 | F | Br | H | $CH_3$ | H |
| 1-1007 | H | F | H | $CF_3$ | H |
| 1-1008 | H | Cl | H | $CF_3$ | H |
| 1-1009 | H | Br | H | $CF_3$ | H |
| 1-1010 | F | F | H | $CF_3$ | H |
| 1-1011 | F | Cl | H | $CF_3$ | H |
| 1-1012 | F | Br | H | $CF_3$ | H |
| 1-1013 | Cl | Cl | H | $CF_3$ | H |
| 1-1014 | F | Cl | H | $CF_3$ | $OCH(CH_3)_2$ |
| 1-1015 | Cl | Cl | H | CF3 | H |

TABLE 7

Compound of the formula:

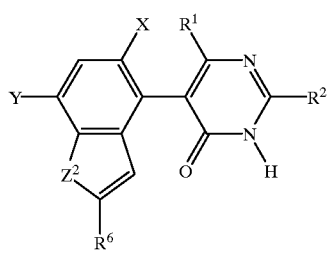

| Compound No. | X | Y | Z² | R¹ | R² | R⁶ |
|---|---|---|---|---|---|---|
| 3-1001 | H | F | O | H | $CH_3$ | $CH_3$ |
| 3-1002 | H | Cl | O | H | $CH_3$ | $CH_3$ |
| 3-1003 | H | Br | O | H | $CH_3$ | $CH_3$ |
| 3-1004 | F | F | O | H | $CH_3$ | $CH_3$ |
| 3-1005 | F | Cl | O | H | $CH_3$ | $CH_3$ |
| 3-1006 | F | Br | O | H | $CH_3$ | $CH_3$ |
| 3-1007 | H | F | O | H | $CH_3$ | $C_2H_5$ |
| 3-1008 | H | Cl | O | H | $CH_3$ | $C_2H_5$ |
| 3-1009 | H | Br | O | H | $CH_3$ | $C_2H_5$ |
| 3-1010 | F | F | O | H | $CH_3$ | $C_2H_5$ |
| 3-1011 | F | Cl | O | H | $CH_3$ | $C_2H_5$ |
| 3-1012 | F | Br | O | H | $CH_3$ | $C_2H_5$ |
| 3-1013 | H | F | O | H | $CF_3$ | $CH_3$ |
| 3-1014 | H | Cl | O | H | $CF_3$ | $CH_3$ |
| 3-1015 | H | Br | O | H | $CF_3$ | $CH_3$ |
| 3-1016 | F | F | O | H | $CF_3$ | $CH_3$ |
| 3-1017 | F | Cl | O | H | $CF_3$ | $CH_3$ |
| 3-1018 | F | Br | O | H | $CF_3$ | $CH_3$ |
| 3-1019 | H | F | O | H | $CF_3$ | $C_2H_5$ |
| 3-1020 | H | Cl | O | H | $CF_3$ | $C_2H_5$ |
| 3-1021 | H | Br | O | H | $CF_3$ | $C_2H_5$ |
| 3-1022 | F | F | O | H | $CF_3$ | $C_2H_5$ |
| 3-1023 | F | Cl | O | H | $CF_3$ | $C_2H_5$ |
| 3-1024 | F | Br | O | H | $CF_3$ | $C_2H_5$ |

TABLE 8

Compound of the formula:

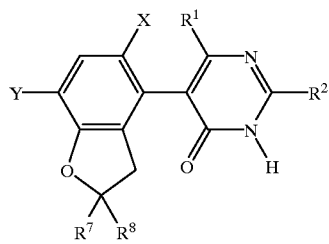

| Compound No. | X | Y | R¹ | R² | R⁷ | R⁸ |
|---|---|---|---|---|---|---|
| 4-1001 | H | F | H | $CH_3$ | H | $CH_3$ |
| 4-1002 | H | Cl | H | $CH_3$ | H | $CH_3$ |
| 4-1003 | H | Br | H | $CH_3$ | H | $CH_3$ |
| 4-1004 | H | F | H | $CH_3$ | H | $CH_2OH$ |
| 4-1005 | H | Cl | H | $CH_3$ | H | $CH_2OH$ |
| 4-1006 | H | Br | H | $CH_3$ | H | $CH_2OH$ |
| 4-1007 | H | F | H | $CH_3$ | $CH_3$ | $CH_3$ |
| 4-1008 | H | Cl | H | $CH_3$ | $CH_3$ | $CH_3$ |
| 4-1009 | H | Br | H | $CH_3$ | $CH_3$ | $CH_3$ |
| 4-1010 | H | F | H | $CH_3$ | $CH_3$ | $CH_2OH$ |
| 4-1011 | H | Cl | H | $CH_3$ | $CH_3$ | $CH_2OH$ |
| 4-1012 | H | Br | H | $CH_3$ | $CH_3$ | $CH_2OH$ |
| 4-1013 | F | F | H | $CH_3$ | H | $CH_3$ |
| 4-1014 | F | Cl | H | $CH_3$ | H | $CH_3$ |
| 4-1015 | F | Br | H | $CH_3$ | H | $CH_3$ |
| 4-1016 | F | F | H | $CH_3$ | H | $CH_2OH$ |
| 4-1017 | F | Cl | H | $CH_3$ | H | $CH_2OH$ |
| 4-1018 | F | Br | H | $CH_3$ | H | $CH_2OH$ |
| 4-1019 | F | F | H | $CH_3$ | $CH_3$ | $CH_3$ |
| 4-1020 | F | Cl | H | $CH_3$ | $CH_3$ | $CH_3$ |
| 4-1021 | F | Br | H | $CH_3$ | $CH_3$ | $CH_3$ |
| 4-1022 | F | F | H | $CH_3$ | $CH_3$ | $CH_2OH$ |
| 4-1023 | F | Cl | H | $CH_3$ | $CH_3$ | $CH_2OH$ |
| 4-1024 | F | Br | H | $CH_3$ | $CH_3$ | $CH_2OH$ |
| 4-1025 | H | F | H | $CF_3$ | H | $CH_3$ |
| 4-1026 | H | Cl | H | $CF_3$ | H | $CH_3$ |
| 4-1027 | H | Br | H | $CF_3$ | H | $CH_3$ |
| 4-1028 | H | F | H | $CF_3$ | H | $CH_2OH$ |
| 4-1029 | H | Cl | H | $CF_3$ | H | $CH_2OH$ |
| 4-1030 | H | Br | H | $CF_3$ | H | $CH_2OH$ |
| 4-1031 | H | F | H | $CF_3$ | $CH_3$ | $CH_3$ |
| 4-1032 | H | Cl | H | $CF_3$ | $CH_3$ | $CH_3$ |
| 4-1033 | H | Br | H | $CF_3$ | $CH_3$ | $CH_3$ |
| 4-1034 | H | F | H | $CF_3$ | $CH_3$ | $CH_2OH$ |
| 4-1035 | H | Cl | H | $CF_3$ | $CH_3$ | $CH_2OH$ |
| 4-1036 | H | Br | H | $CF_3$ | $CH_3$ | $CH_2OH$ |
| 4-1037 | F | F | H | $CF_3$ | H | $CH_3$ |
| 4-1038 | F | Cl | H | $CF_3$ | H | $CH_3$ |
| 4-1039 | F | Br | H | $CF_3$ | H | $CH_3$ |
| 4-1040 | F | F | H | $CF_3$ | H | $CH_2OH$ |
| 4-1041 | F | Cl | H | $CF_3$ | H | $CH_2OH$ |
| 4-1042 | F | Br | H | $CF_3$ | H | $CH_2OH$ |
| 4-1043 | F | F | H | $CF_3$ | $CH_3$ | $CH_3$ |
| 4-1044 | F | Cl | H | $CF_3$ | $CH_3$ | $CH_3$ |
| 4-1045 | F | Br | H | $CF_3$ | $CH_3$ | $CH_3$ |
| 4-1046 | F | F | H | $CF_3$ | $CH_3$ | $CH_2OH$ |
| 4-1047 | F | Cl | H | $CF_3$ | $CH_3$ | $CH_2OH$ |
| 4-1048 | F | Br | H | $CF_3$ | $CH_3$ | $CH_2OH$ |

The following will describe production examples for compounds [5] and [27] which are starting compounds for the production of the present compounds.

REFERENCE EXAMPLE 1

Production of ethyl 2-(4'-chlorophenyl)-2-formylacetate and ethyl E- and Z-2-(4'-chlorophenyl)-3-methoxyacrylate First, 17.24 g of 4-chlorophenylacetic acid was dissolved in 200 ml of ethanol, to which a catalytic amount of p-toluenesulfonic acid was added, and the mixture was heated under reflux for 10 hours. After completion of the reaction, the reaction mixture was cooled to room temperature and concentrated. The residue was poured into water and extracted with ethyl acetate, and the organic layer was dried and then concentrated. The residue was subjected to silica gel chromatography, which afforded 19.0 g of ethyl 4-chlorophenylacetate.

Then, 4.19 g of sodium hydride (60% in oil) was suspended in 150 ml of tetrahydrofuran, to which a solution of 19.0 g of ethyl 4-chlorophenylacetate in 150 ml of tetrahydrofuran was added dropwise at 5° to 10° C. After stirring at room temperature for 1.5 hours, 8.42 g of ethyl formate was added, and the mixture was further stirred at room temperature for 4.5 hours. After completion of the reaction, the reaction mixture was cooled to ice temperature, neutralized by the addition of diluted hydrochloric acid, and concentrated. The residue was subjected to phase separation with ethyl acetatewater, and the organic layer was dried and then concentrated. The residue was subjected to silica gel chromatography, which afforded 17.0 g of ethyl 2-(4'-chlorophenyl)-2-formylacetate.

Then, 1.93 g of sodium hydride (60% in oil) was suspended in 90 ml of 1,2-dimethoxyethane, to which 90 ml of a solution of ethyl 2-(4'-chlorophenyl)-2-formylacetate was added dropwise at 5° to 10° C. After stirring at room temperature for 1⅓ hours, 11.76 g of methyl iodide was added dropwise, and the mixture was further stirred at room temperature for 20 hours. After completion of the reaction, the reaction mixture was cooled with ice, and excess sodium hydride was decomposed by the addition of water, followed by extraction with ethyl acetate-water. The organic layer was dried and then concentrated, and the residue was subjected to silica gel chromatography, which afforded 7.58 g of ethyl E- and Z-2-(4'-chlorophenyl)-3-methoxyacrylate.

REFERENCE EXAMPLE 2

Production of ethyl 2-(2',4'-difluorophenyl)-2-formylacetate and ethyl E- and Z-2-(2',4'-difluorophenyl)-3-methoxyacrylate Ethyl 2-(2',4'-difluorophenyl)-2-formylacetate and ethyl E- and Z-2-(2',4'-difluorophenyl)-3-methoxyacrylate were synthesized with 2,4-difluorophenylacetate as the starting compound in the same manner as described in Reference Example 1.

REFERENCE EXAMPLE 3

Production of ethyl 2-(2',4'-dichlorophenyl)-2-formylacetate and ethyl E- and Z-2-(2',4'-dichlorophenyl)-3-methoxyacrylate Ethyl 2-(2',4'-dichlorophenyl)-2-formylacetate and ethyl E- and Z-2-(2',4'-dichlorophenyl)-3-methoxyacrylate were synthesized with 2,4-dichlorophenylacetate as the starting compound in the same manner as described in Reference Example 1.

REFERENCE EXAMPLE 4

Production of ethyl 2-(4-chloro-2-fluoro-5-isopropoxyphenyl)-2-formylacetate and ethyl (E- and Z-) 2-(4'-chloro-2'-fluoro-5'-isopropoxy)-3-methoxyacrylate (1) First, 250 ml of water and 25 ml of concentrated sulfuric acid were added to 30 g of 4-chloro-2-fluoro-5-isopropoxyaniline, and the mixture was stirred at 50° C. for 2.5 hours and then cooled to 0° C., to which a solution of 10.4 g of sodium nitrite in 80 ml of water was slowly added dropwise. The solution of a diazonium salt thus formed was added dropwise to a solution of 150 g of potassium iodide in 300 ml of water at room temperature, and the mixture was stirred for at room temperature for 45 minutes. After completion of the reaction, the reaction mixture was extracted with diethyl ether, and the organic layer was washed with saturated sodium chloride solution, dried, and concentrated. The residue was subjected to silica gel column chromatography, which afforded 36 g of 2-chloro-4-fluoro-5-iodo-1-isopropoxybenzene.

$^1$H-NMR (250 MHz, CDCl$_3$): δ (ppm) 1.36 (6H, d, J=6.2 Hz), 4.46 (1H, hp, J=6.2 Hz), 7.11 (1H, d, J=7.2 Hz), 7.27 (1H, d, J=5.7 Hz)

(2) Then, 62.9 g of 2-chloro-4-fluoro-5-iodo-1-isopropoxybenzene, 20.4 g of sodium formate, and 2.81 g of dichlorobis(triphenylphosphine)palladium were dissolved in 120 ml of N,N-dimethylformamide, which was stirred at 90° to 100° C. for 12 hours, while bubbling carbon monoxide thereinto. After completion of the reaction, the reaction mixture was cooled to room temperature, to which diluted hydrochloric acid was added, and the mixture was extracted with ethyl acetate. The organic layer was washed with saturated sodium chloride solution, dried, and concentrated. The residue was subjected to silica gel column chromatography, which afforded 15 g of 4-chloro-2-fluoro-5-isopropoxybenzaldehyde.

$^1$H-NMR (300 MHz, CDCl$_3$): δ (ppm) 1.31 (6H, d, J=6.3 Hz), 4.52 (1H, hp, J=6.3 Hz), 7.18 (1H, d, J=9.7 Hz), 7.29 (1H, d, J=6.1 Hz), 10.2 (1H, s)

(3) Then, 7.5 g of 4-chloro-2-fluoro-5-isopropoxybenzaldehyde was dissolved in 70 ml of 1,4-dioxane and 5 ml of methanol, to which 0.92 g of sodium borohydride was added at 5° C., and the mixture was stirred for 40 minutes. After completion of the reaction, a small amount of diluted hydrochloric acid was added, and the reaction mixture was poured into water and extracted with ethyl acetate. The organic layer was washed with saturated sodium chloride solution, dried, and concentrated. The residue was subjected to silica gel column chromatography, which afforded 6.7 g of 4-chloro-2-fluoro-5-isopropoxybenzyl alcohol.

$^1$H-NMR (250 MHz, CDCl$_3$): δ (ppm) 1.36 (6H, d, J=6.0 Hz), 1.96 (1H, br), 4.49 (1H, hp, J=6.0 Hz), 4.71 (1H, d, J=5.2 Hz), 7.04 (1H, d, J=6.7 Hz), 7.09 (1H, d, J=9.2 Hz)

(4) Then, 6.7 g of 4-chloro-2-fluoro-5-isopropoxybenzylalcohol was dissolved in 70 ml of tetrahydrofuran, to which 1 ml of pyridine was added, and the mixture was cooled to 5° C. Then, 5 ml of thionyl chloride was slowly added dropwise at 5° to 10° C., and the mixture was stirred at 5° C. for 1.5 hours. After completion of the reaction, the reaction mixture was filtered to separate the precipitated crystals, and the filtrate was concentrated. The residue was subjected to silica gel column chromatography, which afforded 7.3 g of 4-chloro-2-fluoro-5-isopropoxybenzyl chloride.

$^1$H-NMR (300 MHz, CDCl$_3$): δ (ppm) 1.37 (6H, d, J=6.0 Hz), 4.49 (1H, hp, J=6.0 Hz), 4.57 (2H, s), 6.99 (1H, d, J=6.8 Hz), 7.13 (1H, d, J=9.2 Hz)

(5) Then, 7.3 g of 4-chloro-2-fluoro-5-isopropoxybenzyl chloride was dissolved in 70 ml of ethanol and 30 ml of water, to which 1.8 g of sodium cyanide was added, and the mixture was heated under reflux for 2 hours. After completion of the reaction, the reaction mixture was poured into water and extracted with ethyl acetate. The organic layer was washed with saturated sodium chloride solution, dried, and concentrated. The residue was subjected to silica gel column chromatography, which 7.0 g of 4-chloro-2-fluoro-5-isopropoxyphenylacetonitrile.

$^1$H-NMR (250 MHz, CDCl$_3$): δ (ppm) 1.38 (6H, d, J=5.9 Hz), 3.73 (2H, s), 4.51 (1H, hp, J=5.9 Hz), 7.00 (1H, d, J=6.8 Hz), 7.16 (H, d, J=9.0 Hz)

(6) Then, 7.0 g of 4-chloro-2-fluoro-5-isopropoxyphenylacetonitrile was dissolved in 100 ml of ethanol, to which 5 ml of sulfuric acid, and the mixture was heated under reflux for 66 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 7.2 g of ethyl 4-chloro-2-fluoro-5-isopropoxyphenyl acetate.

$^1$H-NMR (250 MHz, CDCl$_3$): δ (ppm) 1.26 (3H, t, J=7.1 Hz), 1.36 (6H, d, J=6.0 Hz), 3.60 (2H, s), 4.17 (2H, q, J=7.1 Hz), 4.46 (1H, hp, J=6.0 Hz), 6.87 (1H, d, J=6.8 Hz), 7.10 (1H, d, J=9.0Hz)

(7) Then, 1.1 g of sodium hydride (60% in oil) was suspended in 50 ml of tetrahydrofuran, and the mixture was cooled to 5° C., to which a solution of 7.2 g of ethyl 4-chloro-2-fluoro-5-isopropoxyphenylacetate in 80 ml of tetrahydrofuran was slowly added dropwise. The mixture was stirred for 30 minutes with a gradual temperature increase to room temperature, to which 10 ml of ethyl formate was added at room temperature, followed by stirring for 3 hours. Then, the reaction mixture was cooled to 5° C., to which diluted hydrochloric acid was added. The reaction mixture was concentrated, and the residue was poured into water and extracted with ethyl acetate. The organic layer was washed with saturated sodium chloride solution, dried, and concentrated. The residue was subjected to silica gel column chromatography, which afforded 8.0 g of ethyl 2-(4-chloro-2-fluoro-5-isopropoxyphenyl)-2-formylacetate.

$^1$H-NMR (300 MHz, CDCl$_3$): δ (ppm) 1.26 (3H, t, J=7.0 Hz), 1.36 (6H, d, J=6.2 Hz), 4.26 (2H, q, J=7.0 Hz), 4.45 (1H, hp, J=6.2 Hz), 6.76 (½H, s), 6.78 (½H, s), 7.10 (1H, d, J=8.9 Hz), 7.26 (1H, d, J=12.6 Hz), 12.1 (½H, s), 12.2 (½H, s)

(8) Then, 1.1 g of sodium hydride (60% in oil) was suspended in 50 ml of 1,2-dimethoxyethane, and the mixture was cooled to 5° C., to which a solution of 8.0 g of ethyl 2-(4-chloro-2-fluoro-5-isopropoxyphenyl)-2-formylacetate in 50 ml of 1,2-dimethoxyethane was slowly added dropwise. The mixture was stirred for 20 minutes with a gradual temperature increase to room temperature, to which 3.0 ml of methyl iodide was added at room temperature, followed by stirring for 4.5 hours. Then, the reaction mixture was cooled to 5° C., to which diluted aqueous hydrochloric acid was added. The reaction mixture was poured into water and extracted with ethyl acetate. The organic layer was washed with saturated sodium chloride solution, dried, and concentrated. The residue was subjected to silica gel column chromatography, which afforded 5.5 g of ethyl (E- and Z-)2-(4'-chloro-2'-fluoro-5'-isopropoxyphenyl)-3-methoxyacrylate.

REFERENCE EXAMPLE 5
Production of ethyl E- and Z-2-(4'-fluorophenyl)-3-methoxyacrylate Ethyl E- and Z-2-(4'-fluorophenyl)-3-methoxyacrylate was synthesized with 4-fluorophenylacetate as the starting compound in the same manner as described in Reference Example 1.

REFERENCE EXAMPLE 6
Production of ethyl E- and Z-2-(4'-chloro-2'-fluorophenyl)-3-methoxyacrylate (1) First, 25 g of 4-chloro-2-fluorobenzaldehyde was dissolved in a mixed solvent consisting of 250 ml of 1,4-dioxane and 25 ml of methanol, to which 2.4 g of sodium borohydride was added under ice cooling, and the mixture was stirred for 30 minutes. After completion of the reaction, a small amount of diluted aqueous hydrochloric acid was added, and the reaction mixture was poured into water and extracted with ethyl acetate. The organic layer was washed with saturated sodium chloride solution, dried, and concentrated. The residue was subjected to silica gel column chromatography, which afforded 25 g of 4-chloro-2-fluorobenzyl alcohol.

$^1$H-NMR (300 MHz, CDCl$_3$): δ (ppm) 1.82 (1H, t, J=6.1 Hz), 4.72 (2H, d, J=6.1 Hz), 7.08 (1H, dd, J=2.1, 9.8 Hz), 7.15 (1H, dd, J=2.1, 8.2 Hz), 7.37 (1H, dd, J=8.2, 8.2 Hz)

(2) Then, 16.5 g of 4-chloro-2-fluorobenzylalcohol was dissolved in 150 ml of tetrahydrofuran and 1 ml of pyridine, to which 10 ml of thionyl chloride was added dropwise at 5° C., and the mixture was stirred for 2⅚ hours. After completion of the reaction, the reaction mixture was concentrated, and the precipitated crystals were collected by filtration. The filtrate was subjected to silica gel column chromatography, which afforded 18.5 g of 4-chloro-2-fluorobenzyl chloride.

$^1$H-NMR (250 MHz, CDCl$_3$): δ (ppm) 4.59 (2H, s), 7.09–7.17 (2H, m), 7.36 (1H, dd, J=7.9, 7.9 Hz)

(3) Then, 18.5 g of 4-chloro-2-fluorobenzyl chloride was dissolved in a mixed solvent consisting of 130 ml of ethanol and 30 ml of water, to which 5.3 g of sodium cyanide was added, and the mixture was heated under reflux for 2 hours. After completion of the reaction, the reaction mixture was allowed to stand for cooling to room temperature, poured into water, and extracted with ethyl acetate. The organic layer was washed with saturated sodium chloride solution, dried, and concentrated. The residue was subjected to silica gel column chromatography, which afforded 15.1 g of 4-chloro-2-fluorophenylacetonitrile.

$^1$H-NMR (250 MHz, CDCl$_3$): δ (ppm) 3.74 (2H, s), 7.12–7.22 (2H, m), 7.39 (1H, dd, J=8.0, 8.0 Hz)

(4) Then, 15.1 g of 4-chloro-2-fluoroacetonitrile was dissolved in 150 ml of ethanol, to which 10 ml of sulfuric acid was added, and the mixture was heated under reflux for 65 hours. After completion of the reaction, the reaction mixture was poured into water and extracted with ethyl acetate. The organic layer was washed with saturated sodium chloride solution, dried, and concentrated. The residue was subjected to silica gel column chromatography, which afforded 17.8 g of ethyl 4-chloro-2-fluorophenylacetate.

$^1$H-NMR (250 MHz, CDCl$_3$): δ (ppm) 1.25 (3H, t, J=7.1 Hz), 3.63 (2H, s), 4.17 (2H, q, J=7.1 Hz), 7.07–7.24 (3H, m)

(5) Then, 3.6 g of sodium hydride (60% in oil) was suspended in 120 ml of tetrahydrofuran, and the mixture was cooled to 5° C., to which a solution of 17.8 g of ethyl 4-chloro-2-fluorophenylacetate in 120 nm of tetrahydrofliran was slowly added dropwise. The mixture was stirred for 30 minutes with a gradual temperature increase to room temperature, to which 20 ml of ethyl formate was added at room temperature, followed by stirring for 3 hours. Then, the reaction mixture was cooled with ice, to which diluted aqueous hydrochloric acid was added. The reaction mixture was poured into water and extracted with ethyl acetate. The organic layer was washed with saturated sodium chloride solution, dried, and concentrated. The residue was subjected to silica gel column chromatography, which afforded 19.1 g of ethyl 2-(4-chloro-2-fluorophenyl)-2-formylacetate.

$^1$H-NMR (250 MHz, CDCl$_3$): δ (ppm) 1.25 (⅓H, t, J=7.1 Hz), 1.26 (⅓H, t, J=7.1 Hz), 4.26 (2H, q, J=7.1 Hz), 7.07–7.26 (3H, m), 9.74 (½H, br), 9.80 (½H, br)

(6) Then, 3.4 g of sodium hydride (60% in oil) was suspended in 120 ml of 1,2-dimethoxyethane, and the mixture was cooled to 5° C., to which a solution of 19.1 g of ethyl 2-(4-chloro-2-fluorophenyl)-2-formylacetate in 120 ml of 1,2-dimethoxyethane was slowly added dropwise. The mixture was stirred for 30 minutes with a gradual temperature increase to room temperature, to which 10 ml of methyl iodide at room temperature, and the mixture was stirred for 3⅓ hours. Then, the reaction mixture was cooled with ice, to which diluted aqueous hydrochloric acid was added. The reaction mixture was poured into water and extracted with ethyl acetate. The organic layer was washed with saturated sodium chloride solution, dried, and concentrated, The residue was subjected to silica gel column chromatography, which afforded 11.1 g of ethyl E- and Z-2-(4'-chloro-2'-fluorophenyl)-3-methoxyacrylate.

The following will describe formulation examples for the present compounds, where the present compounds are designated by their compound numbers shown in Tables 1 to 5 and parts are by weight.

FORMULATION EXAMPLE 1

Fifty parts of each of compounds 1-1 to 1-715, 2-1 to 2-380, 3-1 to 3-256, 4-1 to 4-272, and 5-1 to 5-35, 3 parts of calcium ligninsulfonate, 2 parts of sodium laurylsulfate, and 45 parts of synthetic hydrated silicon oxide are well pulverized and mixed to give a wettable powder for each compound.

FORMULATION EXAMPLE 2

Ten parts of each of compounds 1-1 to 1-715, 2-1 to 2-380, 3-1 to 3-256, 4-1 to 4-272, and 5-1 to 5-35, 14 parts of polyoxyethylene styryl phenyl ether, 6 parts of calcium dodecylbenzenesulfonate, 35 parts of xylene, and 35 parts of cyclohexanone are well mixed to give an emulsifiable concentrate for each compound.

FORMULATION EXAMPLE 3

Two parts of each of compounds 1-1 to 1-715, 2-1 to 2-380, 3-1 to 3-256, 4-1 to 4-272, and 5-1 to 5-35, 2 parts of synthetic hydrated silicon oxide, 2 parts of calcium ligninsulfonate, 30 parts of bentonite, and 64 parts of kaoline clay are well pulverized and mixed, to which water is added, and the mixture is well kneaded, granulated, and dried to give a granule for each compound.

FORMULATION EXAMPLE 4

Twenty-five parts of each of compounds 1-1 to 1-715, 2-1 to 2-380, 3-1 to 3-256, 4-1 to 4-272, and 5-1 to 5-35, 50 parts of 10% aqueous polyvinyl alcohol solution, and 25 parts of water are mixed, and the mixture is pulverized until the average particle size becomes 5 μm or less to give a flowable for each compound.

The following test examples will demonstrate that the present compounds are useful as active ingredients of herbicides. The present compounds are designated by their compound numbers shown in Tables 1 to 5.

The herbicidal activity was evaluated at 6 levels with indices of 0 to 5, i.e., designated by the numeral "0", "1", "2", "3", "4" or "5", wherein "0" means that there was no or little difference in the degree of germination or growth between the treated and the untreated test plants at the time of examination, and "5" means that the test plants died complete or their germination or growth was completely inhibited. The herbicidal activity is excellent when rated at "4" or "5" but insufficient when rated at "3" or lower.

Test Example 1: Foliar treatment on upland fields

Cylindrical plastic pots of 10 cm in diameter and 10 cm in depth were filled with soil, in which the seeds of velvetleaf (Abutilon theophrasti) were sowed, and the test plants were grown in a greenhouse for 15 days. Each of the test compounds listed below was formulated into an emulsifiable concentrate according to Formulation Example 2, which was diluted with water containing a spreading agent to a prescribed concentration. The dilution was uniformly sprayed over the foliage of the test plants with a sprayer at a volume of 1000 liters per hectare. After the application, the test plants were grown in the greenhouse for 15 days, and the herbicidal activity was examined. The results are shown in Table 9.

TABLE 9

| Test compound | Application amount of active ingredient (g/ha) | Herbicidal activity Velvetleaf |
| --- | --- | --- |
| 1-5 | 2000 | 4 |
| 1-10 | 2000 | 4 |
| 1-335 | 2000 | 5 |
| 1-340 | 2000 | 5 |
| 1-662 | 2000 | 4 |
| 2-203 | 125 | 5 |
| 2-251 | 125 | 5 |
| 2-252 | 125 | 5 |

Test Example 2: Soil surface treatment on upland fields

Cylindrical plastic pots of 10 cm in diameter and 10 cm in depth were filled with soil, in which the seeds of velvetleaf (Abutilon theophrasti) were sowed. Each of the test compounds listed below was formulated into an emulsifiable concentrate according to Formulation Example 2, which was diluted with water to a prescribed concentration. The dilution was uniformly sprayed over the soil surface in the pots with a sprayer at a volume of 1000 liters per hectare. After the application, the test plants were grown in a greenhouse for 19 days, and the herbicidal activity was examined. The results are shown in Table 10.

TABLE 10

| Test compound | Application amount of active ingredient (g/ha) | Herbicidal activity Velvetleaf |
| --- | --- | --- |
| 1-335 | 2000 | 5 |
| 1-668 | 500 | 5 |
| 2-251 | 500 | 5 |

Test Example 3: Flooding treatment on paddy fields

Cylindrical plastic pots of 9 cm in diameter and 11 cm in depth were filled with soil, in which the seeds of barnyardgrass (Echinochloa oryzicola) were sowed. These pots were flooded to form a paddy field, and the test plants were grown in a greenhouse for 7 days. Each of the test compounds listed below was formulated into an emulsifiable concentrate according to Formulation Example 2, which was diluted with water to a prescribed concentration. The dilution was applied to the water surface in the pots with a syringe at a volume of 50 liters per are. After the application, the test plants were grown in the greenhouse for 19 days, and the herbicidal activity was examined. The results are shown in Table 11.

TABLE 11

| Test compound | Application amount of active ingredient (g/ha) | Herbicidal activity Barnyardgrass |
|---|---|---|
| 1-335 | 1000 | 5 |
| 1-340 | 1000 | 5 |
| 2-251 | 250 | 5 |

Test Example 4: Foliar treatment on upland fields

Cylindrical plastic pots of 10 cm in diameter and 10 cm in depth were filled with soil, in which the seeds of velvetleaf (*Abutilon theophrasti*) and barnyardgrass (*Echinochloa crus-galli*) were sowed, and the test plants were grown in a greenhouse for 15 days. Each of the test compounds listed below was formulated into an emulsifiable concentrate according to Formulation Example 2, which was diluted with water containing a spreading agent to a prescribed concentration. The dilution was uniformly sprayed over the foliage of the test plants with a sprayer at a volume of 1000 liters per hectare. After the application, the test plants were grown in the greenhouse for 15 days, and the herbicidal activity was examined. The results are shown in Table 12.

TABLE 12

| Test compound | Application amount of active ingredient (g/ha) | Herbicidal activity | |
|---|---|---|---|
| | | Barnyardgrass | Velvetleaf |
| 1-341 | 500 | 5 | 5 |
| 1-367 | 500 | 5 | 5 |
| 1-391 | 500 | 4 | 5 |
| 1-420 | 500 | 5 | 5 |
| 1-482 | 500 | 4 | 5 |
| 1-486 | 500 | 5 | 5 |
| 1-487 | 500 | 4 | 5 |
| 1-491 | 500 | 5 | 5 |
| 1-495 | 500 | 5 | 5 |
| 1-496 | 500 | 4 | 5 |
| 1-499 | 500 | 5 | 5 |
| 1-503 | 500 | 5 | 5 |
| 1-504 | 500 | 5 | 5 |
| 1-663 | 500 | 5 | 5 |
| 1-667 | 500 | 5 | 5 |
| 1-668 | 500 | 5 | 5 |
| 2-252 | 500 | 5 | 5 |

Test Example 5: Soil surface treatment on upland fields

Cylindrical plastic pots of 10 cm in diameter and 10 cm in depth were filled with soil, in which the seeds of velvetleaf (*Abutilon theophrasti*) and barnyardgrass (*Echinochloa crus-galli*) were sowed. Each of the test compounds listed below was formulated into an emulsifiable concentrate according to Formulation Example 2, which was diluted with water to a prescribed concentration. The dilution was uniformly sprayed over the soil surface in the pots with a sprayer at a volume of 1000 liters per hectare. After the application, the test plants were grown in the greenhouse for 19 days, and the herbicidal activity was examined. The results are shown in Table 13.

TABLE 13

| Test compound | Application amount of active ingredient (g/ha) | Herbicidal activity | |
|---|---|---|---|
| | | Barnyardgrass | Velvetleaf |
| 1-341 | 2000 | 5 | 5 |
| 1-367 | 2000 | 5 | 5 |
| 1-391 | 2000 | 4 | 5 |
| 1-420 | 2000 | 5 | 5 |
| 1-482 | 2000 | 5 | 5 |
| 1-486 | 2000 | 5 | 5 |
| 1-487 | 2000 | 5 | 5 |
| 1-491 | 2000 | 5 | 5 |
| 1-495 | 2000 | 5 | 5 |
| 1-496 | 2000 | 5 | 5 |
| 1-499 | 2000 | 4 | 5 |
| 1-503 | 2000 | 5 | 5 |
| 1-504 | 2000 | 5 | 5 |
| 1-663 | 2000 | 5 | 5 |
| 1-667 | 2000 | 5 | 5 |
| 2-203 | 2000 | 5 | 5 |
| 2-251 | 2000 | 5 | 5 |
| 2-252 | 2000 | 5 | 5 |

Test Example 6: Flooding treatment on paddy fields

Cylindrical plastic pots of 9 cm in diameter and 11 cm in depth were filled with soil, in which the seeds of barnyardgrass (*Echinochloa oryzicola*) and hardstem bulrush (*Scirpus juncoides*) were sowed. These pots were flooded to form a paddy field, and the test plants were grown in a greenhouse for 7 days. Each of the test compounds listed below was formulated into an emulsifiable concentrate according to Formulation Example 2, which was diluted with water to a prescribed concentration. The dilution was applied to the water surface in the pots with a syringe at a volume of 50 liters per are. After the application, the test plants were grown in the greenhouse for 19 days, and the herbicidal activity was examined. The results are shown in Table 14.

TABLE 14

| Test compound | Application amount of active ingredient (g/ha) | Herbicidal activity | |
|---|---|---|---|
| | | Barnyardgrass | Hardstem bulrush |
| 1-341 | 250 | 5 | 5 |
| 1-347 | 250 | 5 | 4 |
| 1-367 | 250 | 5 | 5 |
| 1-420 | 250 | 5 | 5 |
| 1-482 | 250 | 5 | 5 |
| 1-486 | 250 | 5 | 5 |
| 1-487 | 250 | 5 | 5 |
| 1-491 | 250 | 5 | 5 |
| 1-495 | 250 | 5 | 5 |
| 1-496 | 250 | 5 | 5 |
| 1-499 | 250 | 5 | 4 |
| 1-503 | 250 | 5 | 4 |
| 1-504 | 250 | 5 | 5 |
| 1-663 | 250 | 5 | 5 |
| 1-667 | 250 | 5 | 5 |
| 1-668 | 250 | 5 | 5 |
| 2-203 | 250 | 5 | 5 |
| 2-251 | 250 | 5 | 4 |
| 2-252 | 250 | 5 | 5 |

Test Example 7: Foliar treatment on upland fields

Plastic pots of 26.5×19 cm² in area and 7 cm in depth were filled with soil, in which the seeds of ivyleaf morningglory (*Iponioea hederacea*), common cocklebur (*Xanthium pensylvanicum*), common ragweed (*Ambrosia artemisiifolia*), and barnyardgrass (*Echiniochloa cris-galli*)

were sowed and grown so that the application of a chemical to these weed species was made after 23, 27, 30, and 17 days from sowing, respectively. Each of the test compounds listed below was formulated into an emulsifiable concentrate according to Formulation Example 2, which was diluted with water to a prescribed concentration. The dilution was uniformly sprayed over the foliage of the test plants with a sprayer at a volume of 1050 liters per hectare. At this time, the unfavorable weeds, although their growth stage was different depending upon the weed species, were at the 2- to 4-leaf stage, and the plant height was 8 to 18 cm. After 21 days from the application, the herbicidal activity was examined. The results are shown in Table 15. This test was made in a greenhouse over the test period.

TABLE 15

| Test compound | Application amount of active ingredient (g/ha) | Herbicidal activity | | | |
|---|---|---|---|---|---|
| | | Common cocklebur | Ivyleaf morning-glory | Common ragweed | Barnyard-grass |
| 1-367 | 250 | 5 | 5 | 5 | 4 |
| 1-420 | 250 | 5 | 5 | 5 | 5 |
| 1-486 | 250 | 5 | 5 | 5 | 5 |
| 1-491 | 250 | 5 | 5 | 5 | 4 |
| 1-495 | 250 | 5 | 5 | 5 | 5 |
| 1-496 | 250 | 5 | 5 | 5 | 4 |
| 1-499 | 250 | 5 | 5 | 5 | 5 |
| 1-503 | 250 | 5 | 5 | 5 | 5 |
| 1-504 | 250 | 5 | 5 | 5 | 5 |
| 1-667 | 250 | 5 | 5 | 5 | 5 |
| 2-203 | 250 | 5 | 5 | 4 | 5 |
| 2-252 | 250 | 5 | 5 | 5 | 5 |

What is claimed is:

1. A compound of the formula:

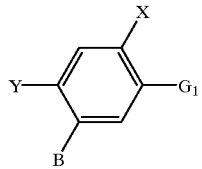

wherein

X is halogen,

Y is halogen, $G_1$ is cyanomethyl or ($C_1$–$C_3$ alkoxy)carbonylmethyl, and

B is —$OR^{10}$, —$SR^{10}$, —$NHR^{10}$ or —$COOR^{13}$, wherein $R^{10}$ is $C_1$–$C_6$ alkyl, $C_1$–$C_6$ haloalkyl, $C_3$–$C_8$ cycloalkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_2$–$C_8$ alkoxyalkyl or $C_2$–$C_8$ alkylthioalkyl, and $R^{13}$ is $C_1$–$C_6$ alkyl, $C_1$–$C_6$ haloalkyl or $C_3$–$C_8$ cycloalkyl.

2. A compound of the formula:

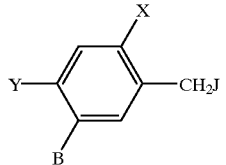

wherein

X is fluorine,

Y is halogen,

J is chlorine or bromine and

B is —$OR^{10}$, —$SR^{10}$, —$NHR^{10}$ or —$COOR^{13}$, wherein $R^{10}$ is $C_1$–$C_6$ alkyl, $C_1$–$C_6$ haloalkyl, $C_3$–$C_8$ cycloalkyl, $C_3$–$C_6$ alkenyl, $C_3$–$C_6$ haloalkenyl, $C_3$–$C_6$ alkynyl, $C_1$–$C_6$ haloalkynyl, cyano $C_1$–$C_6$ alkyl, $C_2$–$C_8$ alkoxyalkyl or $C_2$–$C_8$ alkylthioalkyl, and $R^{13}$ is $C_1$–$C_6$ alkyl, $C_1$–$C_6$ haloalkyl or $C_3$–$C_8$ cycloalkyl.

3. The compound 4-chloro-2-fluoro-5-isopropoxybenzaldehyde.

4. A compound according to claim 1, wherein $G_1$ is cyanomethyl.

5. A compound according to 1, wherein $G_1$ is ($C_1$–$C_3$ alkoxy) carbonylmethyl.

* * * * *